(12) United States Patent
Brandt

(10) Patent No.: US 11,654,275 B2
(45) Date of Patent: May 23, 2023

(54) INTRAVASCULAR BLOOD PUMPS WITH STRUTS AND METHODS OF USE AND MANUFACTURE

(71) Applicant: Shifamed Holdings, LLC, Campbell, CA (US)

(72) Inventor: Brian D. Brandt, Morgan Hill, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 151 days.

(21) Appl. No.: 16/936,160

(22) Filed: Jul. 22, 2020

(65) Prior Publication Data

US 2021/0023285 A1 Jan. 28, 2021

Related U.S. Application Data

(60) Provisional application No. 62/877,154, filed on Jul. 22, 2019.

(51) Int. Cl.
| | |
|---|---|
| *A61M 60/216* | (2021.01) |
| *A61M 60/808* | (2021.01) |
| *A61M 60/857* | (2021.01) |
| *A61M 60/268* | (2021.01) |
| *A61M 60/414* | (2021.01) |

(52) U.S. Cl.
CPC ........ *A61M 60/857* (2021.01); *A61M 60/268* (2021.01); *A61M 60/414* (2021.01); *A61M 2205/0266* (2013.01); *A61M 2207/00* (2013.01)

(58) Field of Classification Search
CPC .............. A61M 2207/00; A61M 60/13; A61M 60/237; A61M 60/414; A61M 60/808; A61M 60/857; A61M 2205/0266; A61M 2230/30; A61M 60/139; A61M 60/174; A61M 60/216; A61M 60/268; A61M 60/295; A61M 60/804; A61M 60/81; A61M 60/816; A61M 60/865
See application file for complete search history.

(56) References Cited

U.S. PATENT DOCUMENTS

| | | | |
|---|---|---|---|
| 1,061,107 | A | 5/1913 | Nordmark |
| 1,596,933 | A | 8/1926 | Kister |

(Continued)

FOREIGN PATENT DOCUMENTS

| | | |
|---|---|---|
| CA | 2739899 C | 5/2017 |
| CN | 1040073 A | 2/1990 |

(Continued)

OTHER PUBLICATIONS

Hildebrand et al.; U.S. Appl. No. 17/632,550 entitled Catheter blood pumps and impellers,: filed Feb. 3, 2022.

(Continued)

*Primary Examiner* — Jon Eric C Morales
(74) *Attorney, Agent, or Firm* — Shay Glenn LLP

(57) ABSTRACT

Catheter blood pumps that include an expandable pump portion, which include an expandable impeller housing. The housings include an expandable blood conduit that defines a blood lumen, and one or more pluralities of expandable struts extending axially from an end region of the expandable blood conduit. At least one of the pluralities of struts are non-unitary with a blood conduit at the end region.

35 Claims, 18 Drawing Sheets

(56) References Cited

U.S. PATENT DOCUMENTS

| | | |
|---|---|---|
| 3,152,618 A | 10/1964 | Rothermel et al. |
| 3,175,555 A | 3/1965 | Ling |
| 3,178,833 A | 4/1965 | Gulbransen, Jr. |
| 3,208,448 A | 9/1965 | Woodward |
| 3,233,609 A | 2/1966 | Leucci |
| 3,421,497 A | 1/1969 | Chesnut |
| 3,502,412 A | 3/1970 | Burns |
| 3,504,662 A | 4/1970 | Jones |
| 3,505,987 A | 4/1970 | Heilman |
| 3,568,659 A | 3/1971 | Karnegis |
| 3,693,612 A | 9/1972 | Donahoe et al. |
| 3,734,648 A | 5/1973 | Nielson |
| 3,774,243 A | 11/1973 | Ng et al. |
| 3,837,922 A | 9/1974 | Ng et al. |
| 3,841,837 A | 10/1974 | Kitrilakis et al. |
| 3,860,968 A | 1/1975 | Shapiro |
| 3,919,722 A | 11/1975 | Harmison |
| 4,015,590 A | 4/1977 | Normann |
| 4,037,984 A | 7/1977 | Rafferty et al. |
| 4,046,137 A | 9/1977 | Curless et al. |
| 4,058,857 A | 11/1977 | Runge et al. |
| 4,093,726 A | 6/1978 | Winn et al. |
| 4,135,253 A | 1/1979 | Reich et al. |
| 4,142,845 A | 3/1979 | Lepp et al. |
| 4,173,796 A | 11/1979 | Jarvik |
| 4,190,047 A | 2/1980 | Jacobsen et al. |
| 4,255,821 A | 3/1981 | Carol et al. |
| 4,289,141 A | 9/1981 | Cormier |
| 4,310,930 A | 1/1982 | Goldowsky |
| 4,311,133 A | 1/1982 | Robinson |
| 4,328,806 A | 5/1982 | Cooper |
| 4,370,983 A | 2/1983 | Lichtenstein |
| 4,381,005 A | 4/1983 | Bujan |
| 4,381,567 A | 5/1983 | Robinson et al. |
| 4,382,199 A | 5/1983 | Isaacson |
| 4,389,737 A | 6/1983 | Robinson et al. |
| 4,397,049 A | 8/1983 | Robinson et al. |
| 4,407,304 A | 10/1983 | Lieber et al. |
| 4,506,658 A | 3/1985 | Casile |
| 4,515,589 A | 5/1985 | Austin et al. |
| 4,522,195 A | 6/1985 | Schiff |
| 4,524,466 A | 6/1985 | Hall et al. |
| 4,551,073 A | 11/1985 | Schwab |
| 4,576,606 A | 3/1986 | Pol et al. |
| 4,585,004 A | 4/1986 | Brownlee |
| 4,585,007 A | 4/1986 | Uchigaki et al. |
| 4,599,081 A | 7/1986 | Cohen |
| 4,600,405 A | 7/1986 | Zibelin |
| 4,623,350 A | 11/1986 | Lapeyre et al. |
| 4,625,712 A | 12/1986 | Wampler |
| 4,652,265 A | 3/1987 | McDougall |
| 4,662,358 A | 5/1987 | Farrar et al. |
| 4,666,598 A | 5/1987 | Heath et al. |
| 4,675,361 A | 6/1987 | Ward |
| 4,685,910 A | 8/1987 | Schweizer |
| 4,726,379 A | 2/1988 | Altman et al. |
| 4,753,221 A | 6/1988 | Kensey et al. |
| 4,767,289 A | 8/1988 | Parrot et al. |
| 4,771,777 A | 9/1988 | Horzewski et al. |
| 4,779,614 A | 10/1988 | Moise |
| 4,782,817 A | 11/1988 | Singh et al. |
| 4,785,795 A | 11/1988 | Singh |
| 4,802,650 A | 2/1989 | Stricker |
| 4,818,186 A | 4/1989 | Pastrone et al. |
| 4,826,481 A | 5/1989 | Sacks et al. |
| 4,846,831 A | 7/1989 | Skillin |
| 4,850,957 A | 7/1989 | Summers |
| 4,888,009 A | 12/1989 | Lederman et al. |
| 4,888,011 A | 12/1989 | Kung et al. |
| 4,902,272 A | 2/1990 | Milder et al. |
| 4,907,592 A | 3/1990 | Harper |
| 4,908,012 A | 3/1990 | Moise et al. |
| 4,919,647 A | 4/1990 | Nash |
| 4,936,759 A | 6/1990 | Clausen et al. |
| 4,961,738 A | 10/1990 | Mackin |
| 4,976,683 A | 12/1990 | Gauthier et al. |
| 4,995,857 A | 2/1991 | Arnold |
| 5,026,367 A | 6/1991 | Leckrone et al. |
| D318,113 S | 7/1991 | Moutafis et al. |
| 5,045,051 A | 9/1991 | Milder |
| 5,046,503 A | 9/1991 | Schneiderman |
| 5,047,147 A | 9/1991 | Chevallet et al. |
| 5,049,134 A | 9/1991 | Golding et al. |
| 5,084,064 A | 1/1992 | Barak et al. |
| 5,089,016 A | 2/1992 | Millner et al. |
| 5,090,957 A | 2/1992 | Moutafis et al. |
| 5,092,844 A | 3/1992 | Schwartz et al. |
| 5,092,879 A | 3/1992 | Jarvik |
| 5,112,200 A | 5/1992 | Isaacson et al. |
| 5,112,292 A | 5/1992 | Hwang et al. |
| 5,114,399 A | 5/1992 | Kovalcheck |
| 5,116,305 A | 5/1992 | Milder et al. |
| 5,139,517 A | 8/1992 | Corral |
| 5,145,333 A | 9/1992 | Smith |
| 5,147,281 A | 9/1992 | Thornton et al. |
| 5,171,264 A | 12/1992 | Merrill |
| 5,180,378 A | 1/1993 | Kung et al. |
| 5,192,314 A | 3/1993 | Daskalakis |
| 5,200,050 A | 4/1993 | Ivory et al. |
| 5,205,721 A | 4/1993 | Isaacson |
| 5,211,546 A | 5/1993 | Isaacson et al. |
| 5,261,411 A | 11/1993 | Hughes |
| 5,270,005 A | 12/1993 | Raible |
| 5,300,111 A | 4/1994 | Panton et al. |
| 5,300,112 A | 4/1994 | Barr |
| 5,314,418 A | 5/1994 | Takano et al. |
| 5,322,413 A | 6/1994 | Vescovini et al. |
| 5,326,344 A | 7/1994 | Bramm et al. |
| 5,363,856 A | 11/1994 | Hughes et al. |
| 5,397,349 A | 3/1995 | Kolff et al. |
| 5,399,074 A | 3/1995 | Nose et al. |
| 5,405,251 A | 4/1995 | Sipin |
| 5,441,636 A | 8/1995 | Chevallet et al. |
| 5,443,504 A | 8/1995 | Hill |
| 5,486,192 A | 1/1996 | Walinsky et al. |
| 5,487,727 A | 1/1996 | Snider et al. |
| 5,507,629 A | 4/1996 | Jarvik |
| 5,507,795 A | 4/1996 | Chiang et al. |
| 5,510,267 A | 4/1996 | Marshall |
| 5,512,042 A | 4/1996 | Montoya et al. |
| 5,531,789 A | 7/1996 | Yamazaki et al. |
| 5,628,731 A | 5/1997 | Dodge et al. |
| 5,630,835 A | 5/1997 | Brownlee |
| 5,643,172 A | 7/1997 | Kung et al. |
| 5,643,215 A | 7/1997 | Fuhrman |
| 5,653,696 A | 8/1997 | Shiber |
| 5,662,643 A | 9/1997 | Kung |
| 5,676,526 A | 10/1997 | Kuwana et al. |
| 5,683,231 A | 11/1997 | Nakazawa et al. |
| 5,702,365 A | 12/1997 | King |
| 5,713,730 A | 2/1998 | Nose et al. |
| 5,749,839 A | 5/1998 | Kovacs |
| 5,751,125 A | 5/1998 | Weiss |
| 5,759,148 A | 6/1998 | Sipin |
| 5,766,207 A | 6/1998 | Potter et al. |
| 5,776,096 A | 7/1998 | Fields |
| 5,800,138 A | 9/1998 | Merce Vives |
| 5,800,457 A | 9/1998 | Gelbfish |
| 5,803,720 A | 9/1998 | Ohara et al. |
| 5,814,076 A | 9/1998 | Brownlee |
| 5,814,102 A | 9/1998 | Guldner et al. |
| 5,851,174 A | 12/1998 | Jarvik et al. |
| 5,888,241 A | 3/1999 | Jarvik |
| 5,906,579 A | 5/1999 | Vander Salm et al. |
| 5,910,124 A | 6/1999 | Rubin |
| 5,919,369 A | 7/1999 | Ash |
| 5,941,813 A | 8/1999 | Sievers et al. |
| 5,964,694 A | 10/1999 | Siess et al. |
| 5,984,893 A | 11/1999 | Ward |
| 6,013,058 A | 1/2000 | Prosl et al. |
| 6,022,363 A | 2/2000 | Walker et al. |
| 6,030,336 A | 2/2000 | Franchi |
| 6,042,347 A | 3/2000 | Scholl et al. |
| 6,066,085 A | 5/2000 | Heilman et al. |

(56) References Cited

U.S. PATENT DOCUMENTS

| | | |
|---|---|---|
| 6,066,152 A | 5/2000 | Strauss et al. |
| 6,068,588 A | 5/2000 | Goldowsky |
| 6,071,093 A | 6/2000 | Hart |
| 6,071,258 A | 6/2000 | Dalke et al. |
| 6,082,105 A | 7/2000 | Miyata |
| 6,101,406 A | 8/2000 | Hacker et al. |
| 6,106,509 A | 8/2000 | Loubser |
| 6,113,536 A | 9/2000 | Aboul Hosn et al. |
| 6,117,130 A | 9/2000 | Kung |
| 6,117,390 A | 9/2000 | Corey |
| 6,120,537 A | 9/2000 | Wampler |
| 6,123,659 A | 9/2000 | Le Blanc et al. |
| 6,123,726 A | 9/2000 | Mori et al. |
| 6,129,660 A | 10/2000 | Nakazeki et al. |
| 6,136,025 A | 10/2000 | Barbut et al. |
| 6,139,487 A | 10/2000 | Siess |
| 6,142,752 A | 11/2000 | Akamatsu et al. |
| 6,146,771 A | 11/2000 | Wirt et al. |
| 6,149,683 A | 11/2000 | Lancisi et al. |
| 6,152,704 A | 11/2000 | Aboul Hosn et al. |
| 6,155,969 A | 12/2000 | Schima et al. |
| 6,176,848 B1 | 1/2001 | Rau et al. |
| 6,180,058 B1 | 1/2001 | Lindsay |
| 6,197,055 B1 | 3/2001 | Matthews |
| 6,197,289 B1 | 3/2001 | Wirt et al. |
| 6,210,133 B1 | 4/2001 | Aboul Hosn et al. |
| 6,210,318 B1 | 4/2001 | Lederman |
| 6,228,023 B1 | 5/2001 | Zaslavsky et al. |
| 6,236,883 B1 | 5/2001 | Ciaccio et al. |
| 6,254,359 B1 | 7/2001 | Aber |
| 6,270,831 B2 | 8/2001 | Kumar et al. |
| 6,273,861 B1 | 8/2001 | Bates et al. |
| 6,283,949 B1 | 9/2001 | Roorda |
| 6,287,319 B1 | 9/2001 | Aboul Hosn et al. |
| 6,290,685 B1 | 9/2001 | Insley et al. |
| 6,312,462 B1 | 11/2001 | McDermott et al. |
| 6,314,322 B1 | 11/2001 | Rosenberg |
| 6,319,231 B1 | 11/2001 | Andrulitis |
| 6,361,292 B1 | 3/2002 | Chang et al. |
| 6,361,501 B1 | 3/2002 | Amano et al. |
| 6,364,833 B1 | 4/2002 | Valerio et al. |
| 6,398,715 B1 | 6/2002 | Magovern et al. |
| 6,400,991 B1 | 6/2002 | Kung |
| 6,406,267 B1 | 6/2002 | Mondiere |
| 6,406,422 B1 | 6/2002 | Landesberg |
| 6,419,657 B1 | 7/2002 | Pacetti |
| 6,422,990 B1 | 7/2002 | Prem |
| 6,432,136 B1 | 8/2002 | Weiss et al. |
| 6,443,944 B1 | 9/2002 | Doshi et al. |
| 6,443,983 B1 | 9/2002 | Nagyszalanczy et al. |
| 6,445,956 B1 | 9/2002 | Laird et al. |
| 6,447,265 B1 | 9/2002 | Antaki et al. |
| 6,447,266 B2 | 9/2002 | Antaki et al. |
| 6,447,441 B1 | 9/2002 | Yu et al. |
| 6,497,680 B1 | 12/2002 | Holst et al. |
| 6,503,224 B1 | 1/2003 | Forman et al. |
| 6,503,450 B1 | 1/2003 | Afzal et al. |
| 6,508,787 B2 | 1/2003 | Erbel et al. |
| 6,508,806 B1 | 1/2003 | Hoste |
| 6,527,699 B1 | 3/2003 | Goldowsky |
| 6,533,716 B1 | 3/2003 | Schmitz-Rode et al. |
| 6,533,724 B2 | 3/2003 | McNair |
| 6,537,315 B2 | 3/2003 | Yamazaki et al. |
| 6,540,658 B1 | 4/2003 | Fasciano et al. |
| 6,540,659 B1 | 4/2003 | Milbocker |
| 6,544,543 B1 | 4/2003 | Mandrusov et al. |
| 6,547,716 B1 | 4/2003 | Milbocker |
| 6,562,022 B2 | 5/2003 | Hoste et al. |
| 6,572,529 B2 | 6/2003 | Wilk |
| 6,572,534 B1 | 6/2003 | Milbocker et al. |
| 6,595,943 B1 | 7/2003 | Burbank |
| 6,602,182 B1 | 8/2003 | Milbocker |
| 6,616,596 B1 | 9/2003 | Milbocker |
| 6,620,120 B2 | 9/2003 | Landry et al. |
| 6,623,420 B2 | 9/2003 | Reich et al. |
| 6,626,821 B1 | 9/2003 | Kung et al. |
| 6,626,889 B1 | 9/2003 | Simpson et al. |
| 6,626,935 B1 | 9/2003 | Ainsworth et al. |
| 6,632,215 B1 | 10/2003 | Lemelson |
| 6,635,083 B1 | 10/2003 | Cheng et al. |
| 6,656,220 B1 | 12/2003 | Gomez et al. |
| 6,669,624 B2 | 12/2003 | Frazier |
| 6,669,662 B1 | 12/2003 | Webler |
| 6,676,679 B1 | 1/2004 | Mueller et al. |
| 6,688,869 B1 | 2/2004 | Simonds |
| 6,699,231 B1 | 3/2004 | Sterman et al. |
| 6,709,382 B1 | 3/2004 | Horner |
| 6,730,102 B1 | 5/2004 | Burdulis et al. |
| 6,746,416 B2 | 6/2004 | Hubbard et al. |
| 6,749,615 B2 | 6/2004 | Burdulis et al. |
| 6,769,871 B2 | 8/2004 | Yamazaki |
| 6,790,171 B1 | 9/2004 | Gründeman et al. |
| 6,811,749 B2 | 11/2004 | Lindsay |
| 6,821,295 B1 | 11/2004 | Farrar |
| 6,837,890 B1 | 1/2005 | Chludzinski et al. |
| 6,846,296 B1 | 1/2005 | Milbocker et al. |
| 6,866,650 B2 | 3/2005 | Stevens et al. |
| 6,879,126 B2 | 4/2005 | Paden et al. |
| 6,884,210 B2 | 4/2005 | Nose et al. |
| 6,908,280 B2 | 6/2005 | Yamazaki |
| 6,908,435 B1 | 6/2005 | Mueller et al. |
| 6,929,632 B2 | 8/2005 | Nita et al. |
| 6,929,660 B1 | 8/2005 | Ainsworth et al. |
| 6,942,672 B2 | 9/2005 | Heilman et al. |
| 6,945,978 B1 | 9/2005 | Hyde |
| 6,949,066 B2 | 9/2005 | Bearnson et al. |
| 6,969,345 B2 | 11/2005 | Jassawalla et al. |
| 6,981,942 B2 | 1/2006 | Khaw et al. |
| 7,022,100 B1 | 4/2006 | Aboul Hosn et al. |
| 7,025,742 B2 | 4/2006 | Rubenstein et al. |
| 7,027,875 B2 | 4/2006 | Siess et al. |
| 7,029,483 B2 | 4/2006 | Schwartz |
| 7,037,253 B2 | 5/2006 | French et al. |
| 7,048,747 B2 | 5/2006 | Arcia et al. |
| 7,074,018 B2 | 7/2006 | Chang |
| 7,108,652 B2 | 9/2006 | Stenberg et al. |
| 7,118,525 B2 | 10/2006 | Coleman et al. |
| 7,122,151 B2 | 10/2006 | Reeder et al. |
| 7,125,376 B2 | 10/2006 | Viole et al. |
| 7,126,310 B1 | 10/2006 | Barron |
| 7,150,711 B2 | 12/2006 | Nüsser et al. |
| 7,155,291 B2 | 12/2006 | Zarinetchi et al. |
| 7,172,551 B2 | 2/2007 | Leasure |
| 7,189,260 B2 | 3/2007 | Horvath et al. |
| 7,229,258 B2 | 6/2007 | Wood et al. |
| 7,229,402 B2 | 6/2007 | Diaz et al. |
| 7,238,151 B2 | 7/2007 | Frazier |
| 7,244,224 B2 | 7/2007 | Tsukahara et al. |
| 7,247,166 B2 | 7/2007 | Pienknagura |
| 7,303,581 B2 | 12/2007 | Peraita |
| 7,331,972 B1 | 2/2008 | Cox |
| 7,331,987 B1 | 2/2008 | Cox |
| 7,361,726 B2 | 4/2008 | Pacetti et al. |
| 7,377,927 B2 | 5/2008 | Burdulis et al. |
| 7,392,077 B2 | 6/2008 | Mueller et al. |
| 7,393,181 B2 | 7/2008 | McBride et al. |
| 7,396,327 B2 | 7/2008 | Morello |
| 7,479,102 B2 | 1/2009 | Jarvik |
| 7,520,850 B2 | 4/2009 | Brockway |
| 7,524,277 B1 | 4/2009 | Wang et al. |
| 7,541,000 B2 | 6/2009 | Stringer et al. |
| 7,544,160 B2 | 6/2009 | Gross |
| 7,547,391 B2 | 6/2009 | Petrie |
| 7,585,322 B2 | 9/2009 | Azzolina |
| 7,588,530 B2 | 9/2009 | Heilman et al. |
| 7,588,549 B2 | 9/2009 | Eccleston |
| 7,591,199 B2 | 9/2009 | Weldon et al. |
| 7,611,478 B2 | 11/2009 | Lucke et al. |
| 7,628,756 B2 | 12/2009 | Hacker et al. |
| 7,713,259 B2 | 5/2010 | Gosiengfiao et al. |
| RE41,394 E | 6/2010 | Bugge et al. |
| 7,736,296 B2 | 6/2010 | Siess et al. |
| 7,736,375 B2 | 6/2010 | Crow |
| 7,758,492 B2 | 7/2010 | Weatherbee |

(56) References Cited

U.S. PATENT DOCUMENTS

| | | |
|---|---|---|
| 7,776,991 B2 | 8/2010 | Pacetti et al. |
| 7,780,628 B1 | 8/2010 | Keren et al. |
| 7,794,419 B2 | 9/2010 | Paolini et al. |
| 7,794,743 B2 | 9/2010 | Simhambhatla et al. |
| 7,819,834 B2 | 10/2010 | Paul |
| 7,828,710 B2 | 11/2010 | Shifflette |
| 7,833,239 B2 | 11/2010 | Nash |
| 7,841,976 B2 | 11/2010 | McBride et al. |
| 7,850,594 B2 | 12/2010 | Sutton et al. |
| 7,862,501 B2 | 1/2011 | Woodard |
| 7,878,967 B1 | 2/2011 | Khanal |
| 7,914,436 B1 | 3/2011 | Kung |
| 7,922,657 B2 | 4/2011 | Gillinov et al. |
| 7,942,804 B2 | 5/2011 | Khaw |
| 7,963,905 B2 | 6/2011 | Salmonsen et al. |
| 7,972,122 B2 | 7/2011 | LaRose et al. |
| 7,972,291 B2 | 7/2011 | Ibragimov |
| 7,985,442 B2 | 7/2011 | Gong |
| 7,988,728 B2 | 8/2011 | Ayre |
| 7,993,259 B2 | 8/2011 | Kang et al. |
| 7,993,260 B2 | 8/2011 | Boiling |
| 7,993,358 B2 | 8/2011 | O'Brien |
| 7,998,054 B2 | 8/2011 | Bolling |
| 7,998,190 B2 | 8/2011 | Gharib et al. |
| 8,012,079 B2 | 9/2011 | Delgado |
| 8,012,194 B2 | 9/2011 | Edwin et al. |
| 8,012,508 B2 | 9/2011 | Ludwig |
| 8,029,728 B2 | 10/2011 | Lindsay |
| 8,034,098 B1 | 10/2011 | Callas et al. |
| 8,048,442 B1 | 11/2011 | Hossainy et al. |
| 8,052,749 B2 | 11/2011 | Salahleh et al. |
| 8,070,742 B2 | 12/2011 | Woo |
| 8,070,804 B2 | 12/2011 | Hyde et al. |
| 8,075,472 B2 | 12/2011 | Zilbershlag et al. |
| 8,079,948 B2 | 12/2011 | Shifflette |
| 8,083,726 B1 | 12/2011 | Wang |
| 8,123,669 B2 | 2/2012 | Siess et al. |
| 8,123,674 B2 | 2/2012 | Kuyava |
| 8,133,272 B2 | 3/2012 | Hyde |
| RE43,299 E | 4/2012 | Siess |
| 8,152,035 B2 | 4/2012 | Earl |
| 8,152,845 B2 | 4/2012 | Bourque |
| 8,153,083 B2 | 4/2012 | Briggs |
| 8,157,719 B1 | 4/2012 | Ainsworth |
| 8,157,721 B2 | 4/2012 | Sugiura |
| 8,157,758 B2 | 4/2012 | Pecor et al. |
| 8,158,062 B2 | 4/2012 | Dykes et al. |
| 8,162,021 B2 | 4/2012 | Tomasetti et al. |
| 8,167,589 B2 | 5/2012 | Hidaka et al. |
| 8,172,783 B1 | 5/2012 | Ray |
| 8,177,750 B2 | 5/2012 | Steinbach et al. |
| 8,187,324 B2 | 5/2012 | Webler et al. |
| 8,197,463 B2 | 6/2012 | Intoccia |
| 8,210,829 B2 | 7/2012 | Horvath et al. |
| 8,241,199 B2 | 8/2012 | Maschke |
| 8,257,258 B2 | 9/2012 | Zocchi |
| 8,257,375 B2 | 9/2012 | Maschke |
| 8,266,943 B2 | 9/2012 | Miyakoshi et al. |
| D669,585 S | 10/2012 | Bourque |
| 8,277,476 B2 | 10/2012 | Taylor et al. |
| 8,282,359 B2 | 10/2012 | Ayre et al. |
| 8,292,908 B2 | 10/2012 | Nieman et al. |
| D671,646 S | 11/2012 | Bourque et al. |
| 8,303,482 B2 | 11/2012 | Schima et al. |
| 8,323,173 B2 | 12/2012 | Benkowski et al. |
| 8,328,750 B2 | 12/2012 | Peters et al. |
| 8,329,114 B2 | 12/2012 | Temple |
| 8,329,158 B2 | 12/2012 | Hossainy et al. |
| 8,366,599 B2 | 2/2013 | Tansley et al. |
| 8,372,137 B2 | 2/2013 | Pienknagura |
| 8,377,033 B2 | 2/2013 | Basu et al. |
| 8,377,083 B2 | 2/2013 | Mauch et al. |
| 8,382,695 B1 | 2/2013 | Patel |
| 8,388,649 B2 | 3/2013 | Woodard |
| 8,419,609 B2 | 4/2013 | Shambaugh et al. |
| 8,419,944 B2 | 4/2013 | Alkanhal |
| 8,439,909 B2 | 5/2013 | Wang et al. |
| 8,449,444 B2 | 5/2013 | Poirier |
| 8,454,683 B2 | 6/2013 | Rafiee et al. |
| 8,485,961 B2 | 7/2013 | Campbell et al. |
| 8,496,874 B2 | 7/2013 | Gellman et al. |
| 8,500,620 B2 | 8/2013 | Lu et al. |
| 8,506,471 B2 | 8/2013 | Bourque |
| 8,535,211 B2 | 9/2013 | Campbell et al. |
| 8,535,212 B2 | 9/2013 | Robert |
| 8,538,515 B2 | 9/2013 | Atanasoska et al. |
| 8,545,382 B2 | 10/2013 | Suzuki et al. |
| 8,545,447 B2 | 10/2013 | Demarais et al. |
| 8,562,509 B2 | 10/2013 | Bates |
| 8,568,289 B2 | 10/2013 | Mazur |
| 8,579,858 B2 | 11/2013 | Reitan et al. |
| 8,579,967 B2 | 11/2013 | Webler et al. |
| 8,585,572 B2 | 11/2013 | Mehmanesh |
| 8,586,527 B2 | 11/2013 | Singh |
| 8,591,393 B2 | 11/2013 | Walters et al. |
| 8,591,394 B2 | 11/2013 | Peters et al. |
| 8,591,449 B2 | 11/2013 | Hudson |
| 8,591,538 B2 | 11/2013 | Gellman |
| 8,591,539 B2 | 11/2013 | Gellman |
| D696,769 S | 12/2013 | Schenck et al. |
| 8,597,170 B2 | 12/2013 | Walters et al. |
| 8,608,661 B1 | 12/2013 | Mandrusov et al. |
| 8,613,777 B2 | 12/2013 | Siess et al. |
| 8,613,892 B2 | 12/2013 | Stafford |
| 8,617,239 B2 | 12/2013 | Reitan |
| 8,631,680 B2 | 1/2014 | Fleischli et al. |
| 8,632,449 B2 | 1/2014 | Masuzawa et al. |
| 8,641,594 B2 | 2/2014 | LaRose et al. |
| 8,657,871 B2 | 2/2014 | Limon |
| 8,657,875 B2 | 2/2014 | Kung et al. |
| 8,668,473 B2 | 3/2014 | LaRose et al. |
| 8,684,903 B2 | 4/2014 | Nour |
| 8,690,749 B1 | 4/2014 | Nunez |
| 8,690,823 B2 | 4/2014 | Yribarren et al. |
| 8,697,058 B2 | 4/2014 | Basu et al. |
| 8,708,948 B2 | 4/2014 | Consigny et al. |
| 8,715,151 B2 | 5/2014 | Poirier |
| 8,715,156 B2 | 5/2014 | Jayaraman |
| 8,715,707 B2 | 5/2014 | Hossainy et al. |
| 8,721,516 B2 | 5/2014 | Scheckel |
| 8,721,517 B2 | 5/2014 | Zeng et al. |
| 8,734,331 B2 | 5/2014 | Evans et al. |
| 8,734,508 B2 | 5/2014 | Hastings et al. |
| 8,739,727 B2 | 6/2014 | Austin et al. |
| 8,740,920 B2 | 6/2014 | Goldfarb et al. |
| 8,741,287 B2 | 6/2014 | Brophy et al. |
| 8,758,388 B2 | 6/2014 | Pah |
| 8,766,788 B2 | 7/2014 | D'Ambrosio |
| 8,777,832 B1 | 7/2014 | Wang et al. |
| 8,790,399 B2 | 7/2014 | Frazier et al. |
| 8,795,576 B2 | 8/2014 | Tao et al. |
| 8,814,543 B2 | 8/2014 | Liebing |
| 8,814,776 B2 | 8/2014 | Hastie et al. |
| 8,814,933 B2 | 8/2014 | Siess |
| 8,815,274 B2 | 8/2014 | DesNoyer et al. |
| 8,821,366 B2 | 9/2014 | Farnan et al. |
| 8,837,096 B2 | 9/2014 | Seebruch |
| 8,840,539 B2 | 9/2014 | Zilbershlag |
| 8,840,566 B2 | 9/2014 | Seibel et al. |
| 8,849,398 B2 | 9/2014 | Evans |
| 8,862,232 B2 | 10/2014 | Zarinetchi et al. |
| 8,864,642 B2 | 10/2014 | Scheckel |
| 8,876,685 B2 | 11/2014 | Crosby et al. |
| 8,882,744 B2 | 11/2014 | Dormanen et al. |
| 8,888,675 B2 | 11/2014 | Stankus et al. |
| 8,894,387 B2 | 11/2014 | White |
| 8,894,561 B2 | 11/2014 | Callaway et al. |
| 8,897,873 B2 | 11/2014 | Schima et al. |
| 8,900,060 B2 | 12/2014 | Liebing |
| 8,905,910 B2 | 12/2014 | Reichenbach et al. |
| 8,927,700 B2 | 1/2015 | McCauley et al. |
| 8,932,141 B2 | 1/2015 | Liebing |
| 8,932,197 B2 | 1/2015 | Gregoric et al. |
| 8,942,828 B1 | 1/2015 | Schecter |

(56) References Cited

U.S. PATENT DOCUMENTS

| | | |
|---|---|---|
| 8,944,748 B2 | 2/2015 | Liebing |
| 8,945,159 B2 | 2/2015 | Nussbaum |
| 8,956,402 B2 | 2/2015 | Cohn |
| 8,961,387 B2 | 2/2015 | Duncan |
| 8,961,466 B2 | 2/2015 | Steinbach |
| 8,971,980 B2 | 3/2015 | Mace et al. |
| 8,974,519 B2 | 3/2015 | Gennrich et al. |
| 8,992,406 B2 | 3/2015 | Corbett |
| 8,997,349 B2 | 4/2015 | Mori et al. |
| 9,002,468 B2 | 4/2015 | Shea et al. |
| 9,023,010 B2 | 5/2015 | Chiu et al. |
| 9,028,216 B2 | 5/2015 | Schumacher et al. |
| 9,028,392 B2 | 5/2015 | Shifflette |
| 9,028,859 B2 | 5/2015 | Hossainy et al. |
| 9,033,863 B2 | 5/2015 | Jarvik |
| 9,033,909 B2 | 5/2015 | Aihara |
| 9,039,595 B2 | 5/2015 | Ayre et al. |
| 9,044,236 B2 | 6/2015 | Nguyen et al. |
| 9,056,159 B2 | 6/2015 | Medvedev et al. |
| 9,066,992 B2 | 6/2015 | Stankus et al. |
| 9,067,005 B2 | 6/2015 | Ozaki et al. |
| 9,067,006 B2 | 6/2015 | Toellner |
| 9,072,825 B2 | 7/2015 | Pfeffer et al. |
| 9,078,692 B2 | 7/2015 | Shturman et al. |
| 9,089,329 B2 | 7/2015 | Hoarau et al. |
| 9,089,634 B2 | 7/2015 | Schumacher et al. |
| 9,089,635 B2 | 7/2015 | Reichenbach et al. |
| 9,089,670 B2 | 7/2015 | Scheckel |
| 9,095,428 B2 | 8/2015 | Kabir et al. |
| 9,096,703 B2 | 8/2015 | Li et al. |
| 9,101,302 B2 | 8/2015 | Mace et al. |
| 9,125,977 B2 | 9/2015 | Nishimura et al. |
| 9,127,680 B2 | 9/2015 | Yanai et al. |
| 9,138,516 B2 | 9/2015 | Vischer et al. |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,168,361 B2 | 10/2015 | Ehrenreich et al. |
| 9,180,227 B2 | 11/2015 | Ludwig et al. |
| 9,180,235 B2 | 11/2015 | Forsell |
| 9,192,705 B2 | 11/2015 | Yanai et al. |
| 9,199,020 B2 | 12/2015 | Siess |
| 9,217,442 B2 | 12/2015 | Wiessler et al. |
| D746,975 S | 1/2016 | Schenck et al. |
| 9,227,002 B1 | 1/2016 | Giridharan et al. |
| 9,239,049 B2 | 1/2016 | Jarnagin et al. |
| 9,265,870 B2 | 2/2016 | Reichenbach et al. |
| 9,278,189 B2 | 3/2016 | Corbett |
| 9,283,314 B2 | 3/2016 | Prasad et al. |
| 9,291,591 B2 | 3/2016 | Simmons et al. |
| 9,295,550 B2 | 3/2016 | Nguyen et al. |
| 9,295,767 B2 | 3/2016 | Schmid et al. |
| 9,308,302 B2 | 4/2016 | Zeng |
| 9,308,304 B2 | 4/2016 | Peters et al. |
| 9,314,558 B2 | 4/2016 | Er |
| 9,314,559 B2 | 4/2016 | Smith |
| 9,328,741 B2 | 5/2016 | Liebing |
| 9,333,284 B2 | 5/2016 | Thompson et al. |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,255 B2 | 6/2016 | Weber |
| 9,364,592 B2 | 6/2016 | McBride et al. |
| 9,370,613 B2 | 6/2016 | Hsu et al. |
| 9,375,445 B2 | 6/2016 | Hossainy et al. |
| 9,381,285 B2 | 7/2016 | Ozaki |
| 9,387,284 B2 | 7/2016 | Heilman et al. |
| 9,409,012 B2 | 8/2016 | Eidenschink et al. |
| 9,416,783 B2 | 8/2016 | Schumacher et al. |
| 9,416,791 B2 | 8/2016 | Toellner |
| 9,421,311 B2 | 8/2016 | Tanner et al. |
| 9,433,713 B2 | 9/2016 | Corbett et al. |
| 9,435,450 B2 | 9/2016 | Muennich |
| 9,446,179 B2 | 9/2016 | Keenan et al. |
| 9,452,249 B2 | 9/2016 | Kearsley et al. |
| 9,474,840 B2 | 10/2016 | Siess |
| 9,486,565 B2 | 11/2016 | Göllner et al. |
| 9,492,601 B2 | 11/2016 | Casas et al. |
| 9,504,491 B2 | 11/2016 | Callas et al. |
| 9,511,179 B2 | 12/2016 | Casas et al. |
| 9,522,257 B2 | 12/2016 | Webler |
| 9,526,818 B2 | 12/2016 | Kearsley et al. |
| 9,533,084 B2 | 1/2017 | Siess et al. |
| 9,533,085 B2 | 1/2017 | Hanna |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,555,177 B2 | 1/2017 | Curtis et al. |
| 9,556,873 B2 | 1/2017 | Yanai et al. |
| 9,561,309 B2 | 2/2017 | Glauser et al. |
| 9,561,313 B2 | 2/2017 | Taskin |
| 9,592,328 B2 | 3/2017 | Jeevanandam et al. |
| 9,603,983 B2 | 3/2017 | Roehn et al. |
| 9,603,984 B2 | 3/2017 | Romero et al. |
| 9,611,743 B2 | 4/2017 | Toellner et al. |
| 9,612,182 B2 | 4/2017 | Olde et al. |
| 9,616,157 B2 | 4/2017 | Akdis |
| 9,616,159 B2 | 4/2017 | Anderson et al. |
| 9,623,163 B1 | 4/2017 | Fischi |
| 9,631,754 B2 | 4/2017 | Richardson et al. |
| 9,642,984 B2 | 5/2017 | Schumacher et al. |
| 9,656,010 B2 | 5/2017 | Burke |
| 9,656,030 B1 | 5/2017 | Webler et al. |
| 9,662,211 B2 | 5/2017 | Hodson et al. |
| 9,669,141 B2 | 6/2017 | Parker et al. |
| 9,669,142 B2 | 6/2017 | Spanier et al. |
| 9,669,143 B2 | 6/2017 | Guerrero |
| 9,675,450 B2 | 6/2017 | Straka et al. |
| 9,675,738 B2 | 6/2017 | Tanner et al. |
| 9,675,739 B2 | 6/2017 | Tanner et al. |
| 9,675,742 B2 | 6/2017 | Casas et al. |
| 9,687,596 B2 | 6/2017 | Poirier |
| 9,687,630 B2 | 6/2017 | Basu et al. |
| 9,700,659 B2 | 7/2017 | Kantrowitz et al. |
| 9,713,662 B2 | 7/2017 | Rosenberg et al. |
| 9,713,663 B2 | 7/2017 | Medvedev et al. |
| 9,715,839 B2 | 7/2017 | Pybus et al. |
| 9,717,615 B2 | 8/2017 | Grandt |
| 9,717,832 B2 | 8/2017 | Taskin et al. |
| 9,717,839 B2 | 8/2017 | Hashimoto |
| 9,726,195 B2 | 8/2017 | Cecere et al. |
| 9,731,058 B2 | 8/2017 | Siebenhaar et al. |
| 9,731,101 B2 | 8/2017 | Bertrand et al. |
| 9,737,361 B2 | 8/2017 | Magana et al. |
| 9,737,651 B2 | 8/2017 | Wampler |
| 9,744,280 B2 | 8/2017 | Schade et al. |
| 9,744,287 B2 | 8/2017 | Bulent et al. |
| 9,750,859 B2 | 9/2017 | Bulent et al. |
| 9,757,502 B2 | 9/2017 | Burke et al. |
| 9,770,202 B2 | 9/2017 | Ralston et al. |
| 9,770,543 B2 | 9/2017 | Tanner et al. |
| 9,771,801 B2 | 9/2017 | Schumacher et al. |
| 9,775,930 B2 | 10/2017 | Michal et al. |
| 9,782,279 B2 | 10/2017 | Kassab |
| 9,782,527 B2 | 10/2017 | Thomas et al. |
| 9,795,780 B2 | 10/2017 | Serna et al. |
| 9,801,987 B2 | 10/2017 | Farnan et al. |
| 9,801,992 B2 | 10/2017 | Giordano et al. |
| 9,821,098 B2 | 11/2017 | Horvath et al. |
| 9,821,146 B2 | 11/2017 | Tao et al. |
| 9,827,356 B2 | 11/2017 | Muller et al. |
| 9,833,314 B2 | 12/2017 | Corbett |
| 9,833,550 B2 | 12/2017 | Siess |
| 9,833,551 B2 | 12/2017 | Criscione et al. |
| 9,839,734 B1 | 12/2017 | Menon et al. |
| 9,844,618 B2 | 12/2017 | Muller-Spanka et al. |
| 9,850,906 B2 | 12/2017 | Ozaki et al. |
| 9,855,437 B2 | 1/2018 | Nguyen et al. |
| 9,861,504 B2 | 1/2018 | Abunassar et al. |
| 9,861,731 B2 | 1/2018 | Tamburino |
| 9,872,948 B2 | 1/2018 | Siess |
| 9,878,087 B2 | 1/2018 | Richardson et al. |

(56) References Cited

U.S. PATENT DOCUMENTS

| | | |
|---|---|---|
| 9,878,169 B2 | 1/2018 | Hossainy |
| 9,889,242 B2 | 2/2018 | Pfeffer et al. |
| 9,895,244 B2 | 2/2018 | Papp et al. |
| 9,895,475 B2 | 2/2018 | Toellner et al. |
| 9,907,890 B2 | 3/2018 | Muller |
| 9,907,892 B2 | 3/2018 | Broen et al. |
| 9,913,937 B2 | 3/2018 | Schwammenthal et al. |
| 9,918,822 B2 | 3/2018 | Abunassar et al. |
| 9,919,085 B2 | 3/2018 | Throckmorton et al. |
| 9,919,088 B2 | 3/2018 | Bonde et al. |
| 9,919,089 B2 | 3/2018 | Garrigue |
| 9,950,101 B2 | 4/2018 | Smith et al. |
| 9,956,410 B2 | 5/2018 | Deem et al. |
| 9,962,258 B2 | 5/2018 | Seguin et al. |
| 9,974,893 B2 | 5/2018 | Toellner |
| 9,974,894 B2 | 5/2018 | Morello |
| 9,981,078 B2 | 5/2018 | Jin et al. |
| 9,985,374 B2 | 5/2018 | Hodges |
| 9,987,407 B2 | 6/2018 | Grant et al. |
| 10,010,273 B2 | 7/2018 | Sloan et al. |
| 10,022,499 B2 | 7/2018 | Galasso |
| 10,028,835 B2 | 7/2018 | Kermode et al. |
| 10,029,037 B2 | 7/2018 | Muller et al. |
| 10,029,038 B2 | 7/2018 | Hodges |
| 10,029,039 B2 | 7/2018 | Dague et al. |
| 10,031,124 B2 | 7/2018 | Galasso |
| 10,034,972 B2 | 7/2018 | Wampler et al. |
| 10,039,873 B2 | 8/2018 | Siegenthaler |
| 10,046,146 B2 | 8/2018 | Manderfeld et al. |
| 10,058,349 B2 | 8/2018 | Gunderson et al. |
| 10,058,641 B2 | 8/2018 | Mollison et al. |
| 10,058,652 B2 | 8/2018 | Tsoukalis |
| 10,058,653 B2 | 8/2018 | Wang et al. |
| 10,077,777 B2 | 9/2018 | Horvath et al. |
| 10,080,828 B2 | 9/2018 | Wiesener et al. |
| 10,080,834 B2 | 9/2018 | Federspiel et al. |
| 10,080,871 B2 | 9/2018 | Schumacher et al. |
| 10,569,005 B2 | 2/2020 | Solem et al. |
| 10,722,631 B2 | 7/2020 | Salahieh et al. |
| 10,881,770 B2 | 1/2021 | Tuval et al. |
| 11,123,538 B2 | 9/2021 | Epple et al. |
| 2001/0003802 A1 | 6/2001 | Vitale |
| 2001/0023369 A1 | 9/2001 | Chobotov |
| 2001/0053928 A1 | 12/2001 | Edelman et al. |
| 2002/0057989 A1 | 5/2002 | Afzal et al. |
| 2002/0058971 A1 | 5/2002 | Zarinetchi et al. |
| 2002/0068848 A1 | 6/2002 | Zadini et al. |
| 2002/0072679 A1 | 6/2002 | Schock et al. |
| 2002/0128709 A1 | 9/2002 | Pless |
| 2002/0147495 A1 | 10/2002 | Petroff |
| 2003/0069465 A1 | 4/2003 | Benkowski et al. |
| 2003/0088151 A1 | 5/2003 | Kung et al. |
| 2003/0131995 A1 | 7/2003 | de Rouffignac et al. |
| 2003/0155111 A1 | 8/2003 | Vinegar et al. |
| 2003/0173081 A1 | 9/2003 | Vinegar et al. |
| 2003/0173082 A1 | 9/2003 | Vinegar et al. |
| 2003/0173085 A1 | 9/2003 | Vinegar et al. |
| 2003/0178191 A1 | 9/2003 | Maher et al. |
| 2003/0209348 A1 | 11/2003 | Ward et al. |
| 2003/0217957 A1 | 11/2003 | Bowman et al. |
| 2004/0024285 A1 | 2/2004 | Muckter |
| 2004/0040715 A1 | 3/2004 | Wellington et al. |
| 2004/0097782 A1 | 5/2004 | Korakianitis et al. |
| 2004/0097783 A1 | 5/2004 | Peters et al. |
| 2004/0228724 A1 | 11/2004 | Capone et al. |
| 2004/0249363 A1 | 12/2004 | Burke et al. |
| 2005/0010077 A1 | 1/2005 | Calderon |
| 2005/0043805 A1 | 2/2005 | Chudik |
| 2005/0049696 A1 | 3/2005 | Siess et al. |
| 2005/0060036 A1 | 3/2005 | Schultz et al. |
| 2005/0113632 A1 | 5/2005 | Ortiz et al. |
| 2005/0119599 A1 | 6/2005 | Kanz et al. |
| 2005/0187616 A1 | 8/2005 | Realyvasquez |
| 2005/0209617 A1 | 9/2005 | Koven et al. |
| 2005/0220636 A1 | 10/2005 | Henein et al. |
| 2005/0254976 A1 | 11/2005 | Carrier et al. |
| 2005/0256540 A1 | 11/2005 | Silver et al. |
| 2006/0111641 A1 | 5/2006 | Manera et al. |
| 2006/0116700 A1 | 6/2006 | Crow |
| 2006/0129082 A1 | 6/2006 | Rozga |
| 2006/0155158 A1 | 7/2006 | Hosn |
| 2006/0177343 A1 | 8/2006 | Brian et al. |
| 2006/0195098 A1 | 8/2006 | Schumacher |
| 2006/0257355 A1 | 11/2006 | Stewart et al. |
| 2006/0293664 A1 | 12/2006 | Schumacher |
| 2007/0106274 A1 | 5/2007 | Ayre et al. |
| 2007/0167091 A1 | 7/2007 | Schumacher |
| 2007/0203453 A1 | 8/2007 | Mori et al. |
| 2007/0213690 A1 | 9/2007 | Phillips et al. |
| 2007/0253842 A1 | 11/2007 | Horvath et al. |
| 2007/0265673 A1 | 11/2007 | Ransbury et al. |
| 2007/0270633 A1 | 11/2007 | Cook et al. |
| 2007/0299314 A1 | 12/2007 | Bertolero et al. |
| 2008/0045779 A1 | 2/2008 | Rinaldi et al. |
| 2008/0065014 A1 | 3/2008 | Von Oepen et al. |
| 2008/0076101 A1 | 3/2008 | Hyde et al. |
| 2008/0097273 A1 | 4/2008 | Levin et al. |
| 2008/0097562 A1 | 4/2008 | Tan |
| 2008/0119421 A1 | 5/2008 | Tuszynski et al. |
| 2008/0132748 A1 | 6/2008 | Shifflette |
| 2008/0132749 A1 | 6/2008 | Hegde et al. |
| 2008/0167711 A1 | 7/2008 | Roorda |
| 2008/0188923 A1 | 8/2008 | Chu |
| 2008/0200750 A1 | 8/2008 | James |
| 2008/0208329 A1 | 8/2008 | Bishop et al. |
| 2008/0228026 A1 | 9/2008 | Manera et al. |
| 2008/0240947 A1 | 10/2008 | Allaire et al. |
| 2008/0243030 A1 | 10/2008 | Seibel et al. |
| 2008/0275295 A1 | 11/2008 | Gertner |
| 2008/0275354 A1 | 11/2008 | Thuramalla et al. |
| 2008/0296433 A1 | 12/2008 | Brenner et al. |
| 2008/0300677 A1 | 12/2008 | Schreyer |
| 2009/0012460 A1 | 1/2009 | Steck et al. |
| 2009/0061072 A1 | 3/2009 | Isch et al. |
| 2009/0063402 A1 | 3/2009 | Hayter |
| 2009/0082723 A1 | 3/2009 | Krogh et al. |
| 2009/0143635 A1 | 6/2009 | Benkowski et al. |
| 2009/0171448 A1 | 7/2009 | Eli |
| 2009/0177028 A1 | 7/2009 | White |
| 2009/0182307 A1 | 7/2009 | Yap et al. |
| 2009/0188964 A1 | 7/2009 | Orlov |
| 2009/0259089 A1 | 10/2009 | Gelbart et al. |
| 2010/0016703 A1 | 1/2010 | Batkin et al. |
| 2010/0022943 A1 | 1/2010 | Mauch et al. |
| 2010/0042037 A1 | 2/2010 | Felt et al. |
| 2010/0076380 A1 | 3/2010 | Hui |
| 2010/0084326 A1 | 4/2010 | Takesawa |
| 2010/0087742 A1 | 4/2010 | Bishop et al. |
| 2010/0105978 A1 | 4/2010 | Matsui et al. |
| 2010/0152523 A1 | 6/2010 | MacDonald et al. |
| 2010/0152525 A1 | 6/2010 | Weizman et al. |
| 2010/0152526 A1 | 6/2010 | Pacella et al. |
| 2010/0160751 A1 | 6/2010 | Hete et al. |
| 2010/0185220 A1 | 7/2010 | Naghavi et al. |
| 2010/0222635 A1 | 9/2010 | Poirier |
| 2010/0222878 A1 | 9/2010 | Poirier |
| 2010/0249489 A1 | 9/2010 | Jarvik |
| 2011/0098548 A1 | 4/2011 | Budiman et al. |
| 2011/0106115 A1 | 5/2011 | Haselby et al. |
| 2011/0106120 A1 | 5/2011 | Haselby et al. |
| 2011/0178596 A1 | 7/2011 | Hauck et al. |
| 2011/0224655 A1 | 9/2011 | Asirvatham et al. |
| 2011/0301625 A1 | 12/2011 | Mauch et al. |
| 2011/0304240 A1 | 12/2011 | Meitav et al. |
| 2012/0022316 A1 | 1/2012 | Aboul-Hosn et al. |
| 2012/0028908 A1 | 2/2012 | Viswanath |
| 2012/0039711 A1 | 2/2012 | Roehn |
| 2012/0109060 A1 | 5/2012 | Kick et al. |
| 2012/0165641 A1 | 6/2012 | Burnett et al. |
| 2012/0179184 A1 | 7/2012 | Orlov |
| 2012/0184803 A1 | 7/2012 | Simon et al. |
| 2012/0190918 A1 | 7/2012 | Oepen et al. |
| 2012/0239139 A1 | 9/2012 | Wnendt et al. |
| 2012/0252709 A1 | 10/2012 | Felts et al. |

(56) References Cited

U.S. PATENT DOCUMENTS

| | | |
|---|---|---|
| 2012/0289928 A1 | 11/2012 | Wright et al. |
| 2012/0302458 A1 | 11/2012 | Adamczyk et al. |
| 2012/0330683 A1 | 12/2012 | Ledwidge et al. |
| 2013/0023373 A1 | 1/2013 | Janek |
| 2013/0040407 A1 | 2/2013 | Brophy et al. |
| 2013/0053693 A1 | 2/2013 | Breznock et al. |
| 2013/0144144 A1 | 6/2013 | Laster et al. |
| 2013/0211489 A1 | 8/2013 | Makower et al. |
| 2013/0233798 A1 | 9/2013 | Wiktor et al. |
| 2013/0245360 A1 | 9/2013 | Schumacher |
| 2013/0267892 A1 | 10/2013 | Woolford |
| 2013/0281761 A1 | 10/2013 | Kapur |
| 2013/0310845 A1 | 11/2013 | Thor et al. |
| 2013/0317604 A1 | 11/2013 | Min et al. |
| 2013/0344047 A1 | 12/2013 | Pacetti et al. |
| 2014/0017200 A1 | 1/2014 | Michal et al. |
| 2014/0039465 A1 | 2/2014 | Schulz et al. |
| 2014/0039603 A1 | 2/2014 | Wang |
| 2014/0051908 A1 | 2/2014 | Khanal et al. |
| 2014/0058190 A1 | 2/2014 | Gohean et al. |
| 2014/0066693 A1 | 3/2014 | Goldfarb et al. |
| 2014/0128659 A1 | 5/2014 | Heuring et al. |
| 2014/0128795 A1 | 5/2014 | Keren et al. |
| 2014/0163664 A1 | 6/2014 | Goldsmith |
| 2014/0190523 A1 | 7/2014 | Garvey et al. |
| 2014/0194678 A1 | 7/2014 | Wildhirt et al. |
| 2014/0194717 A1 | 7/2014 | Wildhirt et al. |
| 2014/0199377 A1 | 7/2014 | Stankus et al. |
| 2014/0200655 A1 | 7/2014 | Webler et al. |
| 2014/0207232 A1 | 7/2014 | Garrigue |
| 2014/0228741 A1 | 8/2014 | Frankowski et al. |
| 2014/0243970 A1 | 8/2014 | Yanai |
| 2014/0255176 A1 | 9/2014 | Bredenbreuker et al. |
| 2014/0275721 A1 | 9/2014 | Yanai et al. |
| 2014/0275725 A1 | 9/2014 | Schenck et al. |
| 2014/0288354 A1 | 9/2014 | Timms et al. |
| 2014/0309481 A1 | 10/2014 | Medvedev et al. |
| 2014/0336444 A1 | 11/2014 | Bonde |
| 2014/0336486 A1 | 11/2014 | Ouyang et al. |
| 2014/0336747 A1 | 11/2014 | Rapoza et al. |
| 2014/0341726 A1 | 11/2014 | Wu et al. |
| 2014/0350328 A1 | 11/2014 | Mohl |
| 2014/0357938 A1 | 12/2014 | Pilla et al. |
| 2014/0370073 A1 | 12/2014 | Tang et al. |
| 2015/0005571 A1 | 1/2015 | Jeffery et al. |
| 2015/0018747 A1 | 1/2015 | Michal et al. |
| 2015/0031938 A1 | 1/2015 | Crosby et al. |
| 2015/0051437 A1 | 2/2015 | Miyakoshi et al. |
| 2015/0068069 A1 | 3/2015 | Tran et al. |
| 2015/0080639 A1 | 3/2015 | Radziemski et al. |
| 2015/0080743 A1 | 3/2015 | Siess |
| 2015/0087890 A1 | 3/2015 | Spanier et al. |
| 2015/0112210 A1 | 4/2015 | Webler |
| 2015/0120323 A1 | 4/2015 | Galasso et al. |
| 2015/0134048 A1 | 5/2015 | Ding |
| 2015/0152878 A1 | 6/2015 | McBride et al. |
| 2015/0159643 A1 | 6/2015 | Koob |
| 2015/0174060 A1 | 6/2015 | Heit et al. |
| 2015/0191607 A1 | 7/2015 | McDaniel |
| 2015/0207331 A1 | 7/2015 | Petersen |
| 2015/0216685 A1 | 8/2015 | Spence et al. |
| 2015/0222128 A1 | 8/2015 | Hansen |
| 2015/0222139 A1 | 8/2015 | Petersen et al. |
| 2015/0226691 A1 | 8/2015 | Wang et al. |
| 2015/0230709 A1 | 8/2015 | Milner et al. |
| 2015/0231317 A1 | 8/2015 | Schima et al. |
| 2015/0238671 A1 | 8/2015 | Mesallum |
| 2015/0265757 A1 | 9/2015 | Dowling et al. |
| 2015/0283027 A1 | 10/2015 | Lampe et al. |
| 2015/0285258 A1 | 10/2015 | Foster |
| 2015/0290370 A1 | 10/2015 | Crunkleton et al. |
| 2015/0290377 A1 | 10/2015 | Kearsley et al. |
| 2015/0306291 A1 | 10/2015 | Bonde et al. |
| 2015/0320926 A1 | 11/2015 | Fitzpatrick et al. |
| 2015/0328382 A1 | 11/2015 | Corbett et al. |
| 2015/0335803 A1 | 11/2015 | Yamane |
| 2015/0364861 A1 | 12/2015 | Lucke et al. |
| 2015/0366495 A1 | 12/2015 | Gable, III et al. |
| 2015/0367050 A1 | 12/2015 | Bulent et al. |
| 2015/0368335 A1 | 12/2015 | Banerjee et al. |
| 2015/0374892 A1 | 12/2015 | Yanai et al. |
| 2016/0022887 A1 | 1/2016 | Wampler |
| 2016/0030649 A1 | 2/2016 | Zeng |
| 2016/0038315 A1 | 2/2016 | Consigny et al. |
| 2016/0045098 A1 | 2/2016 | Tsubouchi |
| 2016/0045652 A1 | 2/2016 | Cornen |
| 2016/0045654 A1 | 2/2016 | Connor |
| 2016/0058434 A1 | 3/2016 | Delaloye et al. |
| 2016/0067395 A1 | 3/2016 | Jimenez et al. |
| 2016/0085714 A1 | 3/2016 | Goodnow et al. |
| 2016/0175044 A1 | 6/2016 | Abunassar et al. |
| 2016/0182158 A1 | 6/2016 | Lee et al. |
| 2016/0184499 A1 | 6/2016 | Ricci et al. |
| 2016/0199556 A1 | 7/2016 | Ayre et al. |
| 2016/0199557 A1 | 7/2016 | Bluvshtein et al. |
| 2016/0203275 A1 | 7/2016 | Benjamin et al. |
| 2016/0220269 A1 | 8/2016 | Labropoulos et al. |
| 2016/0220785 A1 | 8/2016 | Fabre |
| 2016/0222969 A1 | 8/2016 | Heide et al. |
| 2016/0250399 A1 | 9/2016 | Tiller et al. |
| 2016/0250400 A1 | 9/2016 | Schumacher |
| 2016/0251720 A1 | 9/2016 | Schulze et al. |
| 2016/0256620 A1 | 9/2016 | Scheckel et al. |
| 2016/0263299 A1 | 9/2016 | Xu et al. |
| 2016/0271161 A1 | 9/2016 | Dobson |
| 2016/0271309 A1 | 9/2016 | Throckmorton et al. |
| 2016/0279310 A1 | 9/2016 | Scheckel et al. |
| 2016/0303301 A1 | 10/2016 | Bluvshtein et al. |
| 2016/0308403 A1 | 10/2016 | Bluvshtein et al. |
| 2016/0317291 A1 | 11/2016 | Bishop et al. |
| 2016/0317333 A1 | 11/2016 | Ainsworth et al. |
| 2016/0325034 A1 | 11/2016 | Wiktor et al. |
| 2016/0348688 A1 | 12/2016 | Schumacher et al. |
| 2016/0354526 A1 | 12/2016 | Whisenant et al. |
| 2016/0375187 A1 | 12/2016 | Lee et al. |
| 2017/0000361 A1 | 1/2017 | Meyering et al. |
| 2017/0000935 A1 | 1/2017 | Vasilyev et al. |
| 2017/0007552 A1 | 1/2017 | Slepian |
| 2017/0007762 A1 | 1/2017 | Hayter et al. |
| 2017/0014401 A1 | 1/2017 | Dalton et al. |
| 2017/0021074 A1 | 1/2017 | Opfermann et al. |
| 2017/0028114 A1 | 2/2017 | Göllner et al. |
| 2017/0028115 A1 | 2/2017 | Muller |
| 2017/0035952 A1 | 2/2017 | Muller |
| 2017/0035954 A1 | 2/2017 | Muller et al. |
| 2017/0043076 A1 | 2/2017 | Wampler et al. |
| 2017/0063143 A1 | 3/2017 | Hoarau et al. |
| 2017/0080136 A1 | 3/2017 | Janczek et al. |
| 2017/0100527 A1 | 4/2017 | Schwammenthal et al. |
| 2017/0112984 A1 | 4/2017 | Vargas Fonseca |
| 2017/0119946 A1 | 5/2017 | McChrystal et al. |
| 2017/0136165 A1 | 5/2017 | Hansen et al. |
| 2017/0136225 A1 | 5/2017 | Siess et al. |
| 2017/0143883 A1 | 5/2017 | Spence |
| 2017/0143952 A1 | 5/2017 | Siess et al. |
| 2017/0157309 A1 | 6/2017 | Begg et al. |
| 2017/0193184 A1 | 7/2017 | Hayter et al. |
| 2017/0196638 A1 | 7/2017 | Serna et al. |
| 2017/0202575 A1 | 7/2017 | Stanfield et al. |
| 2017/0215918 A1 | 8/2017 | Tao et al. |
| 2017/0224896 A1 | 8/2017 | Graham et al. |
| 2017/0232168 A1 | 8/2017 | Reichenbach et al. |
| 2017/0232169 A1 | 8/2017 | Muller |
| 2017/0232172 A1 | 8/2017 | Mesallum |
| 2017/0239407 A1 | 8/2017 | Hayward |
| 2017/0250575 A1 | 8/2017 | Wong et al. |
| 2017/0265994 A1 | 9/2017 | Krone |
| 2017/0274128 A1 | 9/2017 | Tamburino et al. |
| 2017/0281025 A9 | 10/2017 | Glover et al. |
| 2017/0281841 A1 | 10/2017 | Larose et al. |
| 2017/0281842 A1 | 10/2017 | Larose et al. |
| 2017/0290964 A1 | 10/2017 | Barry |
| 2017/0296227 A1 | 10/2017 | Osypka |
| 2017/0296725 A1 | 10/2017 | Peters |

(56) References Cited

U.S. PATENT DOCUMENTS

| | | |
|---|---|---|
| 2017/0312106 A1 | 11/2017 | Gomez et al. |
| 2017/0312416 A1 | 11/2017 | Strueber |
| 2017/0312492 A1 | 11/2017 | Fantuzzi et al. |
| 2017/0319113 A1 | 11/2017 | Hurd et al. |
| 2017/0323713 A1 | 11/2017 | Moeller et al. |
| 2017/0325943 A1 | 11/2017 | Robin et al. |
| 2017/0333607 A1 | 11/2017 | Zarins |
| 2017/0333673 A1 | 11/2017 | Tuval et al. |
| 2017/0340789 A1 | 11/2017 | Bonde et al. |
| 2017/0340790 A1 | 11/2017 | Wiesener et al. |
| 2017/0360309 A1 | 12/2017 | Moore et al. |
| 2017/0361001 A1 | 12/2017 | Canatella et al. |
| 2017/0361011 A1 | 12/2017 | Muennich et al. |
| 2017/0363103 A1 | 12/2017 | Canatella et al. |
| 2017/0363210 A1 | 12/2017 | Durst et al. |
| 2017/0363620 A1 | 12/2017 | Beshiri et al. |
| 2017/0368246 A1 | 12/2017 | Criscione et al. |
| 2017/0370365 A1 | 12/2017 | Fritz et al. |
| 2018/0001003 A1 | 1/2018 | Moran et al. |
| 2018/0001007 A1 | 1/2018 | Stratton |
| 2018/0001012 A1 | 1/2018 | Ardehali |
| 2018/0001062 A1 | 1/2018 | O'Carrol et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0021497 A1 | 1/2018 | Nunez et al. |
| 2018/0028736 A1 | 2/2018 | Wong et al. |
| 2018/0035926 A1 | 2/2018 | Stafford |
| 2018/0040418 A1 | 2/2018 | Hansen et al. |
| 2018/0047282 A1 | 2/2018 | He et al. |
| 2018/0050139 A1 | 2/2018 | Siess et al. |
| 2018/0050140 A1 | 2/2018 | Siess et al. |
| 2018/0050142 A1 | 2/2018 | Siess et al. |
| 2018/0055383 A1 | 3/2018 | Manera |
| 2018/0055983 A1 | 3/2018 | Bourque |
| 2018/0058437 A1 | 3/2018 | Eilers et al. |
| 2018/0064862 A1 | 3/2018 | Keenan et al. |
| 2018/0071020 A1 | 3/2018 | Laufer et al. |
| 2018/0078159 A1 | 3/2018 | Edelman et al. |
| 2018/0085505 A1 | 3/2018 | Casas |
| 2018/0085507 A1 | 3/2018 | Casas et al. |
| 2018/0085509 A1 | 3/2018 | Petersen |
| 2018/0093026 A1 | 4/2018 | Angwin et al. |
| 2018/0097368 A1 | 4/2018 | Hansen |
| 2018/0099076 A1 | 4/2018 | Larose |
| 2018/0099078 A1 | 4/2018 | Tuseth et al. |
| 2018/0100507 A1 | 4/2018 | Wu et al. |
| 2018/0103611 A1 | 4/2018 | Mainini et al. |
| 2018/0103870 A1 | 4/2018 | Limaye et al. |
| 2018/0108275 A1 | 4/2018 | Newberry et al. |
| 2018/0110514 A1 | 4/2018 | Hoarau et al. |
| 2018/0114426 A1 | 4/2018 | Lee |
| 2018/0133380 A1 | 5/2018 | Liebing |
| 2018/0140759 A1 | 5/2018 | Kaiser et al. |
| 2018/0140801 A1 | 5/2018 | Voss et al. |
| 2018/0146968 A1 | 5/2018 | Nitzan et al. |
| 2018/0149164 A1 | 5/2018 | Siess |
| 2018/0149165 A1 | 5/2018 | Siess et al. |
| 2018/0154051 A1 | 6/2018 | Hossainy et al. |
| 2018/0154128 A1 | 6/2018 | Woo et al. |
| 2018/0161540 A1 | 6/2018 | Fantuzzi et al. |
| 2018/0161555 A1 | 6/2018 | Zhadkevich |
| 2018/0168469 A1 | 6/2018 | Granegger |
| 2018/0169313 A1 | 6/2018 | Schwammenthal et al. |
| 2018/0193543 A1 | 7/2018 | Sun |
| 2018/0193614 A1 | 7/2018 | Nitzan et al. |
| 2018/0193616 A1 | 7/2018 | Nitzan et al. |
| 2018/0200420 A1 | 7/2018 | Di Paola et al. |
| 2018/0200422 A1 | 7/2018 | Nguyen et al. |
| 2018/0202962 A1 | 7/2018 | Simmons et al. |
| 2018/0207334 A1 | 7/2018 | Siess |
| 2018/0207337 A1 | 7/2018 | Spence et al. |
| 2018/0207338 A1 | 7/2018 | Bluvshtein et al. |
| 2018/0228953 A1 | 8/2018 | Siess et al. |
| 2018/0228957 A1 | 8/2018 | Colella |
| 2018/0242891 A1 | 8/2018 | Bernstein et al. |
| 2018/0242976 A1 | 8/2018 | Kizuka |
| 2018/0243086 A1 | 8/2018 | Barbarino et al. |
| 2018/0243488 A1 | 8/2018 | Callaway et al. |
| 2018/0243489 A1 | 8/2018 | Haddadi |
| 2018/0243490 A1 | 8/2018 | Kallenbach et al. |
| 2018/0243492 A1 | 8/2018 | Salys |
| 2018/0250457 A1 | 9/2018 | Morello et al. |
| 2018/0250458 A1 | 9/2018 | Petersen et al. |
| 2018/0256242 A1 | 9/2018 | Bluvshtein et al. |
| 2018/0256794 A1 | 9/2018 | Rodefeld |
| 2018/0256795 A1 | 9/2018 | Schade et al. |
| 2018/0256797 A1 | 9/2018 | Schenck et al. |
| 2018/0256798 A1 | 9/2018 | Botterbusch et al. |
| 2018/0256859 A1 | 9/2018 | Korkuch |
| 2018/0264183 A1 | 9/2018 | Jahangir |
| 2018/0264184 A1 | 9/2018 | Jeffries et al. |
| 2018/0269692 A1 | 9/2018 | Petersen et al. |
| 2018/0280598 A1 | 10/2018 | Curran et al. |
| 2018/0280599 A1 | 10/2018 | Harjes et al. |
| 2018/0280600 A1 | 10/2018 | Harjes et al. |
| 2018/0280601 A1 | 10/2018 | Harjes et al. |
| 2018/0280604 A1 | 10/2018 | Hobro et al. |
| 2018/0289295 A1 | 10/2018 | Hoss et al. |
| 2018/0289876 A1 | 10/2018 | Nguyen et al. |
| 2018/0289877 A1 | 10/2018 | Schumacher et al. |
| 2018/0296572 A1 | 10/2018 | Deisher |
| 2019/0143018 A1 | 5/2019 | Salahieh et al. |
| 2019/0167873 A1 | 6/2019 | Koike et al. |
| 2019/0290822 A1 | 9/2019 | Igarashi |
| 2019/0344901 A1 | 11/2019 | Salahieh et al. |
| 2020/0029951 A1 | 1/2020 | Bessler et al. |
| 2020/0030510 A1 | 1/2020 | Higgins |
| 2020/0114053 A1 | 4/2020 | Salahieh et al. |
| 2020/0237981 A1 | 7/2020 | Tuval et al. |
| 2020/0246527 A1 | 8/2020 | Hildebrand et al. |
| 2021/0008261 A1* | 1/2021 | Calomeni ........... A61M 60/414 |
| 2021/0052794 A1 | 2/2021 | Tuval et al. |
| 2021/0121679 A1 | 4/2021 | Mohl et al. |
| 2022/0080178 A1 | 3/2022 | Salahieh et al. |

FOREIGN PATENT DOCUMENTS

| | | |
|---|---|---|
| CN | 1008307 B | 6/1990 |
| CN | 1053108 A | 7/1991 |
| CN | 1105103 A | 7/1995 |
| CN | 1146329 A | 4/1997 |
| CN | 1179708 A | 4/1998 |
| CN | 2326253 Y | 6/1999 |
| CN | 1222862 A | 7/1999 |
| CN | 1045058 C | 9/1999 |
| CN | 1235849 A | 11/1999 |
| CN | 2361290 Y | 2/2000 |
| CN | 1254598 A | 5/2000 |
| CN | 2386827 Y | 7/2000 |
| CN | 2412579 Y | 1/2001 |
| CN | 2417173 Y | 1/2001 |
| CN | 1310647 A | 8/2001 |
| CN | 1342497 A | 4/2002 |
| CN | 1088795 C | 8/2002 |
| CN | 2504815 Y | 8/2002 |
| CN | 1376523 A | 10/2002 |
| CN | 1097138 C | 12/2002 |
| CN | 1105581 C | 4/2003 |
| CN | 1421248 A | 6/2003 |
| CN | 2558386 Y | 7/2003 |
| CN | 1118304 C | 8/2003 |
| CN | 1436048 A | 8/2003 |
| CN | 1120729 C | 9/2003 |
| CN | 2574609 Y | 9/2003 |
| CN | 1140228 C | 3/2004 |
| CN | 1161581 C | 8/2004 |
| CN | 1167472 C | 9/2004 |
| CN | 1527906 A | 9/2004 |
| CN | 1559361 A | 1/2005 |
| CN | 1559626 A | 1/2005 |
| CN | 1572331 A | 2/2005 |
| CN | 1202871 C | 5/2005 |
| CN | 1679974 A | 10/2005 |

(56) References Cited

FOREIGN PATENT DOCUMENTS

| | | | |
|---|---|---|---|
| CN | 1694338 | A | 11/2005 |
| CN | 1705462 | A | 12/2005 |
| CN | 1239133 | C | 2/2006 |
| CN | 1239209 | C | 2/2006 |
| CN | 2754637 | Y | 2/2006 |
| CN | 1244381 | C | 3/2006 |
| CN | 1249339 | C | 4/2006 |
| CN | 2776418 | Y | 5/2006 |
| CN | 2787222 | Y | 6/2006 |
| CN | 1799652 | A | 7/2006 |
| CN | 1806774 | A | 7/2006 |
| CN | 1826463 | A | 8/2006 |
| CN | 1833735 | A | 9/2006 |
| CN | 1833736 | A | 9/2006 |
| CN | 2831716 | Y | 10/2006 |
| CN | 1874805 | A | 12/2006 |
| CN | 1301583 | C | 2/2007 |
| CN | 1921947 | A | 2/2007 |
| CN | 2880096 | Y | 3/2007 |
| CN | 2899800 | Y | 5/2007 |
| CN | 101001765 | A | 7/2007 |
| CN | 1329666 | C | 8/2007 |
| CN | 101024098 | A | 8/2007 |
| CN | 101031302 | A | 9/2007 |
| CN | 101112628 | A | 1/2008 |
| CN | 101121045 | A | 2/2008 |
| CN | 101124002 | A | 2/2008 |
| CN | 101132830 | A | 2/2008 |
| CN | 100382855 | C | 4/2008 |
| CN | 101256992 | A | 9/2008 |
| CN | 100429406 | C | 10/2008 |
| CN | 100439717 | C | 12/2008 |
| CN | 100472042 | C | 3/2009 |
| CN | 201208423 | Y | 3/2009 |
| CN | 100488577 | C | 5/2009 |
| CN | 201230980 | Y | 5/2009 |
| CN | 201239369 | Y | 5/2009 |
| CN | 201246310 | Y | 5/2009 |
| CN | 101448535 | A | 6/2009 |
| CN | 101522115 | A | 9/2009 |
| CN | 101534883 | A | 9/2009 |
| CN | 201308666 | Y | 9/2009 |
| CN | 101563605 | A | 10/2009 |
| CN | 100558416 | C | 11/2009 |
| CN | 100566765 | C | 12/2009 |
| CN | 101595276 | A | 12/2009 |
| CN | 101631578 | A | 1/2010 |
| CN | 101652069 | A | 2/2010 |
| CN | 101678025 | A | 3/2010 |
| CN | 101687791 | A | 3/2010 |
| CN | 101244296 | B | 6/2010 |
| CN | 101730552 | A | 6/2010 |
| CN | 101208058 | B | 8/2010 |
| CN | 101808515 | A | 8/2010 |
| CN | 101401981 | B | 9/2010 |
| CN | 101843528 | A | 9/2010 |
| CN | 101232952 | B | 11/2010 |
| CN | 101361994 | B | 11/2010 |
| CN | 201618200 | U | 11/2010 |
| CN | 201710717 | U | 1/2011 |
| CN | 101417155 | B | 2/2011 |
| CN | 101581307 | B | 4/2011 |
| CN | 102065923 | A | 5/2011 |
| CN | 101269245 | B | 7/2011 |
| CN | 101618240 | B | 8/2011 |
| CN | 102166379 | A | 8/2011 |
| CN | 101484093 | B | 9/2011 |
| CN | 102292053 | A | 12/2011 |
| CN | 102422018 | A | 4/2012 |
| CN | 102438673 | A | 5/2012 |
| CN | 102475923 | A | 5/2012 |
| CN | 202218993 | U | 5/2012 |
| CN | 101983732 | B | 7/2012 |
| CN | 102553005 | A | 7/2012 |
| CN | 101590295 | B | 8/2012 |
| CN | 101822355 | B | 9/2012 |
| CN | 101822854 | B | 9/2012 |
| CN | 101189431 | B | 10/2012 |
| CN | 101810891 | B | 10/2012 |
| CN | 102711894 | A | 10/2012 |
| CN | 102869318 | A | 1/2013 |
| CN | 102917748 | A | 2/2013 |
| CN | 102088920 | B | 4/2013 |
| CN | 103026234 | A | 4/2013 |
| CN | 103068417 | A | 4/2013 |
| CN | 103172739 | A | 6/2013 |
| CN | 101420993 | B | 7/2013 |
| CN | 103206402 | A | 7/2013 |
| CN | 103228300 | A | 7/2013 |
| CN | 103356306 | A | 10/2013 |
| CN | 103381277 | A | 11/2013 |
| CN | 103432637 | A | 12/2013 |
| CN | 103437951 | A | 12/2013 |
| CN | 103446635 | A | 12/2013 |
| CN | 103458832 | A | 12/2013 |
| CN | 102319457 | B | 1/2014 |
| CN | 103509116 | A | 1/2014 |
| CN | 103541857 | A | 1/2014 |
| CN | 103635212 | A | 3/2014 |
| CN | 203507200 | U | 4/2014 |
| CN | 203539803 | U | 4/2014 |
| CN | 203591299 | U | 5/2014 |
| CN | 102317629 | B | 8/2014 |
| CN | 203756589 | U | 8/2014 |
| CN | 104043153 | A | 9/2014 |
| CN | 203829160 | U | 9/2014 |
| CN | 104105511 | A | 10/2014 |
| CN | 203935281 | U | 11/2014 |
| CN | 104208763 | A | 12/2014 |
| CN | 203971002 | U | 12/2014 |
| CN | 204050452 | U | 12/2014 |
| CN | 102271728 | B | 1/2015 |
| CN | 102294057 | B | 1/2015 |
| CN | 104271075 | A | 1/2015 |
| CN | 102588255 | B | 3/2015 |
| CN | 104470454 | A | 3/2015 |
| CN | 102300501 | B | 4/2015 |
| CN | 103055363 | B | 4/2015 |
| CN | 104473676 | A | 4/2015 |
| CN | 104524663 | A | 4/2015 |
| CN | 204293210 | U | 4/2015 |
| CN | 102686316 | B | 5/2015 |
| CN | 104586469 | A | 5/2015 |
| CN | 104602987 | A | 5/2015 |
| CN | 102458275 | B | 6/2015 |
| CN | 102458498 | B | 6/2015 |
| CN | 104684607 | A | 6/2015 |
| CN | 104721899 | A | 6/2015 |
| CN | 204419151 | U | 6/2015 |
| CN | 102397598 | B | 7/2015 |
| CN | 103446634 | B | 7/2015 |
| CN | 104758029 | A | 7/2015 |
| CN | 104771797 | A | 7/2015 |
| CN | 101868628 | B | 8/2015 |
| CN | 103706018 | B | 9/2015 |
| CN | 104955420 | A | 9/2015 |
| CN | 104984425 | A | 10/2015 |
| CN | 104997550 | A | 10/2015 |
| CN | 105007960 | A | 10/2015 |
| CN | 105142719 | A | 12/2015 |
| CN | 105208927 | A | 12/2015 |
| CN | 102176933 | B | 1/2016 |
| CN | 102947092 | B | 1/2016 |
| CN | 103717837 | B | 1/2016 |
| CN | 105228688 | A | 1/2016 |
| CN | 105283149 | A | 1/2016 |
| CN | 204972635 | U | 1/2016 |
| CN | 103228232 | B | 2/2016 |
| CN | 103355925 | B | 2/2016 |
| CN | 105311692 | A | 2/2016 |
| CN | 102257279 | B | 3/2016 |
| CN | 102472719 | B | 3/2016 |
| CN | 103154738 | B | 3/2016 |
| CN | 105451787 | A | 3/2016 |

(56) References Cited

FOREIGN PATENT DOCUMENTS

| | | | |
|---|---|---|---|
| CN | 205083494 U | 3/2016 |
| CN | 103850979 B | 4/2016 |
| CN | 105477706 A | 4/2016 |
| CN | 105517589 A | 4/2016 |
| CN | 205163763 U | 4/2016 |
| CN | 103002833 B | 5/2016 |
| CN | 103861163 B | 5/2016 |
| CN | 105555204 A | 5/2016 |
| CN | 205215814 U | 5/2016 |
| CN | 102940911 B | 6/2016 |
| CN | 105641762 A | 6/2016 |
| CN | 105641763 A | 6/2016 |
| CN | 105662439 A | 6/2016 |
| CN | 105709287 A | 6/2016 |
| CN | 105722477 A | 6/2016 |
| CN | 205322884 U | 6/2016 |
| CN | 104069555 B | 7/2016 |
| CN | 105744915 A | 7/2016 |
| CN | 105790453 A | 7/2016 |
| CN | 105792364 A | 7/2016 |
| CN | 105792780 A | 7/2016 |
| CN | 103260666 B | 8/2016 |
| CN | 103732171 B | 8/2016 |
| CN | 103928971 B | 8/2016 |
| CN | 105833370 A | 8/2016 |
| CN | 205411785 U | 8/2016 |
| CN | 205460099 U | 8/2016 |
| CN | 205528886 U | 8/2016 |
| CN | 103889369 B | 9/2016 |
| CN | 104849482 B | 9/2016 |
| CN | 105980660 A | 9/2016 |
| CN | 106075621 A | 11/2016 |
| CN | 106102657 A | 11/2016 |
| CN | 205681272 U | 11/2016 |
| CN | 205698666 U | 11/2016 |
| CN | 205698725 U | 11/2016 |
| CN | 205753678 U | 11/2016 |
| CN | 106214288 A | 12/2016 |
| CN | 106256321 A | 12/2016 |
| CN | 205779766 U | 12/2016 |
| CN | 106334224 A | 1/2017 |
| CN | 205867186 U | 1/2017 |
| CN | 205876589 U | 1/2017 |
| CN | 103281971 B | 2/2017 |
| CN | 106390218 A | 2/2017 |
| CN | 103533970 B | 3/2017 |
| CN | 104826183 B | 3/2017 |
| CN | 106512117 A | 3/2017 |
| CN | 106581840 A | 4/2017 |
| CN | 104068947 B | 5/2017 |
| CN | 106620912 A | 5/2017 |
| CN | 106691363 A | 5/2017 |
| CN | 106716137 A | 5/2017 |
| CN | 106794293 A | 5/2017 |
| CN | 104225696 B | 6/2017 |
| CN | 104918578 B | 6/2017 |
| CN | 105915005 B | 6/2017 |
| CN | 106902404 A | 6/2017 |
| CN | 206325049 U | 7/2017 |
| CN | 206355093 U | 7/2017 |
| CN | 105377321 B | 8/2017 |
| CN | 107050543 A | 8/2017 |
| CN | 107050544 A | 8/2017 |
| CN | 107080870 A | 8/2017 |
| CN | 107080871 A | 8/2017 |
| CN | 107110875 A | 8/2017 |
| CN | 206414547 U | 8/2017 |
| CN | 206443963 U | 8/2017 |
| CN | 103930214 B | 9/2017 |
| CN | 104619361 B | 9/2017 |
| CN | 104936550 B | 9/2017 |
| CN | 105188618 B | 9/2017 |
| CN | 107115162 A | 9/2017 |
| CN | 107126588 A | 9/2017 |
| CN | 107134208 A | 9/2017 |
| CN | 107157623 A | 9/2017 |
| CN | 103857363 B | 10/2017 |
| CN | 104768500 B | 10/2017 |
| CN | 105008841 B | 10/2017 |
| CN | 105492036 B | 10/2017 |
| CN | 107252339 A | 10/2017 |
| CN | 107281567 A | 10/2017 |
| CN | 206592332 U | 10/2017 |
| CN | 107349484 A | 11/2017 |
| CN | 206660203 U | 11/2017 |
| CN | 105287050 B | 12/2017 |
| CN | 105597172 B | 12/2017 |
| CN | 105854097 B | 12/2017 |
| CN | 107412892 A | 12/2017 |
| CN | 107440681 A | 12/2017 |
| CN | 107496054 A | 12/2017 |
| CN | 104602647 B | 1/2018 |
| CN | 106061523 B | 1/2018 |
| CN | 107551341 A | 1/2018 |
| CN | 206934393 U | 1/2018 |
| CN | 107693868 A | 2/2018 |
| CN | 107693869 A | 2/2018 |
| CN | 107708765 A | 2/2018 |
| CN | 207018256 U | 2/2018 |
| CN | 106029120 B | 3/2018 |
| CN | 107753153 A | 3/2018 |
| CN | 107754071 A | 3/2018 |
| CN | 107798980 A | 3/2018 |
| CN | 107835826 A | 3/2018 |
| CN | 107837430 A | 3/2018 |
| CN | 107862963 A | 3/2018 |
| CN | 207125933 U | 3/2018 |
| CN | 207136890 U | 3/2018 |
| CN | 105120796 B | 4/2018 |
| CN | 105214153 B | 4/2018 |
| CN | 107865988 A | 4/2018 |
| CN | 107886825 A | 4/2018 |
| CN | 107913442 A | 4/2018 |
| CN | 107921195 A | 4/2018 |
| CN | 107923311 A | 4/2018 |
| CN | 108025120 A | 5/2018 |
| CN | 108025123 A | 5/2018 |
| CN | 108066834 A | 5/2018 |
| CN | 207410652 U | 5/2018 |
| CN | 104470579 B | 6/2018 |
| CN | 105188604 B | 6/2018 |
| CN | 105492909 B | 6/2018 |
| CN | 105498002 B | 6/2018 |
| CN | 106535824 B | 6/2018 |
| CN | 108136110 A | 6/2018 |
| CN | 108144146 A | 6/2018 |
| CN | 108175884 A | 6/2018 |
| CN | 106028807 B | 7/2018 |
| CN | 106310410 B | 7/2018 |
| CN | 108273148 A | 7/2018 |
| CN | 108310486 A | 7/2018 |
| CN | 108348667 A | 7/2018 |
| CN | 207614108 U | 7/2018 |
| CN | 105640635 B | 8/2018 |
| CN | 105923112 B | 8/2018 |
| CN | 108367106 A | 8/2018 |
| CN | 108430533 A | 8/2018 |
| CN | 108457844 A | 8/2018 |
| CN | 108472138 A | 8/2018 |
| CN | 108472395 A | 8/2018 |
| CN | 108472424 A | 8/2018 |
| CN | 207708246 U | 8/2018 |
| CN | 207708250 U | 8/2018 |
| CN | 105407937 B | 9/2018 |
| CN | 105902298 B | 9/2018 |
| CN | 106420113 B | 9/2018 |
| CN | 106510902 B | 9/2018 |
| CN | 108525039 A | 9/2018 |
| CN | 108525040 A | 9/2018 |
| CN | 108601653 A | 9/2018 |
| CN | 108601872 A | 9/2018 |
| CN | 108601874 A | 9/2018 |
| CN | 108601875 A | 9/2018 |
| CN | 207924984 U | 9/2018 |

(56) References Cited

FOREIGN PATENT DOCUMENTS

| | | | |
|---|---|---|---|
| CN | 106377810 B | 10/2018 |
| EP | 96495 B1 | 9/1986 |
| EP | 79373 B1 | 12/1986 |
| EP | 54049 B1 | 1/1988 |
| EP | 292510 A4 | 8/1989 |
| EP | 167562 B1 | 4/1990 |
| EP | 230532 B1 | 9/1990 |
| EP | 241950 B1 | 12/1990 |
| EP | 129779 B1 | 4/1991 |
| EP | 202649 B1 | 8/1991 |
| EP | 445782 A1 | 9/1991 |
| EP | 464714 A1 | 1/1992 |
| EP | 293592 B1 | 11/1992 |
| EP | 297723 B1 | 8/1993 |
| EP | 396575 B1 | 3/1994 |
| EP | 397668 B1 | 3/1994 |
| EP | 593574 A1 | 4/1994 |
| EP | 378251 B1 | 6/1994 |
| EP | 605621 A1 | 7/1994 |
| EP | 467999 B1 | 8/1994 |
| EP | 350282 B1 | 11/1994 |
| EP | 478635 B1 | 12/1994 |
| EP | 397720 B1 | 3/1995 |
| EP | 421558 B1 | 4/1995 |
| EP | 364799 B1 | 5/1995 |
| EP | 660726 A1 | 7/1995 |
| EP | 672386 A1 | 9/1995 |
| EP | 349581 B1 | 1/1996 |
| EP | 464973 B1 | 1/1996 |
| EP | 505270 B1 | 1/1996 |
| EP | 480101 B1 | 5/1996 |
| EP | 583781 B1 | 5/1996 |
| EP | 583012 B1 | 7/1996 |
| EP | 756500 A1 | 2/1997 |
| EP | 0764448 A2 | 3/1997 |
| EP | 767318 A2 | 4/1997 |
| EP | 788808 A2 | 8/1997 |
| EP | 799060 A1 | 10/1997 |
| EP | 823567 A1 | 2/1998 |
| EP | 832357 A1 | 4/1998 |
| EP | 841917 A1 | 5/1998 |
| EP | 560000 B1 | 9/1998 |
| EP | 879012 A1 | 11/1998 |
| EP | 925078 A1 | 6/1999 |
| EP | 807141 B1 | 7/1999 |
| EP | 681654 B1 | 9/1999 |
| EP | 958066 A1 | 11/1999 |
| EP | 964718 A1 | 12/1999 |
| EP | 725657 B1 | 2/2000 |
| EP | 986409 A1 | 3/2000 |
| EP | 1007140 A1 | 6/2000 |
| EP | 1009466 A1 | 6/2000 |
| EP | 1027898 A1 | 8/2000 |
| EP | 1032437 A1 | 9/2000 |
| EP | 1045708 A1 | 10/2000 |
| EP | 1059885 A2 | 12/2000 |
| EP | 746712 B1 | 10/2001 |
| EP | 1139862 A1 | 10/2001 |
| EP | 1147317 A1 | 10/2001 |
| EP | 1148900 A1 | 10/2001 |
| EP | 699447 B1 | 11/2001 |
| EP | 591896 B1 | 2/2002 |
| EP | 731664 B1 | 2/2002 |
| EP | 797734 B1 | 2/2002 |
| EP | 1217954 A1 | 7/2002 |
| EP | 1231981 A1 | 8/2002 |
| EP | 950057 B1 | 11/2002 |
| EP | 751769 B1 | 1/2003 |
| EP | 1278461 A1 | 1/2003 |
| EP | 860046 B1 | 2/2003 |
| EP | 597881 B2 | 3/2003 |
| EP | 732949 B1 | 3/2003 |
| EP | 814701 B1 | 4/2003 |
| EP | 898479 B1 | 5/2003 |
| EP | 905379 B1 | 5/2003 |
| EP | 655625 B1 | 7/2003 |
| EP | 764448 B1 | 7/2003 |
| EP | 768091 B1 | 7/2003 |
| EP | 825888 B1 | 12/2003 |
| EP | 1379197 A1 | 1/2004 |
| EP | 1382366 A1 | 1/2004 |
| EP | 868145 B1 | 2/2004 |
| EP | 895480 B1 | 5/2004 |
| EP | 1441777 A2 | 8/2004 |
| EP | 916359 B1 | 9/2004 |
| EP | 1482999 A1 | 12/2004 |
| EP | 1291027 B1 | 3/2005 |
| EP | 877633 B1 | 7/2005 |
| EP | 611228 B2 | 8/2005 |
| EP | 1212516 B1 | 10/2005 |
| EP | 1597457 A2 | 11/2005 |
| EP | 1261385 B1 | 2/2006 |
| EP | 1648309 A1 | 4/2006 |
| EP | 1354606 B1 | 6/2006 |
| EP | 1663081 A1 | 6/2006 |
| EP | 1321166 B1 | 7/2006 |
| EP | 1191956 B1 | 9/2006 |
| EP | 1722767 A2 | 11/2006 |
| EP | 1070510 B1 | 1/2007 |
| EP | 1317295 B1 | 1/2007 |
| EP | 1327455 B1 | 1/2007 |
| EP | 1776095 A1 | 4/2007 |
| EP | 1141670 B1 | 7/2007 |
| EP | 1807148 A2 | 7/2007 |
| EP | 1827448 A1 | 9/2007 |
| EP | 1374928 B1 | 12/2007 |
| EP | 1877133 A2 | 1/2008 |
| EP | 1379294 B1 | 5/2008 |
| EP | 1930034 A1 | 6/2008 |
| EP | 1318848 B1 | 7/2008 |
| EP | 1356859 B1 | 8/2008 |
| EP | 1955725 A2 | 8/2008 |
| EP | 2058017 A2 | 5/2009 |
| EP | 1731957 B1 | 8/2009 |
| EP | 1173238 B1 | 10/2009 |
| EP | 2043553 B1 | 3/2010 |
| EP | 2158491 A2 | 3/2010 |
| EP | 2178580 A2 | 4/2010 |
| EP | 2182844 A1 | 5/2010 |
| EP | 2194278 A1 | 6/2010 |
| EP | 1471952 B1 | 7/2010 |
| EP | 2207578 A1 | 7/2010 |
| EP | 2216059 A1 | 8/2010 |
| EP | 2218469 A1 | 8/2010 |
| EP | 2219699 A1 | 8/2010 |
| EP | 2222635 A2 | 9/2010 |
| EP | 2222788 A1 | 9/2010 |
| EP | 2229965 A1 | 9/2010 |
| EP | 2235204 A1 | 10/2010 |
| EP | 1280581 B1 | 11/2010 |
| EP | 2246078 A1 | 11/2010 |
| EP | 2248544 A1 | 11/2010 |
| EP | 2252337 A1 | 11/2010 |
| EP | 2266640 A1 | 12/2010 |
| EP | 2269670 A1 | 1/2011 |
| EP | 2297583 A2 | 3/2011 |
| EP | 2298371 A1 | 3/2011 |
| EP | 2298372 A1 | 3/2011 |
| EP | 2298373 A1 | 3/2011 |
| EP | 2299119 A1 | 3/2011 |
| EP | 1464348 B1 | 4/2011 |
| EP | 2314330 A1 | 4/2011 |
| EP | 2314331 A1 | 4/2011 |
| EP | 2338539 A1 | 6/2011 |
| EP | 2338540 A1 | 6/2011 |
| EP | 2338541 A1 | 6/2011 |
| EP | 1654027 B1 | 7/2011 |
| EP | 2343091 A1 | 7/2011 |
| EP | 2347778 A1 | 7/2011 |
| EP | 1812094 B1 | 8/2011 |
| EP | 2349385 A1 | 8/2011 |
| EP | 2353626 A1 | 8/2011 |
| EP | 2356458 A1 | 8/2011 |
| EP | 2363157 A1 | 9/2011 |

(56) References Cited

FOREIGN PATENT DOCUMENTS

| | | | |
|---|---|---|---|
| EP | 2366412 A2 | 9/2011 |
| EP | 1907049 B1 | 11/2011 |
| EP | 2388027 A1 | 11/2011 |
| EP | 2388029 A1 | 11/2011 |
| EP | 2399639 A1 | 12/2011 |
| EP | 1514571 B1 | 1/2012 |
| EP | 2407185 A1 | 1/2012 |
| EP | 2407186 A1 | 1/2012 |
| EP | 2407187 A1 | 1/2012 |
| EP | 2422735 A1 | 2/2012 |
| EP | 2322600 B1 | 3/2012 |
| EP | 2429603 A2 | 3/2012 |
| EP | 2459269 A1 | 6/2012 |
| EP | 2497521 A1 | 9/2012 |
| EP | 2140892 B1 | 10/2012 |
| EP | 2505228 A1 | 10/2012 |
| EP | 2150811 B1 | 1/2013 |
| EP | 1833529 B1 | 2/2013 |
| EP | 2554191 A1 | 2/2013 |
| EP | 2277463 B1 | 3/2013 |
| EP | 2564771 A1 | 3/2013 |
| EP | 2151257 B1 | 4/2013 |
| EP | 2575922 A2 | 4/2013 |
| EP | 1623730 B1 | 5/2013 |
| EP | 2606919 A1 | 6/2013 |
| EP | 2606920 A1 | 6/2013 |
| EP | 2607712 A1 | 6/2013 |
| EP | 1919550 B1 | 7/2013 |
| EP | 2620173 A1 | 7/2013 |
| EP | 1331017 B1 | 8/2013 |
| EP | 2101840 B1 | 9/2013 |
| EP | 2401003 B1 | 10/2013 |
| EP | 2654878 A2 | 10/2013 |
| EP | 2654883 A2 | 10/2013 |
| EP | 2671083 A1 | 12/2013 |
| EP | 1412001 B1 | 1/2014 |
| EP | 1942965 B1 | 1/2014 |
| EP | 2231222 B1 | 2/2014 |
| EP | 2697890 A2 | 2/2014 |
| EP | 1017433 B1 | 3/2014 |
| EP | 1629855 B1 | 4/2014 |
| EP | 2736581 A2 | 6/2014 |
| EP | 2744460 A1 | 6/2014 |
| EP | 2745869 A1 | 6/2014 |
| EP | 1485613 B1 | 7/2014 |
| EP | 1605988 B1 | 8/2014 |
| EP | 2792696 A2 | 10/2014 |
| EP | 2195043 B1 | 12/2014 |
| EP | 1962949 B1 | 2/2015 |
| EP | 2030641 B1 | 2/2015 |
| EP | 2643927 B1 | 4/2015 |
| EP | 2868331 A2 | 5/2015 |
| EP | 1460972 B1 | 6/2015 |
| EP | 2150569 B1 | 6/2015 |
| EP | 2152783 B1 | 6/2015 |
| EP | 2345439 B1 | 6/2015 |
| EP | 2895215 A2 | 7/2015 |
| EP | 1761306 B1 | 8/2015 |
| EP | 2663347 B1 | 8/2015 |
| EP | 2209508 B1 | 9/2015 |
| EP | 2915129 A1 | 9/2015 |
| EP | 2920421 A2 | 9/2015 |
| EP | 2533732 B1 | 11/2015 |
| EP | 1317305 B1 | 12/2015 |
| EP | 1339443 B1 | 1/2016 |
| EP | 2967284 A1 | 1/2016 |
| EP | 2967547 A1 | 1/2016 |
| EP | 2984731 A1 | 2/2016 |
| EP | 2167158 B1 | 3/2016 |
| EP | 2061531 B1 | 4/2016 |
| EP | 2519274 B1 | 4/2016 |
| EP | 1996252 B1 | 5/2016 |
| EP | 2464395 B1 | 5/2016 |
| EP | 3047873 A1 | 7/2016 |
| EP | 3047911 A1 | 7/2016 |
| EP | 2643053 B1 | 8/2016 |
| EP | 2734251 B1 | 8/2016 |
| EP | 3050537 A1 | 8/2016 |
| EP | 1942128 B1 | 9/2016 |
| EP | 2099509 B1 | 9/2016 |
| EP | 2719403 B1 | 9/2016 |
| EP | 3072210 A1 | 9/2016 |
| EP | 3072211 A1 | 9/2016 |
| EP | 2405140 B1 | 10/2016 |
| EP | 2197507 B1 | 11/2016 |
| EP | 2538086 B1 | 11/2016 |
| EP | 3086834 A1 | 11/2016 |
| EP | 2806911 B1 | 12/2016 |
| EP | 3110468 A1 | 1/2017 |
| EP | 3113808 A1 | 1/2017 |
| EP | 3119452 A1 | 1/2017 |
| EP | 3120811 A2 | 1/2017 |
| EP | 3131595 A1 | 2/2017 |
| EP | 3131596 A1 | 2/2017 |
| EP | 3131599 A1 | 2/2017 |
| EP | 3131600 A1 | 2/2017 |
| EP | 3131615 A1 | 2/2017 |
| EP | 2585129 B1 | 3/2017 |
| EP | 2594799 B1 | 3/2017 |
| EP | 3146987 A1 | 3/2017 |
| EP | 3157597 A1 | 4/2017 |
| EP | 3173110 A1 | 5/2017 |
| EP | 2825107 B1 | 7/2017 |
| EP | 3185924 A1 | 7/2017 |
| EP | 3185925 A1 | 7/2017 |
| EP | 3189526 A1 | 7/2017 |
| EP | 3191164 A1 | 7/2017 |
| EP | 2618001 B1 | 8/2017 |
| EP | 3197602 A1 | 8/2017 |
| EP | 3198677 A1 | 8/2017 |
| EP | 3204989 A1 | 8/2017 |
| EP | 3212250 A1 | 9/2017 |
| EP | 3219339 A1 | 9/2017 |
| EP | 3223880 A1 | 10/2017 |
| EP | 3232948 A1 | 10/2017 |
| EP | 1885409 B1 | 11/2017 |
| EP | 2292282 B1 | 11/2017 |
| EP | 2945661 B1 | 11/2017 |
| EP | 3238764 A1 | 11/2017 |
| EP | 3244814 A1 | 11/2017 |
| EP | 3247420 A1 | 11/2017 |
| EP | 3247421 A2 | 11/2017 |
| EP | 3248628 A1 | 11/2017 |
| EP | 2136861 B1 | 12/2017 |
| EP | 3256183 A1 | 12/2017 |
| EP | 3256184 A1 | 12/2017 |
| EP | 3256185 A1 | 12/2017 |
| EP | 3256186 A1 | 12/2017 |
| EP | 3007742 B1 | 1/2018 |
| EP | 3277200 A1 | 2/2018 |
| EP | 3287155 A1 | 2/2018 |
| EP | 2482916 B1 | 3/2018 |
| EP | 2948202 B1 | 3/2018 |
| EP | 3294367 A1 | 3/2018 |
| EP | 2945662 B1 | 4/2018 |
| EP | 3310409 A1 | 4/2018 |
| EP | 3222301 B1 | 5/2018 |
| EP | 3222302 B1 | 5/2018 |
| EP | 3313471 A1 | 5/2018 |
| EP | 3324840 A1 | 5/2018 |
| EP | 3325035 A1 | 5/2018 |
| EP | 3326487 A1 | 5/2018 |
| EP | 1789129 B1 | 6/2018 |
| EP | 1990358 B1 | 6/2018 |
| EP | 3329953 A1 | 6/2018 |
| EP | 3335647 A2 | 6/2018 |
| EP | 3341069 A1 | 7/2018 |
| EP | 3349839 A1 | 7/2018 |
| EP | 2219698 B1 | 8/2018 |
| EP | 2890420 B1 | 8/2018 |
| EP | 3352808 A1 | 8/2018 |
| EP | 3352835 A1 | 8/2018 |
| EP | 3360233 A1 | 8/2018 |
| EP | 3360515 A1 | 8/2018 |

(56) References Cited

FOREIGN PATENT DOCUMENTS

| | | |
|---|---|---|
| EP | 1534381 B1 | 9/2018 |
| EP | 3108909 B1 | 9/2018 |
| EP | 3377001 A1 | 9/2018 |
| EP | 3377002 A1 | 9/2018 |
| EP | 3377134 A1 | 9/2018 |
| EP | 3377135 A1 | 9/2018 |
| EP | 3377136 A1 | 9/2018 |
| EP | 2249746 B1 | 10/2018 |
| EP | 2988795 B1 | 10/2018 |
| EP | 3383300 A1 | 10/2018 |
| EP | 3383448 A1 | 10/2018 |
| EP | 3388005 A1 | 10/2018 |
| JP | 64-52472 A | 2/1989 |
| JP | 02289241 A | 11/1990 |
| JP | 04176471 A | 6/1992 |
| JP | 04224760 A | 8/1992 |
| JP | H11-062856 A | 3/1999 |
| JP | 02888609 B2 | 5/1999 |
| JP | 02927460 B2 | 7/1999 |
| JP | H11-244376 A | 9/1999 |
| JP | 2000102604 A | 4/2000 |
| JP | 2000107281 A | 4/2000 |
| JP | 2000283062 A | 10/2000 |
| JP | 03131696 B2 | 2/2001 |
| JP | 2001061957 A | 3/2001 |
| JP | 2001090687 A | 4/2001 |
| JP | 03174338 B2 | 6/2001 |
| JP | 2001173402 A | 6/2001 |
| JP | 03278160 B2 | 4/2002 |
| JP | 2002191123 A | 7/2002 |
| JP | 03313061 B2 | 8/2002 |
| JP | 2003047656 A | 2/2003 |
| JP | 2003070906 A | 3/2003 |
| JP | 2003205030 A | 7/2003 |
| JP | 2004011525 A | 1/2004 |
| JP | 2004016426 A | 1/2004 |
| JP | 2004028102 A | 1/2004 |
| JP | 2004073400 A | 3/2004 |
| JP | 2004209240 A | 7/2004 |
| JP | 2004278375 A | 10/2004 |
| JP | 03612581 B2 | 1/2005 |
| JP | 2005058617 A | 3/2005 |
| JP | 2005192687 A | 7/2005 |
| JP | 2005199076 A | 7/2005 |
| JP | 2005348996 A | 12/2005 |
| JP | 2006000631 A | 1/2006 |
| JP | 03786289 B2 | 6/2006 |
| JP | 03803417 B2 | 8/2006 |
| JP | 2006280571 A | 10/2006 |
| JP | 03854972 B2 | 12/2006 |
| JP | 2007044302 A | 2/2007 |
| JP | 2007075541 A | 3/2007 |
| JP | 2007039973 A | 4/2007 |
| JP | 2007089607 A | 4/2007 |
| JP | 2007236564 A | 9/2007 |
| JP | 04016441 B2 | 12/2007 |
| JP | 04022372 B2 | 12/2007 |
| JP | 2008018242 A | 1/2008 |
| JP | 04051812 B2 | 2/2008 |
| JP | 04072721 B2 | 4/2008 |
| JP | 04077902 B2 | 4/2008 |
| JP | 04078245 B2 | 4/2008 |
| JP | 04084060 B2 | 4/2008 |
| JP | 04086185 B2 | 5/2008 |
| JP | 04108054 B2 | 6/2008 |
| JP | 04121709 B2 | 7/2008 |
| JP | 04163384 B2 | 10/2008 |
| JP | 04179634 B2 | 11/2008 |
| JP | 2008264586 A | 11/2008 |
| JP | 04198986 B2 | 12/2008 |
| JP | 04209412 B2 | 1/2009 |
| JP | 2009090882 A | 4/2009 |
| JP | 04279494 B2 | 6/2009 |
| JP | 04308723 B2 | 8/2009 |
| JP | 2009178570 A | 8/2009 |
| JP | 2009254436 A | 11/2009 |
| JP | 2009273214 A | 11/2009 |
| JP | 04387106 B2 | 12/2009 |
| JP | 04391680 B2 | 12/2009 |
| JP | 04414925 B2 | 2/2010 |
| JP | 04440499 B2 | 3/2010 |
| JP | 04467187 B2 | 5/2010 |
| JP | 04468965 B2 | 5/2010 |
| JP | 04484320 B2 | 6/2010 |
| JP | 04512150 B2 | 7/2010 |
| JP | 2010158532 A | 7/2010 |
| JP | 04523961 B2 | 8/2010 |
| JP | 04523962 B2 | 8/2010 |
| JP | 04548450 B2 | 9/2010 |
| JP | 04549407 B2 | 9/2010 |
| JP | 2010246941 A | 11/2010 |
| JP | 04611364 B2 | 1/2011 |
| JP | 04611365 B2 | 1/2011 |
| JP | 04646393 B2 | 3/2011 |
| JP | 04655231 B2 | 3/2011 |
| JP | 04656332 B2 | 3/2011 |
| JP | 04674978 B2 | 4/2011 |
| JP | 2011072533 A | 4/2011 |
| JP | 2011116765 A | 6/2011 |
| JP | 04728351 B2 | 7/2011 |
| JP | 04741242 B2 | 8/2011 |
| JP | 04741489 B2 | 8/2011 |
| JP | 2011161401 A | 8/2011 |
| JP | 04795536 B2 | 10/2011 |
| JP | 04851333 B2 | 1/2012 |
| JP | 04865825 B2 | 2/2012 |
| JP | 04881154 B2 | 2/2012 |
| JP | 04897811 B2 | 3/2012 |
| JP | 04907028 B2 | 3/2012 |
| JP | 04908737 B2 | 4/2012 |
| JP | 04964854 B2 | 7/2012 |
| JP | 04987999 B2 | 8/2012 |
| JP | 05047447 B2 | 10/2012 |
| JP | 05048749 B2 | 10/2012 |
| JP | 05093869 B2 | 12/2012 |
| JP | 05102033 B2 | 12/2012 |
| JP | 05164558 B2 | 3/2013 |
| JP | 05185629 B2 | 4/2013 |
| JP | 05193059 B2 | 5/2013 |
| JP | 05197636 B2 | 5/2013 |
| JP | 2013078564 A | 5/2013 |
| JP | 05215580 B2 | 6/2013 |
| JP | 05267227 B2 | 8/2013 |
| JP | 05286268 B2 | 9/2013 |
| JP | 2013192711 A | 9/2013 |
| JP | 2014004303 A | 1/2014 |
| JP | 05427620 B2 | 2/2014 |
| JP | 05429714 B2 | 2/2014 |
| JP | 05440528 B2 | 3/2014 |
| JP | 05440529 B2 | 3/2014 |
| JP | 05461710 B2 | 4/2014 |
| JP | 05500348 B2 | 5/2014 |
| JP | 2014091049 A | 5/2014 |
| JP | 2014114784 A | 6/2014 |
| JP | 05539484 B2 | 7/2014 |
| JP | 05557175 B2 | 7/2014 |
| JP | 05590213 B2 | 9/2014 |
| JP | 05596974 B2 | 10/2014 |
| JP | 05611948 B2 | 10/2014 |
| JP | 05633512 B2 | 12/2014 |
| JP | 05656835 B2 | 1/2015 |
| JP | 05673795 B2 | 2/2015 |
| JP | 05675786 B2 | 2/2015 |
| JP | 05676118 B2 | 2/2015 |
| JP | 05701848 B2 | 4/2015 |
| JP | 05711245 B2 | 4/2015 |
| JP | 05750492 B2 | 7/2015 |
| JP | 05781597 B2 | 9/2015 |
| JP | 2015159947 A | 9/2015 |
| JP | 05837162 B2 | 12/2015 |
| JP | 05868180 B2 | 2/2016 |
| JP | 05894116 B2 | 3/2016 |
| JP | 05894678 B2 | 3/2016 |
| JP | 2016028764 A | 3/2016 |

(56) References Cited

FOREIGN PATENT DOCUMENTS

| | | |
|---|---|---|
| JP | 2016182342 A | 10/2016 |
| JP | 06034858 B2 | 11/2016 |
| JP | 06038018 B2 | 12/2016 |
| JP | 06054106 B2 | 12/2016 |
| JP | 2016202553 A | 12/2016 |
| JP | 06083929 B2 | 2/2017 |
| JP | 2017035323 A | 2/2017 |
| JP | 2017517306 A | 6/2017 |
| JP | 2017127675 A | 7/2017 |
| JP | 06178666 B2 | 8/2017 |
| JP | 2017159083 A | 9/2017 |
| JP | 06220867 B2 | 10/2017 |
| JP | 06236451 B2 | 11/2017 |
| JP | 06267625 B2 | 1/2018 |
| JP | 2018020199 A | 2/2018 |
| JP | 06295204 B2 | 3/2018 |
| JP | 06329358 B2 | 5/2018 |
| JP | 06339371 B2 | 6/2018 |
| JP | 06345112 B2 | 6/2018 |
| JP | 06353787 B2 | 7/2018 |
| JP | 06382285 B2 | 8/2018 |
| JP | 2018122146 A | 8/2018 |
| JP | 2018523541 A | 8/2018 |
| WO | WO87/002894 A2 | 5/1987 |
| WO | WO88/009874 A1 | 12/1988 |
| WO | WO92/002263 A1 | 2/1992 |
| WO | WO92/003181 A1 | 3/1992 |
| WO | WO95/031196 A1 | 11/1995 |
| WO | WO96/016684 A1 | 6/1996 |
| WO | WO98/042984 A1 | 10/1998 |
| WO | WO00/019097 A1 | 4/2000 |
| WO | WO00/027446 A1 | 5/2000 |
| WO | WO00/035515 A1 | 6/2000 |
| WO | WO01/041070 A1 | 6/2001 |
| WO | WO01/074419 A1 | 10/2001 |
| WO | WO01/087176 A1 | 11/2001 |
| WO | WO01/095813 A1 | 12/2001 |
| WO | WO02/053226 A2 | 7/2002 |
| WO | WO02/070039 A2 | 9/2002 |
| WO | WO02/072000 A1 | 9/2002 |
| WO | WO02/081021 A1 | 10/2002 |
| WO | WO03/061727 A2 | 7/2003 |
| WO | WO03/094716 A1 | 11/2003 |
| WO | WO03/103745 A2 | 12/2003 |
| WO | WO2004/026394 A1 | 4/2004 |
| WO | WO2004/034034 A1 | 4/2004 |
| WO | WO2004/088480 A2 | 10/2004 |
| WO | WO2004/098677 A1 | 11/2004 |
| WO | WO2005/020848 A2 | 3/2005 |
| WO | WO2005/033671 A1 | 4/2005 |
| WO | WO2005/037348 A1 | 4/2005 |
| WO | WO2005/054680 A1 | 6/2005 |
| WO | WO2005/108796 A1 | 11/2005 |
| WO | WO2006/040252 A1 | 4/2006 |
| WO | WO2006/053384 A1 | 5/2006 |
| WO | WO2006/081255 A2 | 8/2006 |
| WO | WO2006/121698 A2 | 11/2006 |
| WO | WO2007/008907 A2 | 1/2007 |
| WO | WO2007/033933 A1 | 3/2007 |
| WO | WO2007/053881 A1 | 5/2007 |
| WO | WO2007/065408 A2 | 6/2007 |
| WO | WO2007/092494 A2 | 8/2007 |
| WO | WO2007/105842 A1 | 9/2007 |
| WO | WO2007/146231 A2 | 12/2007 |
| WO | WO2008/005747 A2 | 1/2008 |
| WO | WO2008/008427 A2 | 1/2008 |
| WO | WO2008/088874 A2 | 7/2008 |
| WO | WO2008/102015 A1 | 8/2008 |
| WO | WO2008/121143 A1 | 10/2008 |
| WO | WO2008/121145 A1 | 10/2008 |
| WO | WO2008/137237 A2 | 11/2008 |
| WO | WO2008/140034 A1 | 11/2008 |
| WO | WO2009/017549 A1 | 2/2009 |
| WO | WO2009035581 A1 | 3/2009 |
| WO | WO2009/046789 A1 | 4/2009 |
| WO | WO2009/075668 A2 | 6/2009 |
| WO | WO2010/025411 A2 | 3/2010 |
| WO | WO2011/003043 A1 | 1/2011 |
| WO | WO2011/024928 A1 | 3/2011 |
| WO | WO2011/035925 A1 | 3/2011 |
| WO | WO2011/039091 A1 | 4/2011 |
| WO | WO2011/081629 A1 | 7/2011 |
| WO | WO2011/082212 A1 | 7/2011 |
| WO | WO2011/085040 A1 | 7/2011 |
| WO | WO2011/117566 A1 | 9/2011 |
| WO | WO2011/119060 A2 | 9/2011 |
| WO | WO2012/051454 A2 | 4/2012 |
| WO | WO2012/064674 A1 | 5/2012 |
| WO | WO2012/075152 A1 | 6/2012 |
| WO | WO2012/075262 A1 | 6/2012 |
| WO | WO2012/087811 A2 | 6/2012 |
| WO | WO2012/094535 A2 | 7/2012 |
| WO | WO2012/094641 A2 | 7/2012 |
| WO | WO2012/112129 A1 | 8/2012 |
| WO | WO2013/034547 A1 | 3/2013 |
| WO | WO2013/093058 A1 | 6/2013 |
| WO | WO2013/127182 A1 | 9/2013 |
| WO | WO2013/134319 A1 | 9/2013 |
| WO | WO2013/148560 A1 | 10/2013 |
| WO | WO2013/148697 A1 | 10/2013 |
| WO | WO2014/070458 A1 | 5/2014 |
| WO | WO2014/096408 A1 | 6/2014 |
| WO | WO2014/106635 A1 | 7/2014 |
| WO | WO2014/116639 A1 | 7/2014 |
| WO | WO2014/142754 A1 | 9/2014 |
| WO | WO2014/143593 A1 | 9/2014 |
| WO | WO2014/164136 A1 | 10/2014 |
| WO | WO2014/164292 A1 | 10/2014 |
| WO | WO2014/166128 A1 | 10/2014 |
| WO | WO2014/169023 A2 | 10/2014 |
| WO | WO2015/119705 A1 | 8/2015 |
| WO | WO2015/160943 A1 | 10/2015 |
| WO | WO2015/160979 A1 | 10/2015 |
| WO | WO2015/171156 A1 | 11/2015 |
| WO | WO2015/175711 A1 | 11/2015 |
| WO | WO2015/175718 A1 | 11/2015 |
| WO | WO2015/177793 A2 | 11/2015 |
| WO | WO2015/187659 A2 | 12/2015 |
| WO | WO2016/100600 A2 | 6/2016 |
| WO | WO2016/113266 A1 | 7/2016 |
| WO | WO2016/116630 A2 | 7/2016 |
| WO | WO2017/001358 A1 | 1/2017 |
| WO | WO2017/011257 A1 | 1/2017 |
| WO | WO2017/032751 A1 | 3/2017 |
| WO | WO2017/048733 A1 | 3/2017 |
| WO | WO2017/060254 A1 | 4/2017 |
| WO | WO2017/060257 A1 | 4/2017 |
| WO | WO2017/075322 A1 | 5/2017 |
| WO | WO2017/087380 A1 | 5/2017 |
| WO | WO2017/120453 A1 | 7/2017 |
| WO | WO2017/133425 A1 | 8/2017 |
| WO | WO2017/134657 A1 | 8/2017 |
| WO | WO2017/139113 A1 | 8/2017 |
| WO | WO2017/139246 A1 | 8/2017 |
| WO | WO2017/147082 A1 | 8/2017 |
| WO | WO2017/147103 A1 | 8/2017 |
| WO | WO2017/147291 A1 | 8/2017 |
| WO | WO2017/151987 A1 | 9/2017 |
| WO | WO2017/156386 A1 | 9/2017 |
| WO | WO2017/159849 A1 | 9/2017 |
| WO | WO2017/165372 A1 | 9/2017 |
| WO | WO2017/178904 A1 | 10/2017 |
| WO | WO2017/183124 A1 | 10/2017 |
| WO | WO2017/190155 A2 | 11/2017 |
| WO | WO2017/192119 A1 | 11/2017 |
| WO | WO2017/196271 A1 | 11/2017 |
| WO | WO2017/205909 A1 | 12/2017 |
| WO | WO2017/210318 A2 | 12/2017 |
| WO | WO2017/214118 A1 | 12/2017 |
| WO | WO2017/214183 A1 | 12/2017 |
| WO | WO2017/217946 A1 | 12/2017 |
| WO | WO2018/007120 A1 | 1/2018 |
| WO | WO2018/007471 A1 | 1/2018 |
| WO | WO2018/017678 A1 | 1/2018 |

(56) References Cited

FOREIGN PATENT DOCUMENTS

| | | |
|---|---|---|
| WO | WO2018/017683 A1 | 1/2018 |
| WO | WO2018/017716 A1 | 1/2018 |
| WO | WO2018/026764 A1 | 2/2018 |
| WO | WO2018/026769 A1 | 2/2018 |
| WO | WO2018/031741 A1 | 2/2018 |
| WO | WO2018/035069 A1 | 2/2018 |
| WO | WO2018/039124 A1 | 3/2018 |
| WO | WO2018/039326 A1 | 3/2018 |
| WO | WO2018/041963 A1 | 3/2018 |
| WO | WO2018/045299 A1 | 3/2018 |
| WO | WO2018/051091 A1 | 3/2018 |
| WO | WO2018/052482 A1 | 3/2018 |
| WO | WO2018/057482 A1 | 3/2018 |
| WO | WO2018/057563 A1 | 3/2018 |
| WO | WO2018/061002 A1 | 4/2018 |
| WO | WO2018/064437 A1 | 4/2018 |
| WO | WO2018/067410 A1 | 4/2018 |
| WO | WO2018/073150 A1 | 4/2018 |
| WO | WO2018/078370 A1 | 5/2018 |
| WO | WO2018/078615 A1 | 5/2018 |
| WO | WO2018/082987 A1 | 5/2018 |
| WO | WO2018/088939 A1 | 5/2018 |
| WO | WO2018/089970 A1 | 5/2018 |
| WO | WO2018/093663 A1 | 5/2018 |
| WO | WO2018/096531 A1 | 5/2018 |
| WO | WO2018/118756 A1 | 6/2018 |
| WO | WO2018/132181 A1 | 7/2018 |
| WO | WO2018/132182 A1 | 7/2018 |
| WO | WO2018/135477 A1 | 7/2018 |
| WO | WO2018/135478 A1 | 7/2018 |
| WO | WO2018/136592 A2 | 7/2018 |
| WO | WO2018/139508 A1 | 8/2018 |
| WO | WO2018/145434 A1 | 8/2018 |
| WO | WO2018/146045 A1 | 8/2018 |
| WO | WO2018/146170 A1 | 8/2018 |
| WO | WO2018/146173 A1 | 8/2018 |
| WO | WO2018/146177 A1 | 8/2018 |
| WO | WO2018/148456 A1 | 8/2018 |
| WO | WO2018/156524 A1 | 8/2018 |
| WO | WO2018/158636 A1 | 9/2018 |
| WO | WO2018/177344 A1 | 10/2018 |
| WO | WO2018/178939 A1 | 10/2018 |
| WO | WO2018/183128 A1 | 10/2018 |
| WO | WO2018/187576 A2 | 10/2018 |
| WO | WO2018/226991 A1 | 12/2018 |
| WO | WO2019/094963 A1 | 5/2019 |
| WO | WO2019/158996 A1 | 8/2019 |
| WO | WO2020/028537 A1 | 2/2020 |
| WO | WO2020/0234785 A1 | 11/2020 |
| WO | WO2020/247612 A1 | 12/2020 |
| WO | WO2021/026469 A1 | 2/2021 |
| WO | WO2021/026472 A1 | 2/2021 |
| WO | WO2021/062260 A1 | 4/2021 |
| WO | WO2021/062265 A1 | 4/2021 |
| WO | WO2021/062270 A1 | 4/2021 |
| WO | WO2021/119478 A1 | 6/2021 |
| WO | WO2021/127503 A1 | 6/2021 |
| WO | WO2021/158967 A1 | 8/2021 |
| WO | WO2021/195617 A1 | 9/2021 |
| WO | WO2021/222403 A1 | 11/2021 |
| WO | WO2021/231574 A1 | 11/2021 |
| WO | WO2021/243263 A1 | 12/2021 |

OTHER PUBLICATIONS

Ryan et al.; U.S. Appl. No. 17/632,554 entitled "Catheter blood pump delivery, guiding systems and methods of use," filed Feb. 3, 2022.

Jagani et al.; Dual-propeller cavopulmonary pump for assisting patients with hypoplastic right ventricle; ASAIO Journal (American Society for Artificial Internal Organs): 10 pages; DOI: 10.1097/MAT.0000000000000907; Jan. 2019.

Park et al.; Biologically Inspired, Open, Helicoid Impeller Design for Mechanical Circulatory Assist; ASAIO Journal (American Society for Artificial Internal Organs); DOI: 10.1097/MAT.0000000000001090; Oct. 23, 2019.

Reitan et al.; First human use of the reitan catheter pump; Asaio Journal; 47(2); p. 124; Mar.-Apr. 2001.

Calomeni et al.; U.S. Appl. No. 16/927,705 entitled "Intravascular blood pumps and methods of manufacture and use," filed Jul. 13, 2020.

Calomeni et al.; U.S. Appl. No. 16/988,221 entitled "Catheter blood pumps and collapsible pump housings," filed Aug. 7, 2020.

Saul et al.; U.S. Appl. No. 17/264,927 entitled "Intravascaular blood pumps and methods of use," filed Feb. 1, 2021.

Hildebrand et al.; U.S. Appl. No. 17/615,685 entitled "Catheter blood pumps and methods of use and manufacture," filed Dec. 1, 2021.

Salahieh et al.; U.S. Appl. No. 17/552,311 entitled "Intravascular blood pumps and methods of use and manufacture," filed Dec. 15, 2021.

Calomeni et al.; U.S. Appl. No. 17/033,455 entitled "Catheter blood pump and collapsible blood conduits," filed Sep. 25, 2020.

Wallin et al.; U.S. Appl. No. 17/033,482 entitled "Intravascular blood pump system and methods of use and control thereof," filed Sep. 25, 2020.

Dhaliwal et al.; U.S. Appl. No. 17/033,493 entitled "Catheter blood pumps and collapsible pump housings," filed Sep. 25, 2020.

Ryan et al.; U.S. Appl. No. 17/782,675 entitled "Intravascular blood pumps, motors, and fluid control," filed Jun. 6, 2022.

Robinson et al.; U.S. Appl. No. 17/784,758 Descending aorta and vena cava blood pumps,: filed Jun. 13, 2022.

Varghai et al.; U.S. Appl. No. 17/794,002 entitled "Intravascular blood pumps, motors, and fluid control," filed Jul. 20, 2022.

* cited by examiner

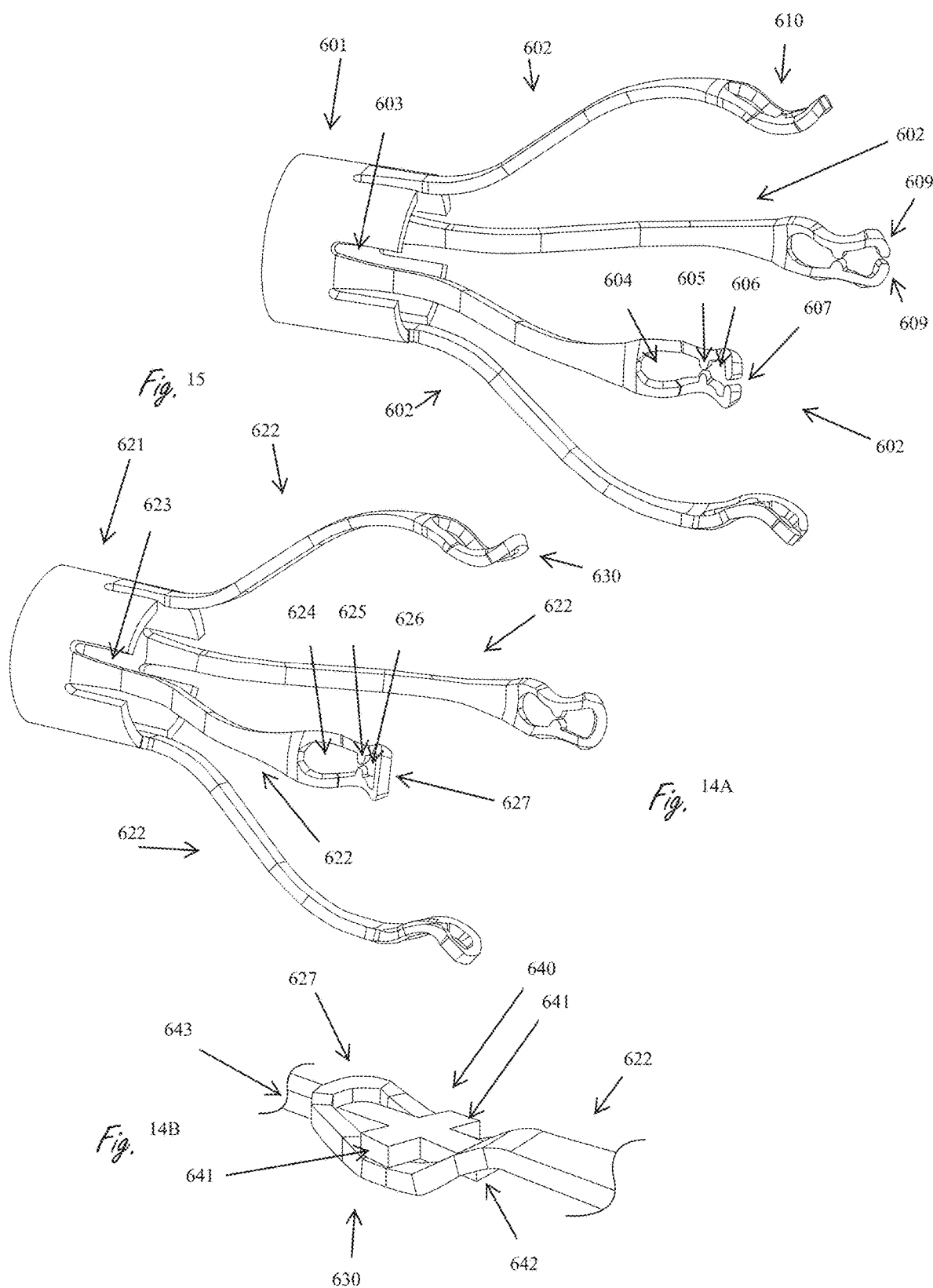

INTRAVASCULAR BLOOD PUMPS WITH STRUTS AND METHODS OF USE AND MANUFACTURE

CROSS REFERENCE TO RELATED APPLICATIONS

This application claims priority to U.S. Provisional Application No. 62/877,154, filed Jul. 22, 2019, which is incorporated by reference herein in its entirety for all purposes.

This application is related to and incorporates by reference herein for all purposes the disclosures of the following applications: WO2018/226991, WO2019/094963, WO2019/152875, and WO2020/028537.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

This disclosure is related to pump portions of catheter blood pumps, and their use and manufacture.

One aspect of the disclosure is a catheter blood pump, comprising: an expandable pump portion extending distally from an elongate shaft. The pump portion includes an expandable impeller housing. The housing includes an expandable blood conduit defining a blood lumen, and a plurality of struts coupled to and extending axially from an end region of the expandable blood conduit, where the plurality of struts non-unitary with the expandable blood conduit. The pump portion also includes one or more expandable impellers.

In this aspect the plurality of expandable struts may be coupled to an expandable scaffold at the end region of the expandable blood conduit.

In this aspect the plurality of expandable struts may be disposed at an outflow of the pump portion. In this aspect the plurality of expandable struts may be disposed at an inflow of the pump portion.

In this aspect the plurality of expandable struts may be proximal relative to a proximal end of the expandable blood conduit. The plurality of expandable struts may be disposed at an inflow of the pump portion.

In this aspect the plurality of expandable struts may be disposed distal relative to a distal end of the expandable blood conduit.

In this aspect the blood pump may further comprise a second plurality of struts extending axially from a second end region of the expandable blood conduit. The second plurality of struts may be unitary or non-unitary with the scaffold. In this aspect the scaffold may extend from the end region to a second end region. In this aspect the scaffold may be continuous from the end region to a second end region. In this aspect the scaffold may include one or more discontinuities between the end region and the second end region.

In this aspect the scaffold may include first and second scaffold sections axially spaced apart. First and second scaffold sections may be disposed at first and second impeller regions. In this aspect the blood conduit may include a central region in between first and second scaffold sections, wherein the central region is void of a scaffold.

In this aspect the plurality of expandable struts may be disposed at an outflow of the pump portion and a second plurality of expandable struts may be disposed at an inflow of the pump portion. The plurality of expandable struts may be disposed at an inflow of the pump portion and a second plurality of expandable struts may be disposed at an outflow of the pump portion.

In this aspect the plurality of expandable struts may have a dimension that is different than a dimension of an end region of the scaffold. In some examples the struts have a radial thickness greater than a radial thickness of the scaffold in the end region. In some examples the struts have a width greater than a width of the scaffold in the end region.

In this aspect the plurality of expandable struts and the scaffold comprise the same material, such as a metallic alloy such as nitinol.

In this aspect the plurality of expandable struts extend from a common strut hub, wherein a strut hub and the plurality of expandable struts may be unitary.

In this aspect each of the plurality of struts may have a stiffness that is greater than a region of the scaffold to which it is coupled.

In this aspect the expandable blood conduit may further comprises a membrane secured to the scaffold. A membrane herein may comprise one or more polymeric layers.

In this aspect the plurality of struts may each have a first securing member secured to a second securing member of the scaffold. A first securing member may be disposed at an end region of the strut. A first securing member may comprise a bend in the strut. A first securing member may include one or more projections that project away from an elongate strut body. A first securing member may have a T configuration. A first securing member may have a hook configuration. A second securing member may comprise a bend in the scaffold. A second securing member may have a valley configuration in the scaffold. A first securing member may comprise an opening in the strut.

In this aspect the plurality of struts may each have closed free ends.

In this aspect the plurality of struts have each have open free ends, optionally including a plurality of fingers that define the open end.

In this aspect first securing members may comprise one or more projections extending from side arms of the strut, the projections optionally partially defining an opening in the strut.

In this aspect first securing members may have a valley configuration comprising a bend.

In this aspect a second securing member may comprise an elongate body that extends at least partially within a strut opening.

In this aspect a first securing member and a second securing member may be separately and together sized, positioned, and configured to engage one another such that one or more surfaces on each interact and cause a resistance to movement of one or both of the first and securing members in at least one direction.

In this aspect the coupling between each of the plurality of struts and the end region comprises a weld.

In this aspect the plurality of struts includes from at least two to ten struts, optionally two to eight struts.

As used herein, a strut is generally described as a structure extending away from a structure to which it is coupled. Struts may comprise a main body, such as extending from a hub, and may become branched, such that there are more than one strut main bodies. The branched regions of the strut are generally considered part of the strut.

In this aspect any of the blood pumps may be manufactured, wherein the manufacture includes coupling each of the plurality of struts to the end region of the blood conduit, and optionally to a scaffold of the blood conduit. Scaffolds herein may be formed from a variety of materials or combinations thereof, such a metals, alloys, polymers, etc.

One aspect of the disclosure is a method of manufacturing a pump portion of a catheter blood pump, such as any of the pump portions herein.

This aspect may include coupling each of a plurality of struts to an end region of an expandable scaffold, the expandable scaffold part of an expandable blood conduit that defines a blood lumen, and positioning one or more collapsible impellers at least partially within the blood lumen.

In this aspect, the method may further comprise securing a membrane to the expandable scaffold prior in time to the coupling step. Securing a membrane to the expandable scaffold may be performed on a mandrel.

In this aspect, the method may further comprise coupling each of a second plurality of struts to a second end region of an expandable scaffold.

In this aspect, the coupling step may comprise coupling each of the plurality of struts that extend from a unitary hub to the end region of the expandable scaffold.

In this aspect, positioning the one or more impellers may occur prior in time to coupling each of the plurality of struts to the end region of the expandable scaffold.

In this aspect, the coupling step may comprise coupling each of a plurality of struts to an end region of an expandable scaffold, wherein the expandable scaffold extends along the blood conduit.

In this aspect, the coupling step may comprise coupling each of a plurality of struts to a first scaffold section that is axially spaced from a second scaffold section. The method may further comprise coupling each of a second plurality of struts to the second scaffold section. In this aspect, coupling each of a second plurality of struts to a second end region of an expandable scaffold may comprise coupling each of the second plurality of struts to a second scaffold section of the expandable scaffold.

In this aspect, coupling each of a plurality of struts to an end region of an expandable scaffold may comprise coupling each of a plurality of struts to an end region of an expandable scaffold from which a second plurality of struts extend, wherein the second plurality of struts are unitary with the scaffold. Second plurality of struts may be unitary with a second scaffold section of the scaffold.

BRIEF DESCRIPTION OF THE DRAWINGS

FIG. 14A illustrates an exemplary strut assembly including a plurality of struts.

FIG. 14B illustrates an exemplary coupling of a strut and an end region of an expandable scaffold.

FIG. 15 illustrates an exemplary strut assembly including a plurality of struts.

DETAILED DESCRIPTION

The present disclosure is related to medical devices, systems, and methods of use and manufacture. Medical devices herein may include a distal pump portion (which may also be referred to herein as a working portion) adapted to be disposed within a physiologic vessel, wherein the distal pump portion includes one or more components that act upon fluid. For example, pump portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein.

Figure 1:
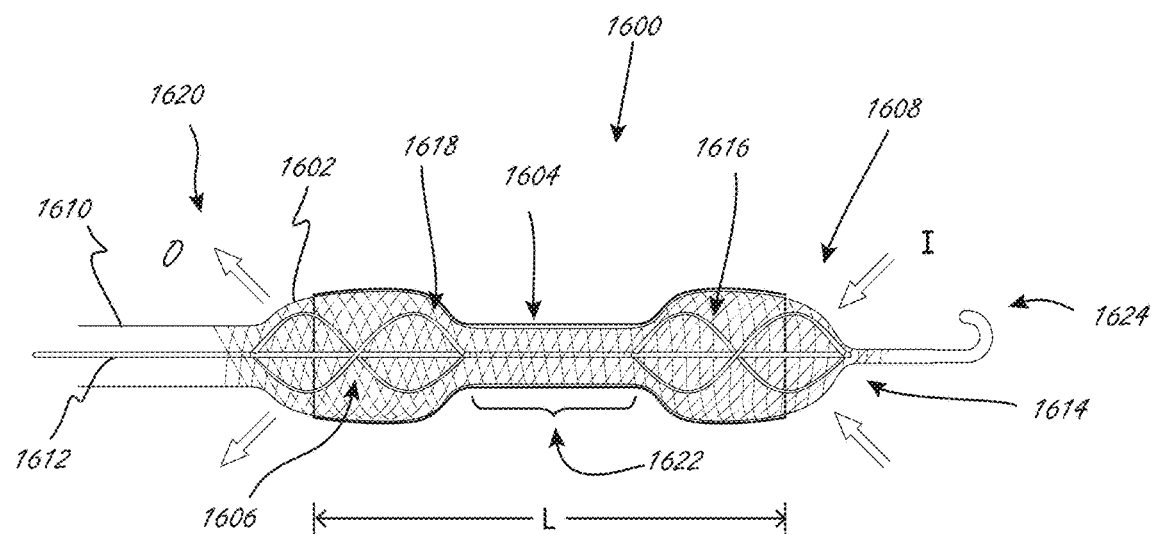
FIG. 1 is a side view of an exemplary expandable pump portion that includes an expandable impeller housing, blood conduit and a plurality of impellers.

FIG. 1 is a side view illustrating a distal portion of an exemplary catheter blood pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can be attached to drive mechanism 1612 (e.g., a drive cable). Drive mechanism 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member or expandable scaffold 1602, which in this embodiment has a proximal end 1620 that extends further proximally than a proximal end of proximal impeller 1606, and a distal end 1608 that extends further distally than a distal end 1614 of distal impeller 1616. Expandable members may also be referred to as expandable scaffolds herein. Expandable scaffold 1602 is disposed radially outside of the impellers along the axial length of the impellers. Expandable scaffold 1602 can be constructed in a manner and made from materials similar to many types of expandable structures that are known in the medical arts to be able to be collapsed and expanded, examples of which are provided herein. Examples of suitable materials include, but are not limited to, polyurethane and polyurethane elastomers.

Pump portion 1600 also includes blood conduit 1604, which is coupled to expandable member 1602, has a length L, and extends axially between the impellers. Conduit 1604 creates and provides a fluid lumen between the two impellers. When in use, fluid move through the lumen provided by conduit 1604. The conduits herein are non-permeable, or they can be semipermeable, or even porous as long as they can still define a lumen. The conduits herein are also flexible, unless it is otherwise indicated. The conduits herein extend completely around (i.e., 360 degrees) at least a portion of the pump portion. In pump portion 1600, conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "0." Conduit 1604 improves impeller pumping dynamics, compared to those that working portion 1600 would have without the conduit.

Expandable member 1602 may have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member as well as the struts herein include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive mechanism 1612 is co-axial with the longitudinal axis in this embodiment. In use, the central region can be placed across a valve, such as an aortic valve. In some embodiments, expandable member 1602 is adapted and constructed to expand to an outermost dimension of 12-24F (4.0-8.0 mm) where the impellers are axially within the expandable member, and to an outermost dimension of 10-20F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive mechanism 1612 rotate within the expandable member and conduit assembly. Drive mechanism 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or 8,052,749, the disclosures of which are incorporated by reference herein.

Figure 2:
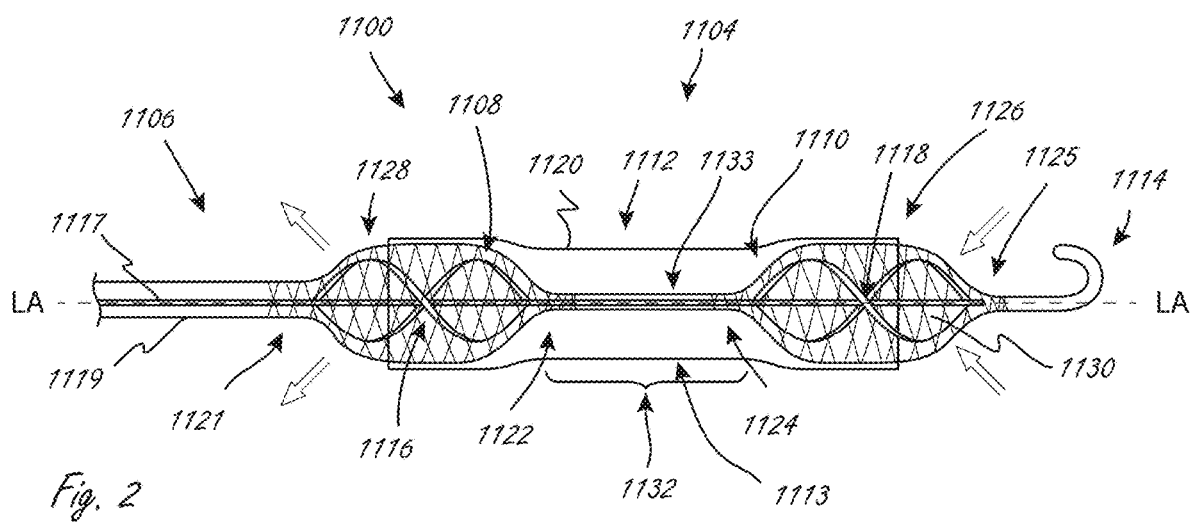
FIG. 2 is a side view of an exemplary expandable pump portion that includes an expandable impeller housing, a blood conduit, a plurality of impellers, and a plurality of expandable scaffolds sections or support members.

FIG. 2 is a side view illustrating a deployed configuration (shown extracorporally) of a distal portion of an exemplary embodiment of a catheter blood pump. Exemplary blood pump 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable scaffold or member 1108 and second expandable scaffold or member 1110, axially spaced apart along a longitudinal axis LA of working portion 1104. First scaffold 1108 and second scaffold 1110 (and any other separate scaffolds herein) may also be referenced as part of a common scaffold and referred to herein as scaffold sections. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes blood conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a blood conduit being coupled to an expandable scaffold or member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the blood conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the blood conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable scaffolds or members help maintain the blood conduit in an open configuration to create the lumen, while each also creates a working environment for an impeller, described below. Each of the expandable scaffolds, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841,976 or 8,052,749, the disclosures of which are incorporated by reference herein for all purposes.

Figure 3A:
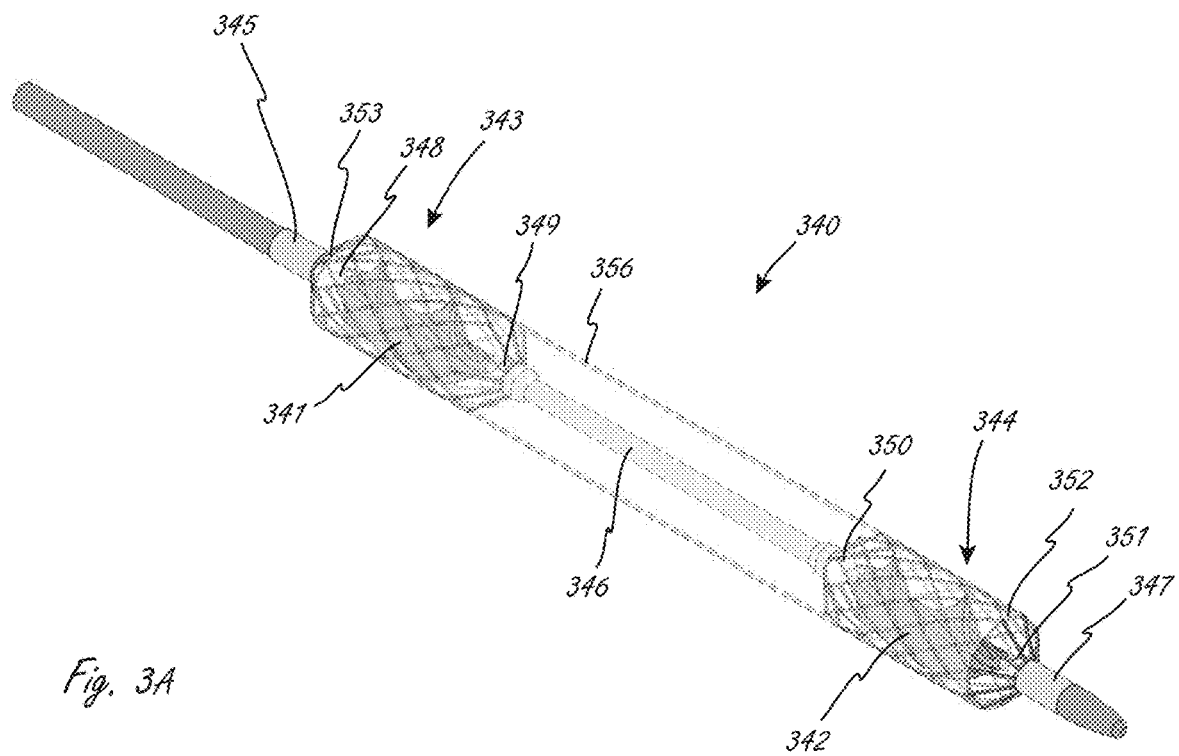
FIGS. 3A, 3B, 3C and 3D illustrate an exemplary expandable pump portion that includes a blood conduit, a plurality of impellers, and a plurality of expandable scaffold sections or support members.
Figure 3B:
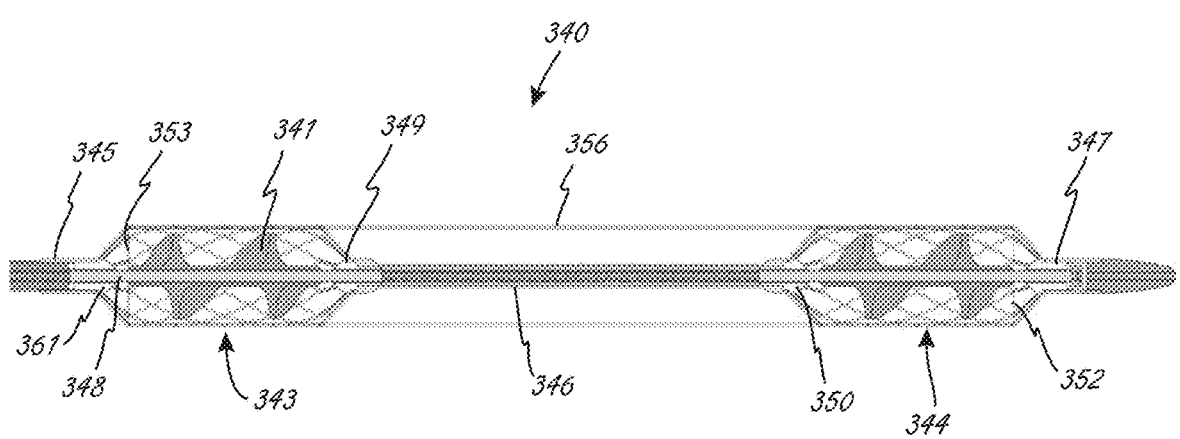
Figure 3C:
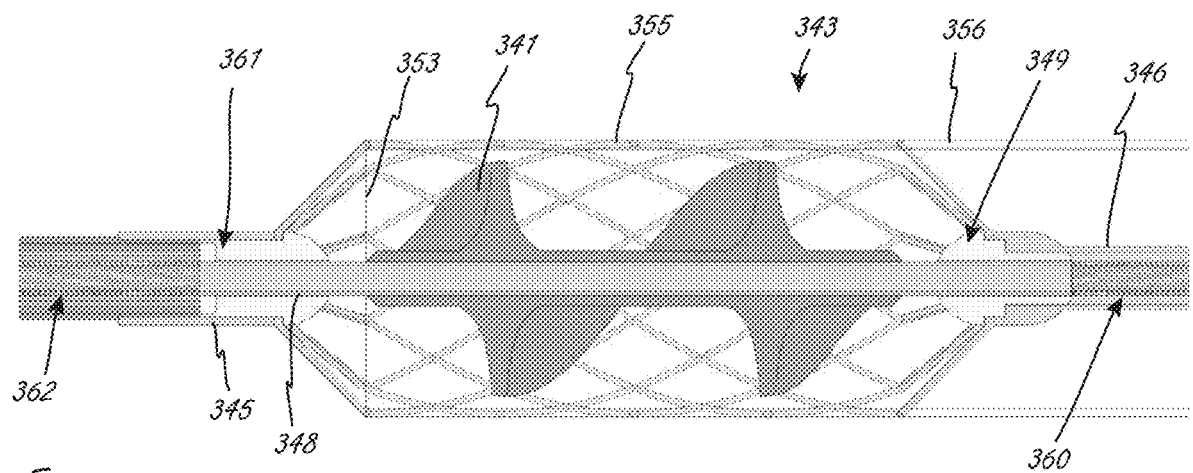
Figure 3D:
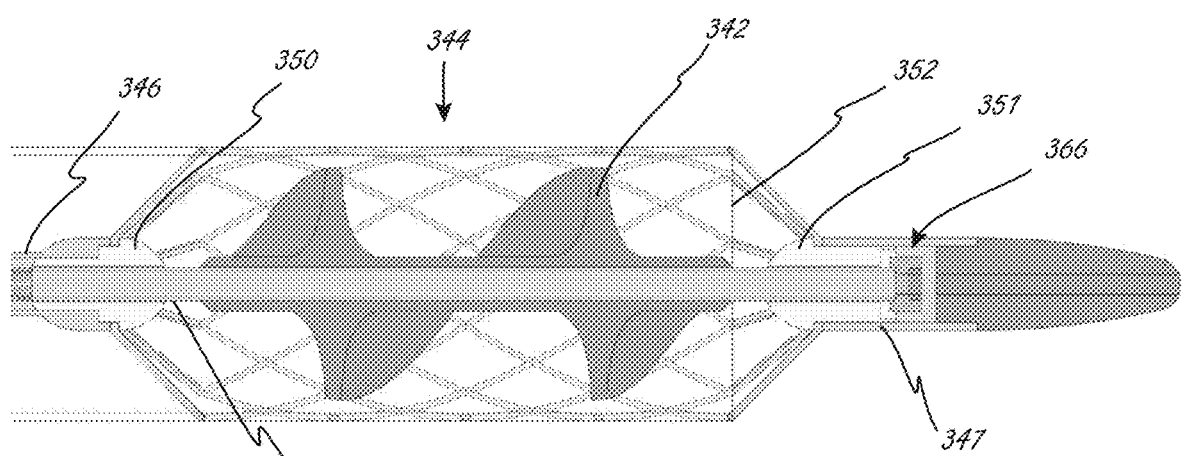

FIGS. 3A-3D show an exemplary pump portion that is similar in some ways to the pump portion shown in FIG. 2. Pump portion 340 is similar to pump portion 1104 in that in includes two expandable members axially spaced from one another when the pump portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Pump portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Pump portion 340 includes proximal expandable scaffold 343 and distal expandable scaffold 344, each of which extends radially outside of one of the impellers. The expandable scaffolds have distal and proximal ends that also extend axially beyond distal and proximal ends of the impellers, which can be seen in FIGS. 3B-3D. Coupled to the two expandable scaffolds is blood conduit 356, which has a proximal end 353 and a distal end 352. The two expandable scaffolds each include a plurality of proximal struts and a plurality of distal struts. The proximal struts in proximal expandable scaffold 343 extend to and are secured to shaft section 345, which is coupled to bearing 361, through which the drive cable extends and is configured and sized to rotate. The distal struts of proximal expandable scaffold 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts extend axially from distal expandable scaffold 344 to and are secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts extend from the distal expandable scaffold extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
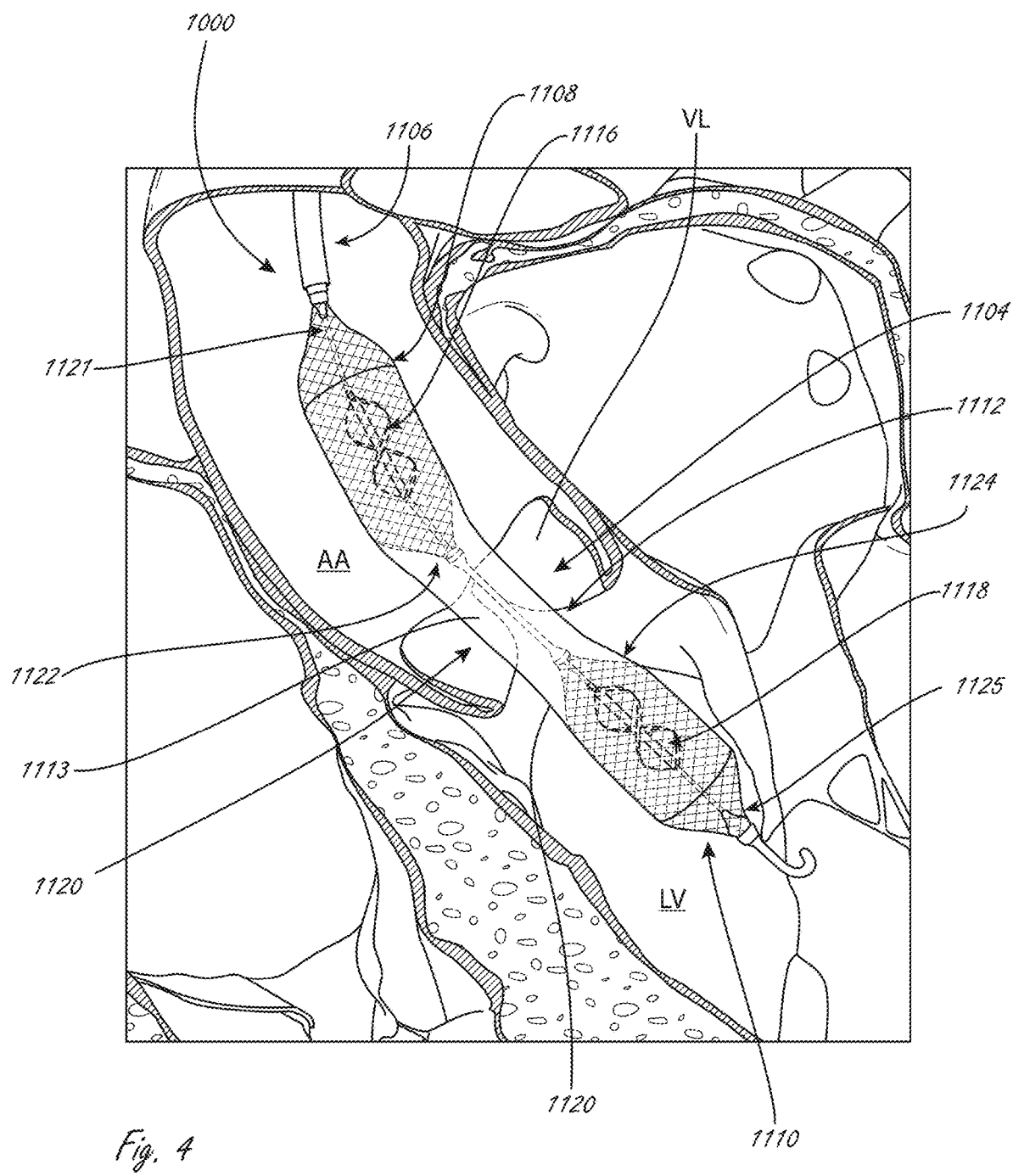
FIG. 4 illustrates an exemplary target location of an expandable pump portion, the pump portion including a blood conduit, a plurality of expandable scaffold sections or support members, and a plurality of impellers.

FIG. 4 illustrates an exemplary placement of pump portion 1104 from catheter blood pump 1000 from FIG. 2. Once difference shown in FIG. 4 is that the conduit extends at least as far as the ends of the impellers, like in FIGS. 3A-3D. FIG. 4 shows pump portion 1104 in a deployed configuration, positioned in place across an aortic valve. Pump portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable scaffold 1110, with continued proximal movement allowing first expandable scaffold 1108 to expand.

In this embodiment, second expandable scaffold 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable scaffolds 1108 and 1110 causes blood conduit 1112 to assume a more open configuration, as shown in FIG. 4. Thus, while in this embodiment conduit 1112 does not have the same self-expanding properties as the expandable scaffolds, the conduit will assume a deployed, more open configuration when the working end is deployed. At least a portion of central region 1113 of conduit 1112 is positioned at an aortic valve coaptation region and engages leaflets. In FIG. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable scaffold 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of pump portion 1104, the position of the pump portion can be assessed in any way, such as under fluoroscopy. The position of the pump portion can be adjusted at any time during or after deployment. For example, after second expandable scaffold 1110 is released but before first expandable member 1108 is released, pump portion 1104 can be moved axially (distally or proximally) to reposition the pump portion. Additionally, for example, the pump portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9F sheath and still obtain high enough flow rates when in use, which is not possible with some products currently in development and/or testing. For example, some products are too large to be able to be reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
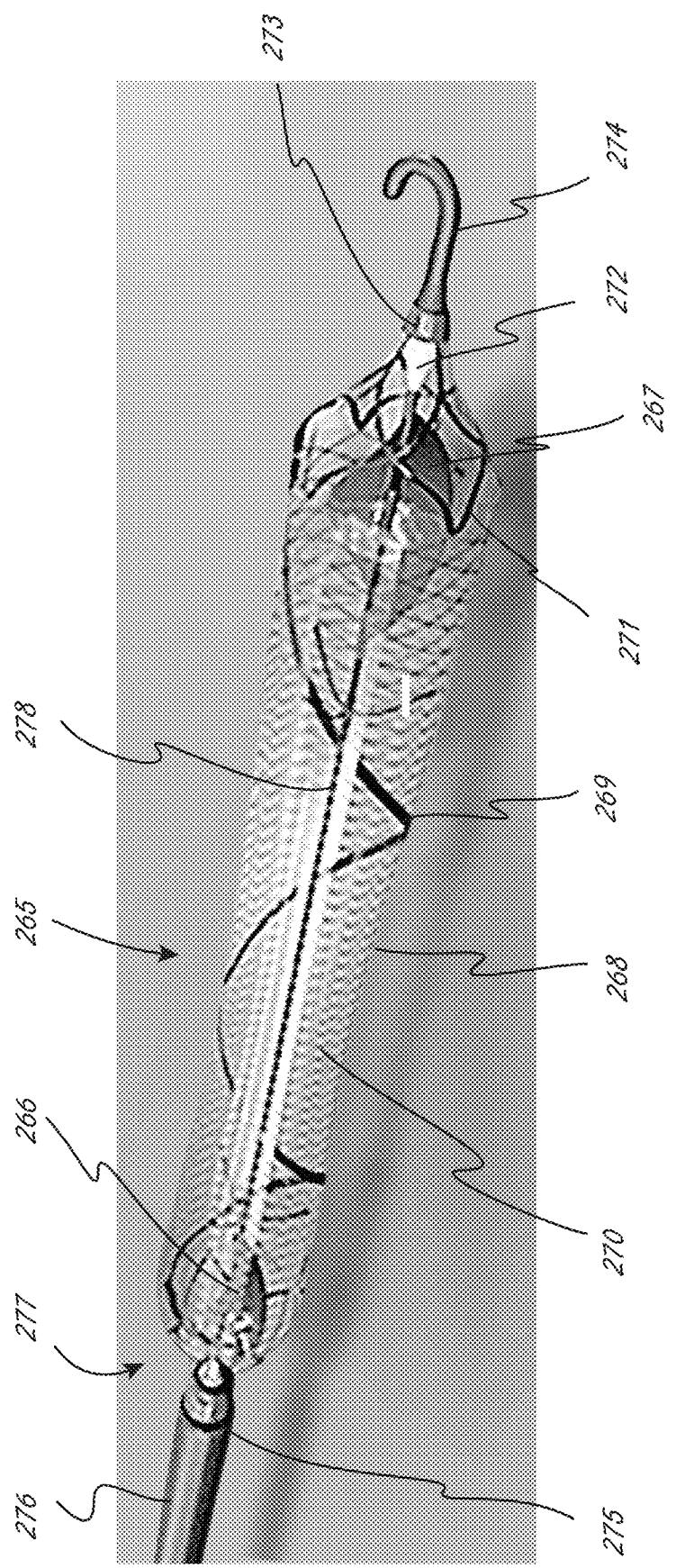
FIG. 5 illustrates an exemplary pump portion including an expandable impeller housing, a blood conduit, and a plurality of impellers.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable scaffold or member, referred to 270 generally, and blood conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the blood conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable. Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit may extend radially within the expandable member so that inner surface of the conduit is radially within the expandable member where it is secured to the expandable member.

Any of the expandable scaffolds or member(s) herein may be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable scaffold or member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figure 6A:
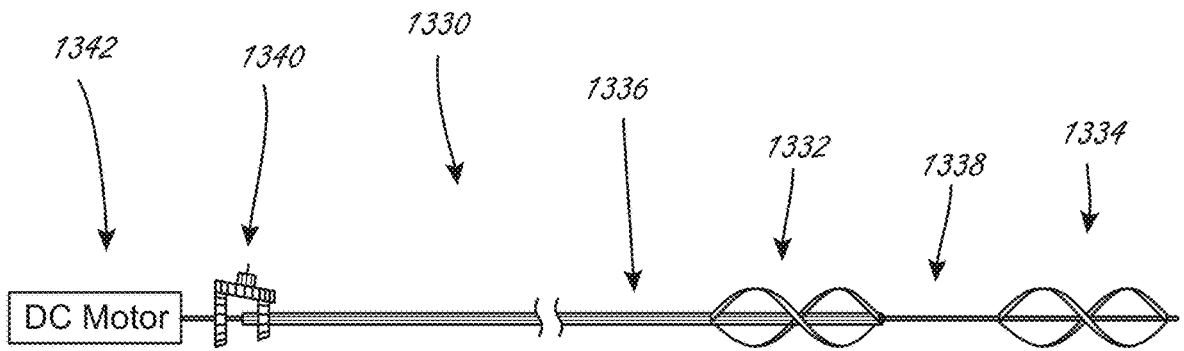
FIG. 6A illustrates at least a portion of an exemplary catheter blood pump that includes a pump portion, wherein at least two different impellers can be rotated at different speeds.

In any of the embodiments herein in which the catheter blood pump includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

Figure 6B:
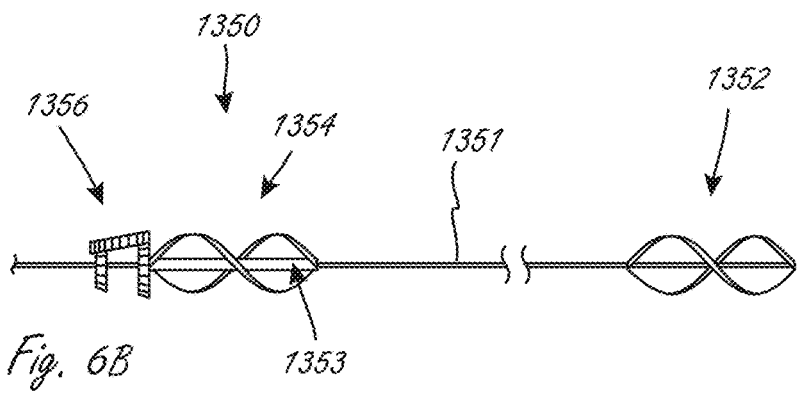
FIG. 6B illustrates at least a portion of an exemplary catheter blood pump that includes a pump portion, where at least two different impellers can be rotated at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

Figure 7:
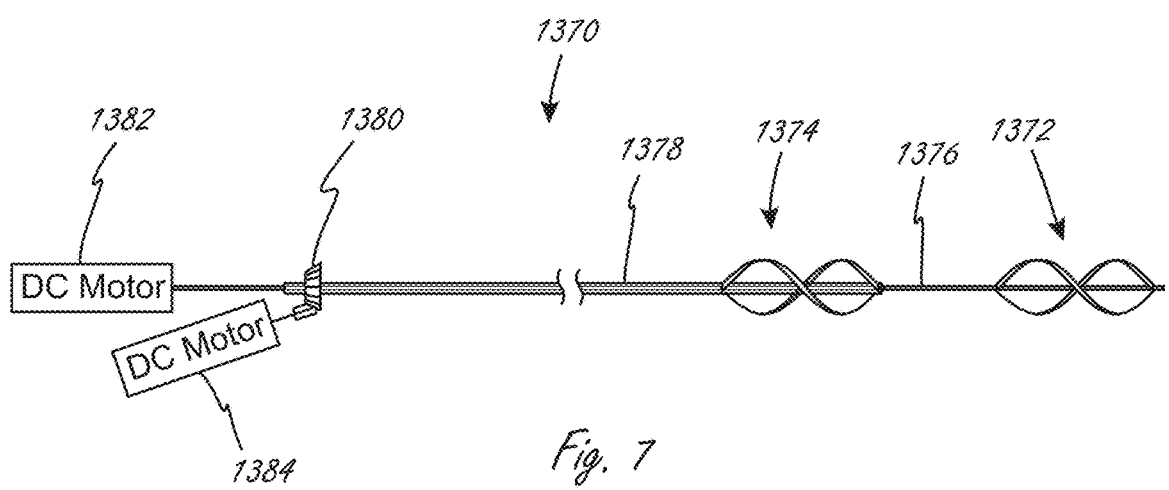
FIG. 7 illustrates a portion of an exemplary catheter blood pump that includes a pump portion.

FIG. 7 illustrates an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

Figure 6C:
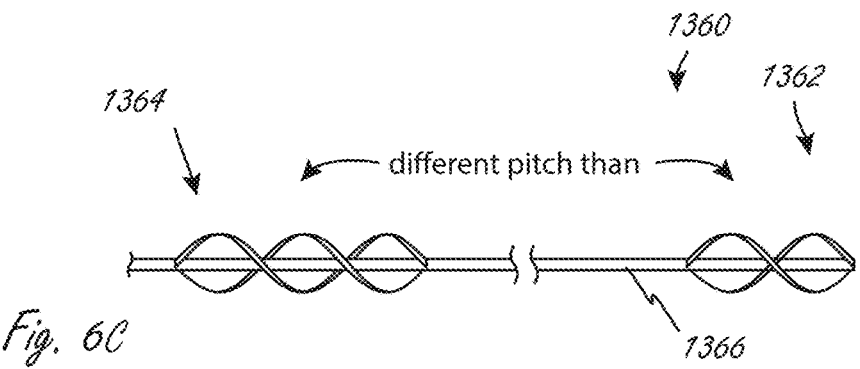
FIG. 6C illustrates at least a portion of an exemplary catheter blood pump that includes a pump portion with at least two impellers having different pitches.

In some embodiments, a common drive mechanism (e.g., cable and/or shaft) can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion may have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figure 8:
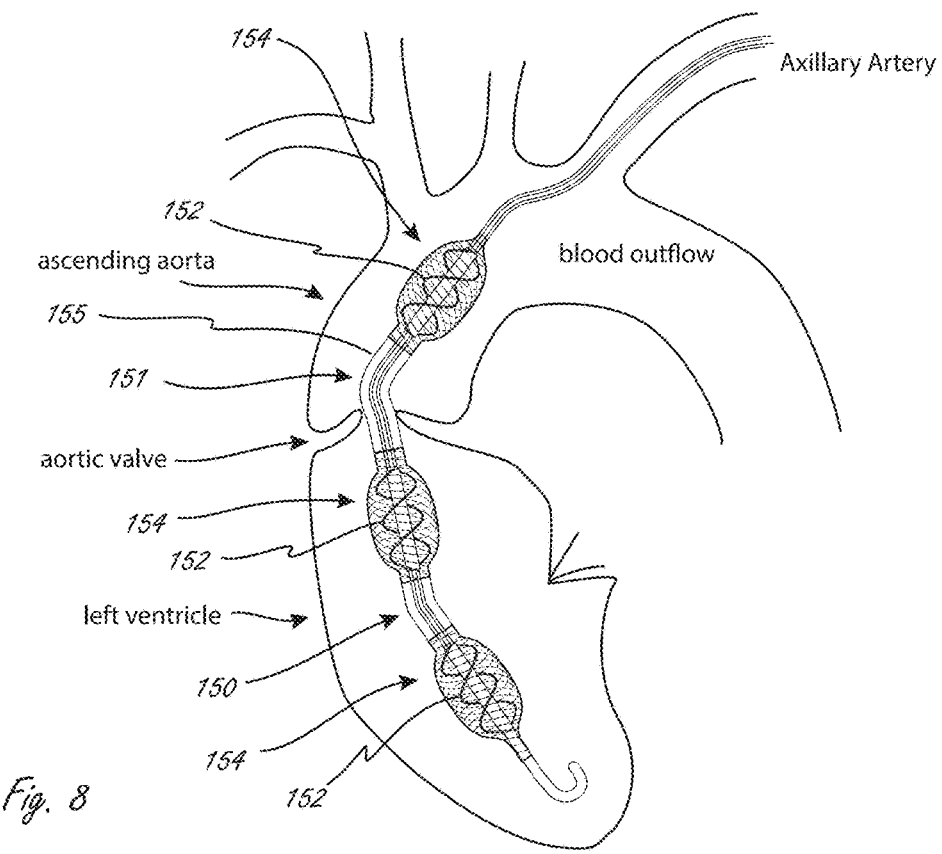
FIG. 8 illustrates an exemplary expandable pump portion including a plurality of expandable impellers, including one or more bends formed therein between adjacent impellers.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 150 or 151 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. It will be appreciated from the description herein, however, that the pump may be introduced and tracked into position in various manners including a femoral approach over the aortic arch.

One aspect of the disclosure is a catheter blood pump that includes a distal impeller axially spaced from a proximal impeller. Distal and proximal impellers may be axially spaced from each other. For example, the distal and proximal impellers may be connected solely by their individual attachment to a common drive mechanism. This is different from a single impeller having multiple blade rows or sections. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. I t can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

Figure 9:
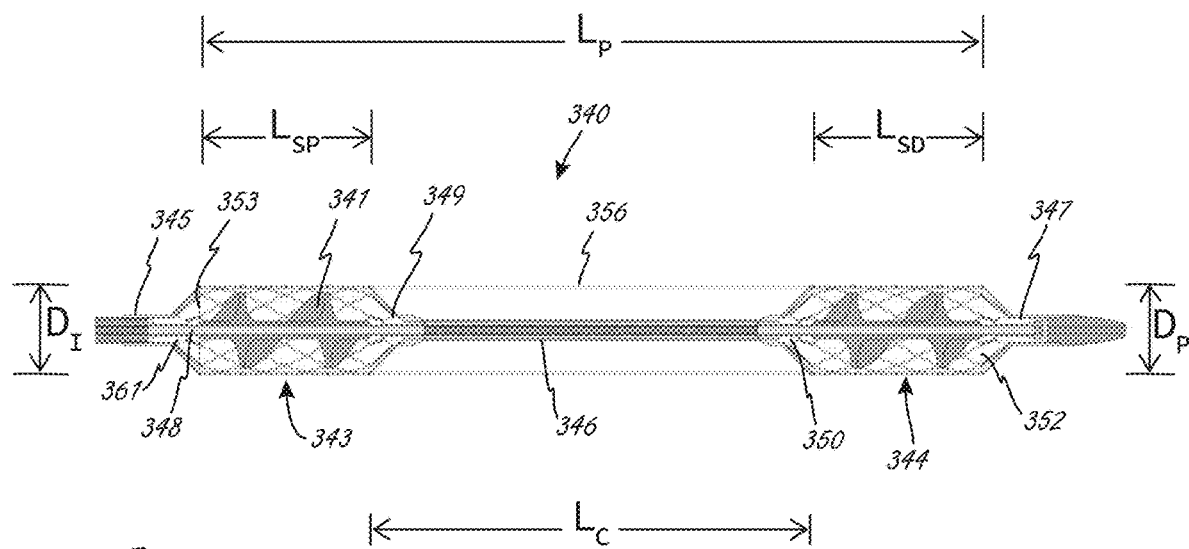
FIG. 9 illustrates an exemplary expandable pump portion comprising a plurality of impellers and a blood conduit.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 cm to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein that includes multiple impellers, the axial spacing between impellers (along the length of the pump portion, even if there is a bend in the pump portion) can be from 2 mm to 100 mm, or any combination of upper and lower limits inclusive of 5 and 100 mm (e.g., from 10 mm-80 mm, from 15 mm-70 mm, from 20 mm-50 mm, 2 mm-45 mm, etc.).

Any of the pump portions herein that include a plurality of impellers may also include more than two impellers, such as three, four, or five impellers (for example).

Figure 10:
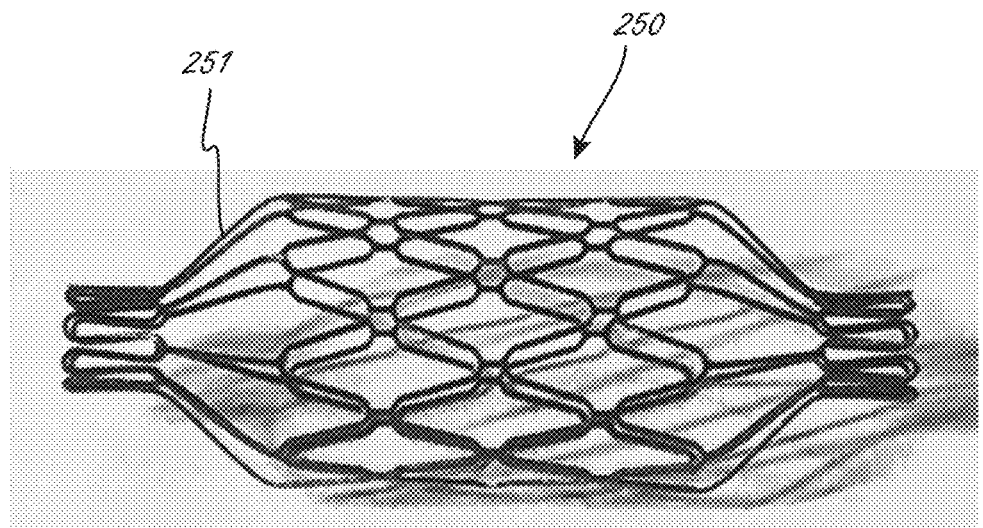
FIG. 10 illustrates an exemplary scaffold design and exemplary struts.

FIG. 10 illustrates an expandable scaffold 250 that may be one of at least two expandable scaffolds of a pump portion, such as the expandable scaffolds in FIGS. 3A-3D, wherein each expandable scaffold at least partially surrounds an impeller. The scaffold design in FIG. 10 has proximal struts 251 (only one labeled) extending axially therefrom. Having a separate expandable scaffold 250 for each impeller provides for the ability to have different geometries for any of the individual impellers. Additionally, this design reduces the amount of scaffold material (e.g., Nitinol) over the length of the expandable blood conduit, which may offer increased tracking when sheathed. A potential challenge with these designs may include creating a continuous membrane between the expandable scaffolds in the absence of an axially extending scaffolding material (see FIG. 3A). Any other aspect of the expandable scaffolds or members herein, such as those described in FIGS. 3A-3D, may be incorporated by reference into this exemplary design. Struts 251 may be disposed at a pump inflow or outflow. Struts 251 may be proximal struts or they may be distal struts.

Figure 11:
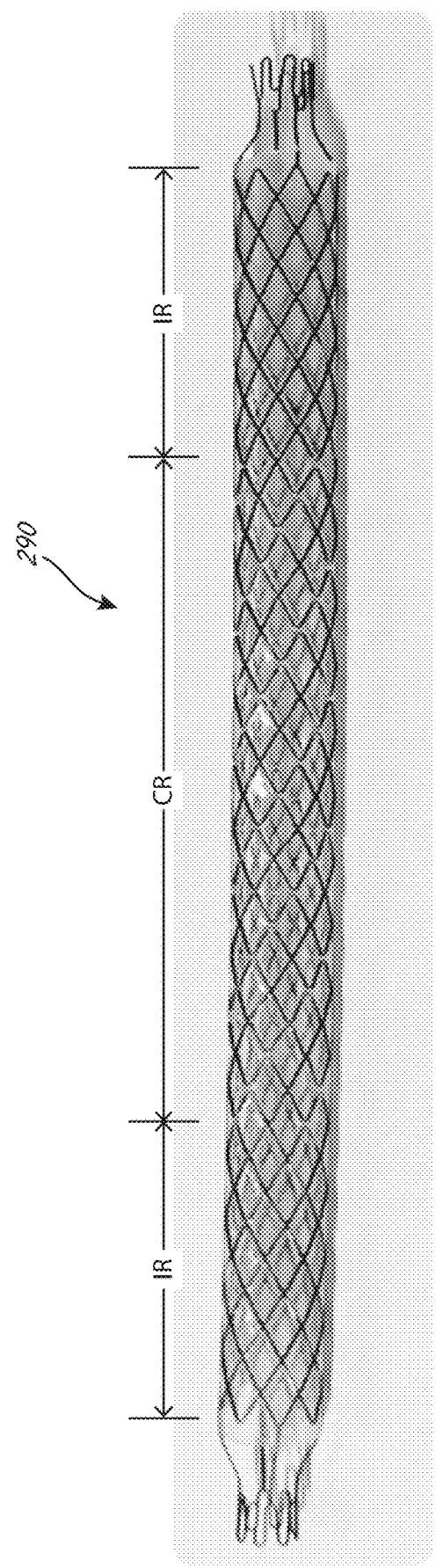
FIG. 11 illustrate an exemplary scaffold design and exemplary struts.

FIG. 11 show an exemplary scaffold along an length of the blood conduit. Central region "CR" may be axially between proximal and distal impellers. Central region "CR" flexibility is increased relative to scaffold impeller regions "IR" due to breaks or discontinuities in the scaffold pattern in the central region. The scaffold has relatively more rigid impeller sections "IR" adjacent the central region where impellers may be disposed (not shown). The relatively increased rigidity in the impeller regions IR may help maintain tip gap and impeller concentricity. This pump scaffold pattern provides for a flexibility distribution, along its length, of a proximal section of relatively less flexibility ("IR"), a central region "CR" of relatively higher flexibility, and a distal section "IR" of relatively less flexibility than the central region. The relatively less flexible sections (i.e., the two IR regions) are where proximal and distal impellers may be disposed (not shown but other embodiments are fully incorporated herein in this regard), with a relatively more flexible region in between. Exemplary benefits of the relative flexibility in these respective sections are described elsewhere herein. FIG. 11 is an example of a scaffold that is continuous from a first end region to a second end region, even though there are breaks or discontinuities in some locations of the scaffold. There is at least one line that can be traced along a continuous structural path from a first end region to a second end region.

The following disclosure provides exemplary method steps that may be performed when using any of the blood pumps, or portions thereof, described herein. It is understood that not all of the steps need to be performed, but rather the steps are intended to be an illustrative procedure. It is also intended that, if suitable, in some instances the order of one or more steps may be different. Before use, the blood pump can be prepared for use by priming the lumens (including any annular spaces) and pump assembly with sterile solution (e.g., heparinized saline) to remove any air bubbles from any fluid lines. The catheter, including any number of purge lines, may then be connected to a console. Alternatively, the catheter may be connected to a console and/or a separate pump that are used to prime the catheter to remove air bubbles.

Figure 12A:
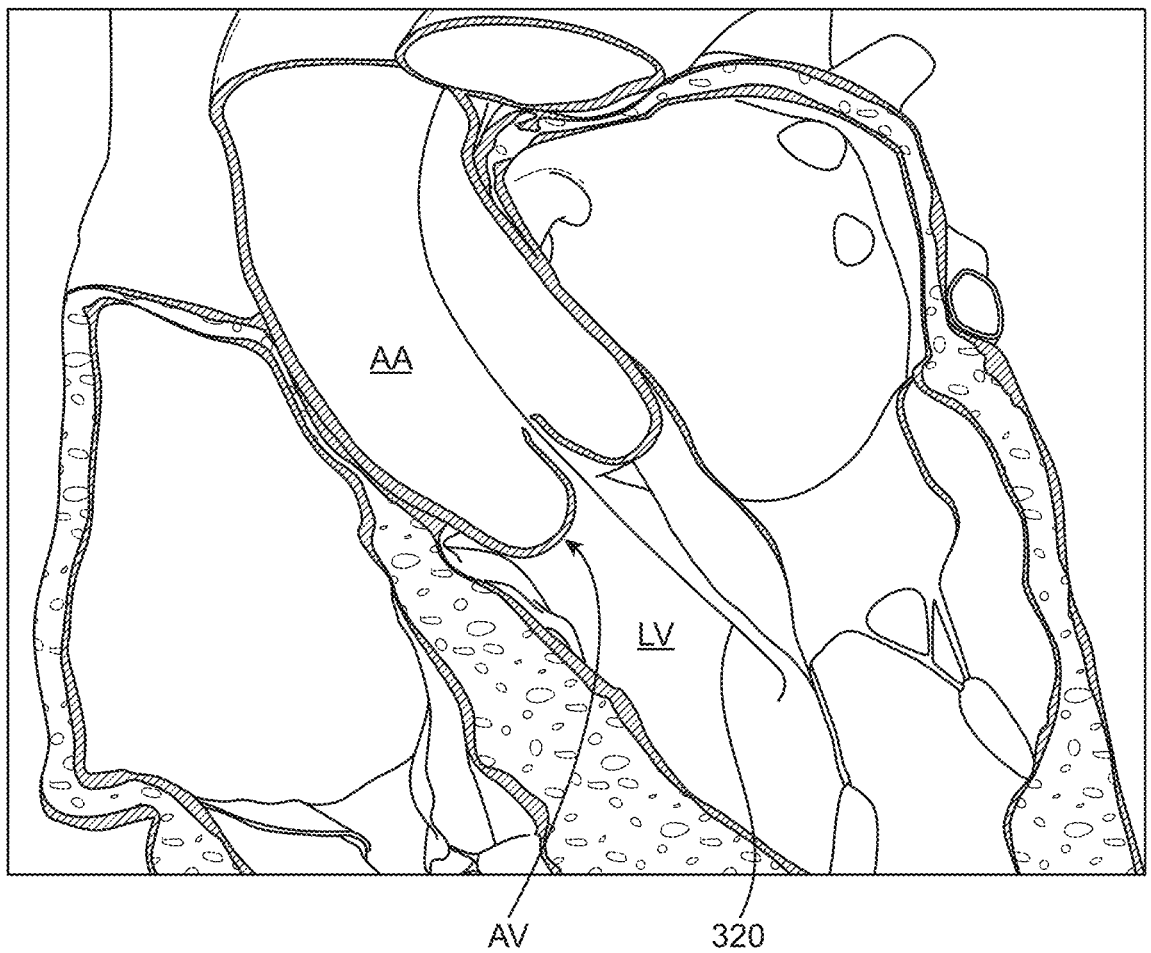
FIGS. 12A-12F illustrate an exemplary sequence of steps that may be performed to deploy an exemplary pump portion of a catheter blood pump.
Figure 12B:
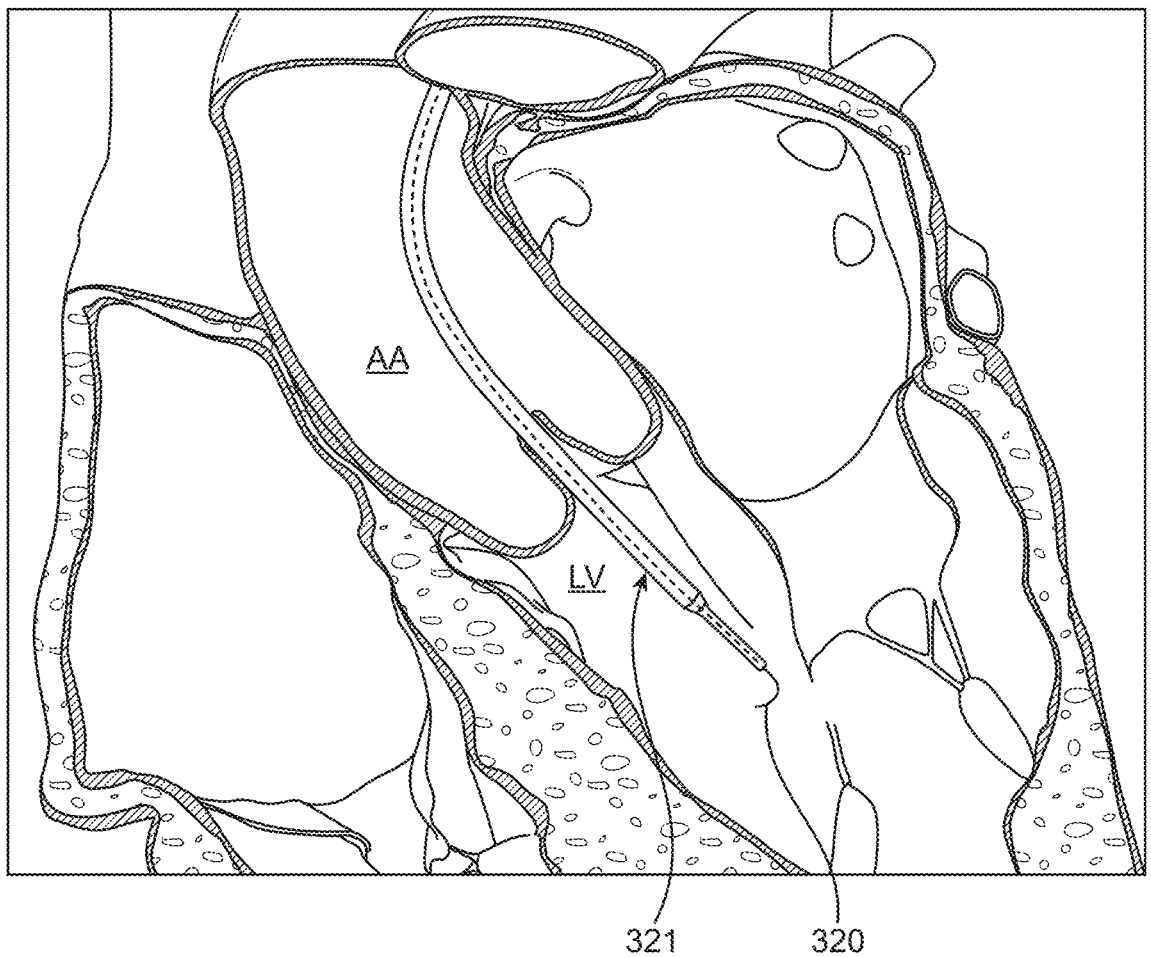

After priming the catheter, access to the patient's vasculature can be obtained (e.g., without limitation, via femoral access) using an appropriately sized introducer sheath. Using standard valve crossing techniques, a diagnostic pigtail catheter may then be advanced over a, for example, 0.035" guide wire until the pigtail catheter is positioned securely in the target location (e.g., left ventricle). The guidewire can then be removed and a second wire 320 (e.g., a 0.018" wire) can be inserted through the pigtail catheter. The pigtail catheter can then be removed (see FIG. 12A), and the blood pump 321 (including a catheter, catheter sheath, and pump portion within the sheath; see FIG. 12B) can be advanced over the second wire towards a target location, such as spanning an aortic valve "AV," and into a target location (e.g., left ventricle "LV"), using, for example, one or more radiopaque markers to position the blood pump.

Figure 12C:
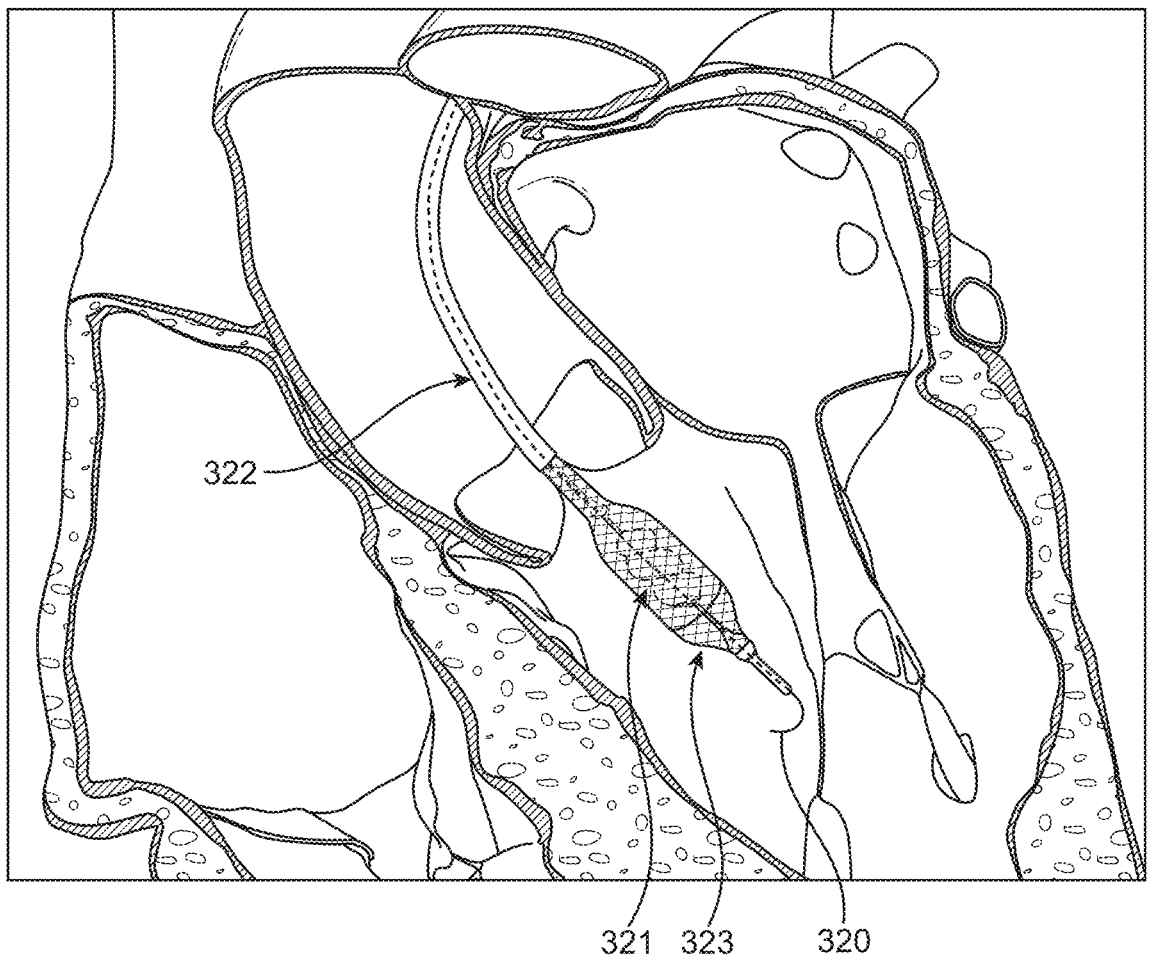
Figure 12D:
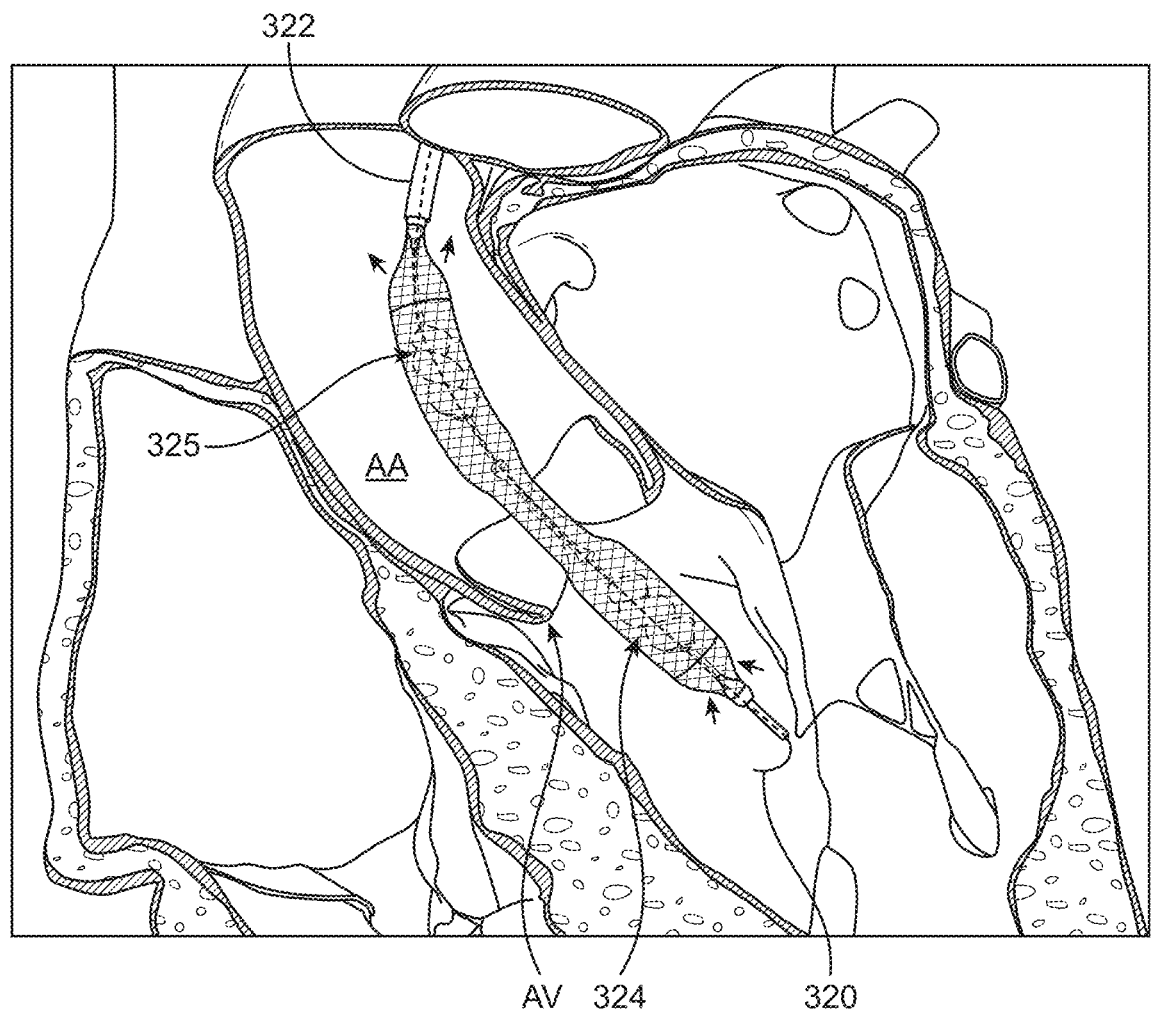

Once proper placement is confirmed, the catheter sheath 322 (see FIG. 12C) can be retracted, exposing first a distal region of the pump portion. In FIG. 12C a distal region of an expandable housing has been released from sheath 322 and is expanded, as is distal impeller 324. A proximal end of housing 323 and a proximal impeller are not yet released from sheath 322. Continued retraction of sheath 322 beyond the proximal end of housing 323 allows the housing 323 and proximal impeller 325 to expand (see FIG. 12D). The inflow region (shown with arrows even though the impellers are not yet rotating) and the distal impeller are in the left ventricle. The outflow (shown with arrows even though the impellers are not rotating yet) and proximal impeller are in the ascending aorta AA. The region of the outer housing in between the two impellers, which may be more flexible than the housing regions surrounding the impellers, as described in more detail herein, spans the aortic valve AV. In an exemplary operating position as shown, an inlet portion of the pump portion will be distal to the aortic valve, in the left ventricle, and an outlet of the pump portion will be proximal to the aortic valve, in the ascending aorta ("AA").

Figure 12E:
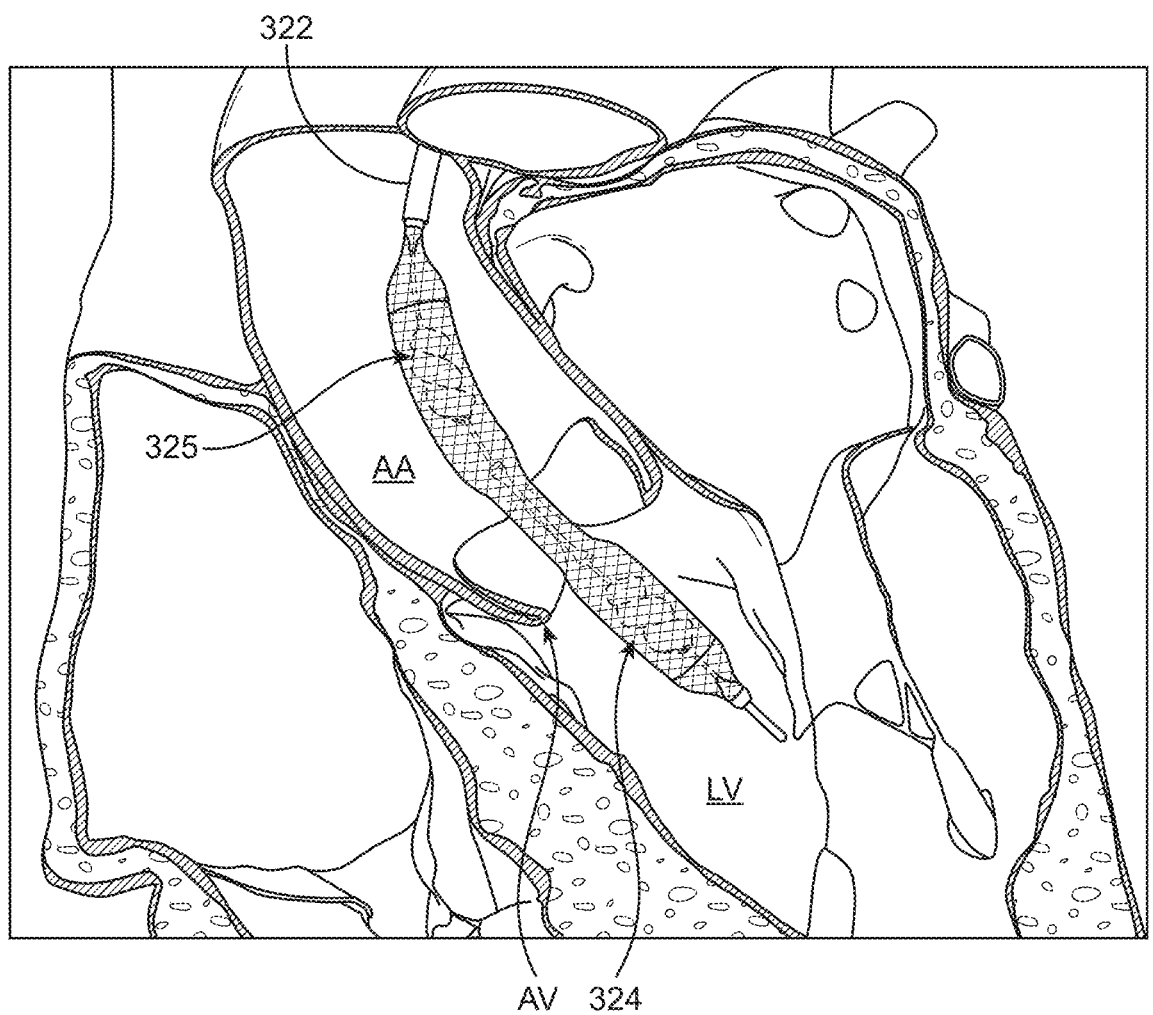
Figure 12F:
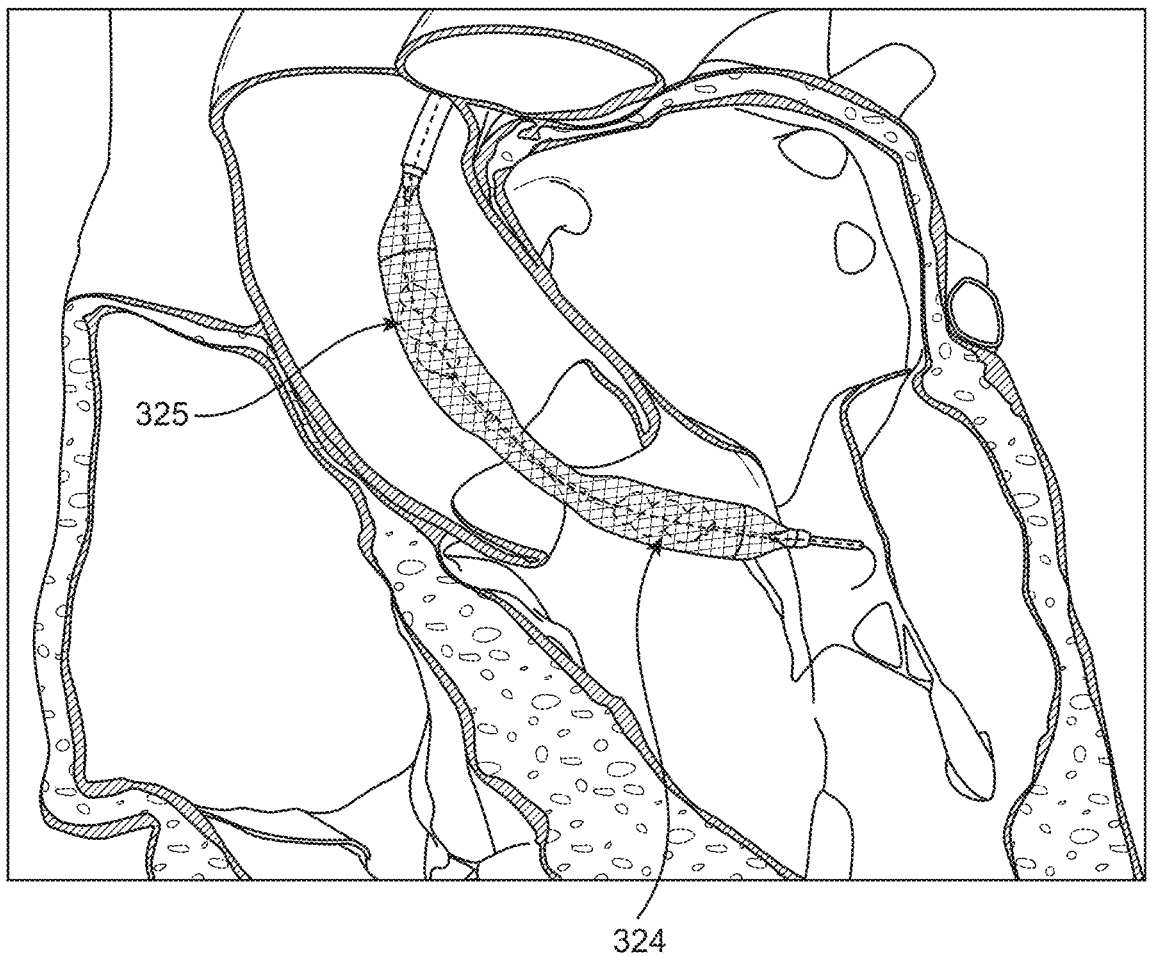

The second wire (e.g., an 0.018" guidewire) may then be moved prior to operation of the pump assembly (see FIG. 12E). If desired or needed, the pump portion can be deflected (active or passively) at one or more locations as described herein, as illustrated in FIG. 12F. For example, a region between two impellers can be deflected by tensioning a tensioning member that extends to a location between two impellers. The deflection may be desired or needed to accommodate the specific anatomy. As needed, the pump portion can be repositioned to achieve the intended placement, such as, for example, having a first impeller on one side of a heart valve and a second impeller on a second side of the heart valve. It is understood that in FIG. 12F, the pump portion is not in any way interfering or interacting with the mitral valve, even if it may appear that way from the figure.

Some pump portions herein may include one or more expandable struts, the struts extending axially from an end region of the expandable blood conduit, such as in FIGS. 3A-3D, 5, 9, 10 and 11 for example. The struts may be disposed at an outflow of the pump portion or an inflow of the pump portion. For example, distal struts 271 shown in FIG. 5 are disposed in or at an inflow of the exemplary pump portion. Additionally, for example, proximal struts 251 shown in FIG. 10 may be disposed in or at an inflow or an outflow of a pump portion. The struts herein are coupled or secured to the expandable blood conduit, and couple the expandable blood conduit to sections of the catheter pump that are distal and proximal to the expandable blood conduit, and are adapted and configured for expansion and collapse to allow the expandable blood conduit to expand and collapse.

In some embodiments herein, struts that extend axially from an end region of the expandable blood conduit may not be unitary with the expandable blood conduit. In these embodiments, the struts are not formed from the same starting material as a portion of the expandable blood conduit, but rather are components that are secured or coupled (e.g., directly attached) to one or more components of the expandable blood conduit. For example, some expandable blood conduits herein include an expandable scaffold, which may also be referred to herein as an expandable support member, and which provides radial support to the blood conduit when expanded. In some embodiments a plurality of struts that extend from an end region of the blood conduit are non-unitary with an expandable scaffold at the end region. First and second components herein that are described as being non-unitary are components that are not formed from the same starting material, and are coupled or secured together at some time. In some instances herein, components that are described as being integrally formed may refer to materials that are made from the same starting material. This disclosure also includes pump portions of catheter blood pumps that include one or more expandable scaffolds that are not unitary with one or more struts extending from an end region of the expandable scaffold.

Pump portions that include expandable blood conduits (which may include a radially supporting scaffold) that are non-unitary with a plurality of struts extending axially therefrom may provide one or more advantages. For example, one or more aspects of manufacturing the scaffold may be easier if a plurality of struts extending therefrom are not included in one or more assembly steps. For example, methods of manufacturing may include coupling one or more scaffolds to polymeric materials (e.g., membranes) that may define at least part of a blood conduit herein. This type of process may be performed on a mandrel. In some instances, for example, there may be advantages to coupling one or more scaffolds to a membrane (e.g., on a mandrel) without having struts extending from a scaffold when securing the scaffold(s) to the membrane(s). A method of manufacturing may include first creating a sub-assembly of scaffold and membrane, and at a subsequent time attaching a plurality of struts to the sub-assembly. In these exemplary methods of manufacture, one or more layers of a polymeric material may be deposited on a mandrel, and one or more scaffold sections may be applied over (e.g., on) that the one or more polymeric layers. Optionally, one or more additional polymeric layers may be applied over (e.g., on) the one or more scaffold sections, sandwiching the one or more scaffold sections within inner and outer layers. Inner and outer layers in this context may each comprise one or more layers of material (e.g., polymeric material).

At a time subsequent to assembling the expandable blood conduit, one or more non-unitary struts may be coupled to (e.g., directly attached to) one or more end regions of the expandable blood conduit, such as one or both of a proximal end region or a distal end region of the blood conduit. In general, if non-unitary struts are secured to first and second end regions of a blood conduit, struts in a first group of struts that are secured to a first end region are generally referred to together as a plurality of struts, and struts in a second group of struts that are secured to a second end region (which is different than the first end region) are generally referred to together as a plurality of struts, where the first plurality of struts is a different plurality than the second plurality of struts.

An additional exemplary advantage of blood pumps that comprise struts that are not unitary with an expandable blood conduit is that different materials or physical characteristics may be imparted to the struts and blood conduit component(s) (e.g. a scaffold), which may provide more design options for struts and blood conduit components. For example without limitation, struts and scaffold sections that are attached may be different materials, they may have different stiffness, different dimension, and/or it may be easier to configure the struts with a particular expanded configuration.

In any embodiment in which the struts are not unitary with a scaffold of a blood conduit, the struts and scaffold (which may also be referred to herein as an expandable support member) may be attached using a wide variety of techniques and concepts. For example only, any suitable mechanical coupling may be used, such as a female-male type of attachment. The attachments may also include any number of optional manufacturing steps, such as applying a force to the coupled components to cause some deformation to one or more components, or using an adhesive or weld to further strengthen the coupling. Strands of material (e.g., thread, filament, wire) may optionally be used to help secure struts to an end region of a scaffold. Once coupled, the struts are adapted to collapse radially inward for delivery, expand for deployment, and collapse again upon removal of the pump portion from the patient. In any of the embodiments herein the struts may be secured to the scaffold, at least partially, by welding or other bonding of the struts and scaffold together. Any of the struts and scaffolds herein may be secured together using any of the one or more coupling concepts and techniques herein, such as without limitation, a mechanical coupling and additionally welded.

Figure 13A:
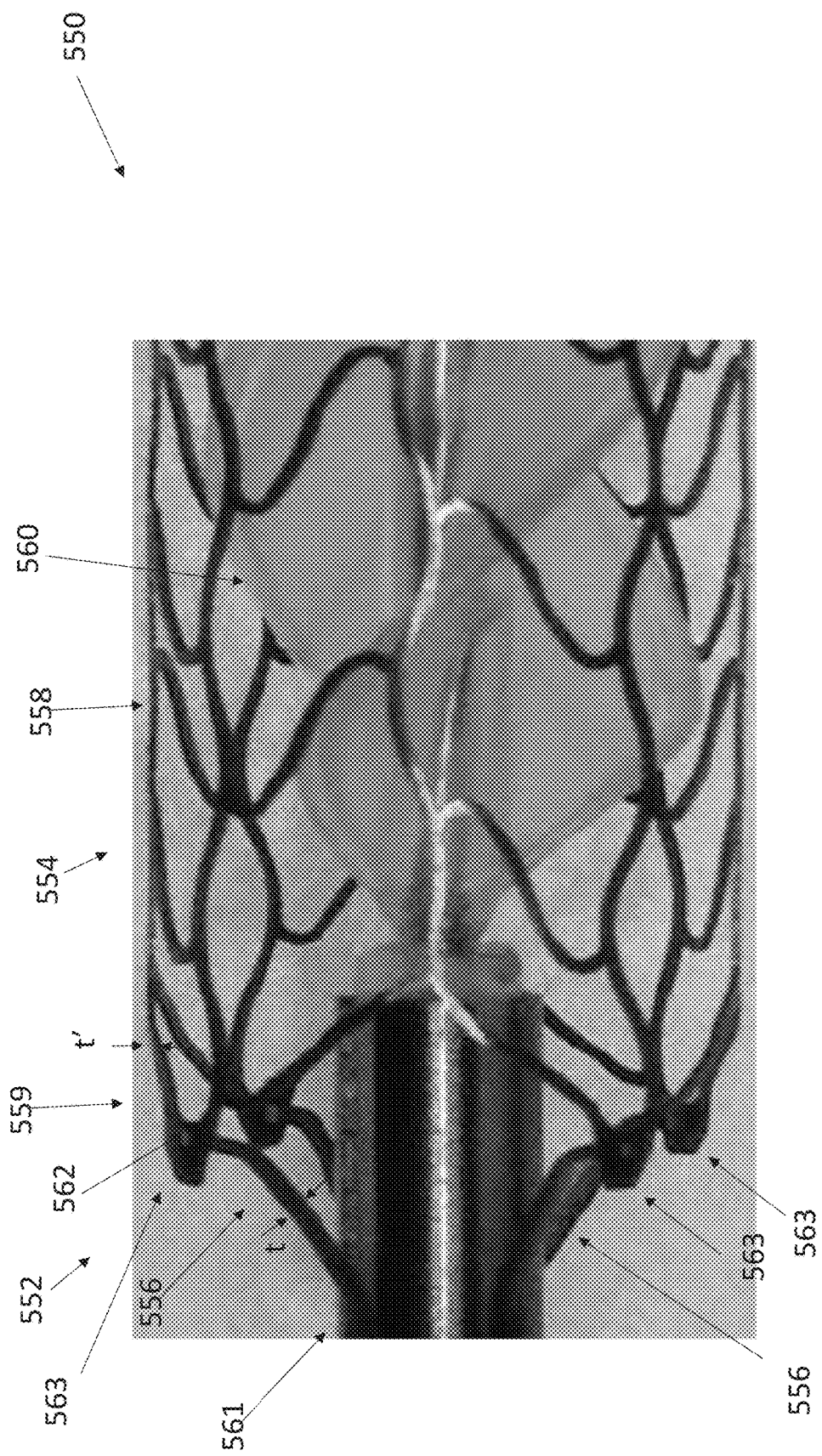
FIG. 13A illustrates exemplary struts that are non-unitary with and coupled to an expandable blood conduit, including an expandable scaffold.
Figure 13B:
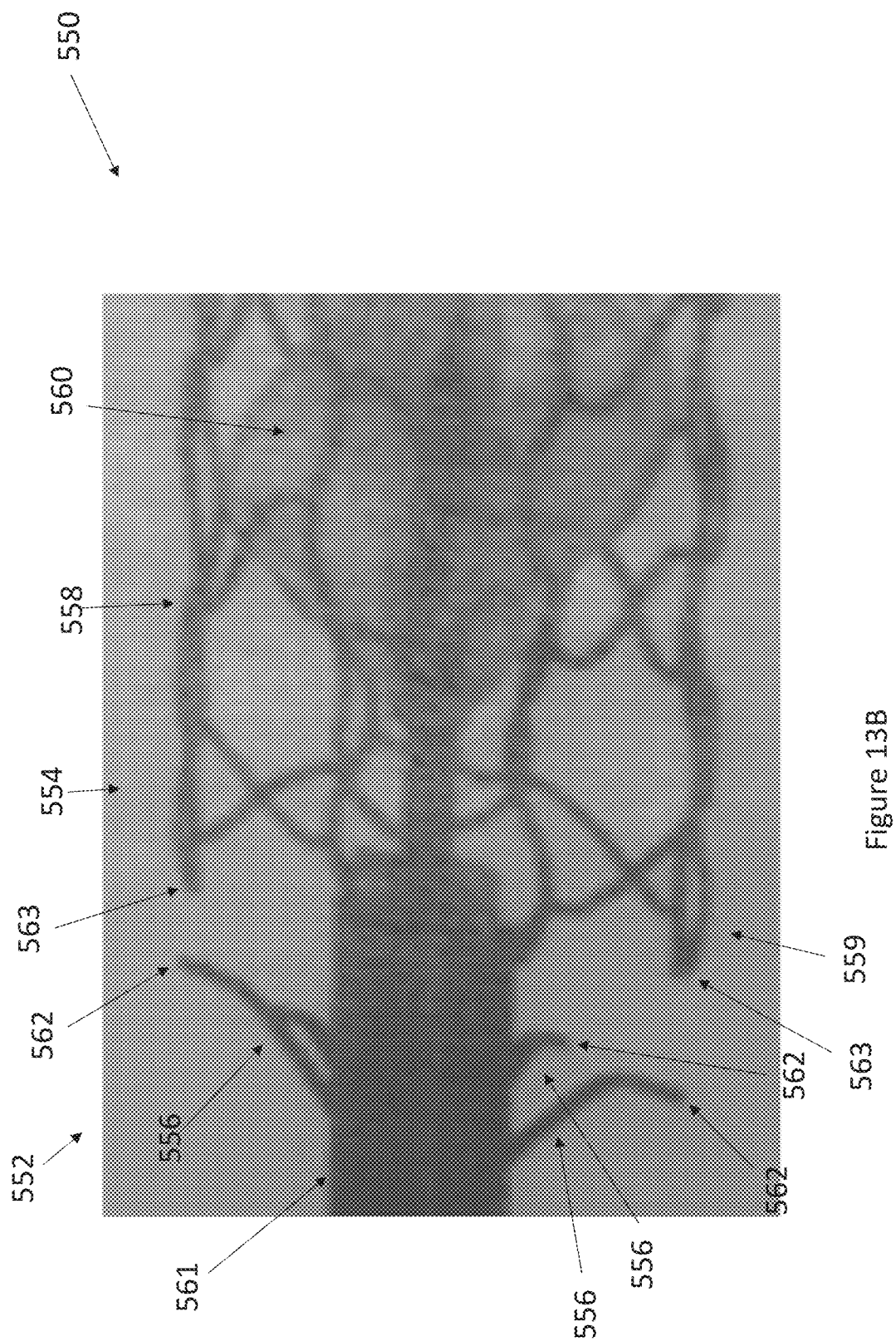
FIG. 13B illustrates exemplary struts that are non-unitary with and not coupled to an expandable blood conduit, including an expandable scaffold.

FIGS. 13A and 13B illustrate a portion of an exemplary pump portion of a catheter pump, and not all components are shown for clarity. The pump portion 550 includes an expandable impeller housing 552 that includes an expandable blood conduit 554 and a plurality of struts 556 (only two of the four struts that are shown are labeled) extending axially from an end region of the expandable blood conduit. In this example the plurality of struts 556 are non-unitary with the expandable blood conduit, and are non-unitary with scaffold 558, but in FIG. 13A are shown coupled and attached directly to scaffold 558 of the blood conduit 554. A membrane (e.g., one or more polymeric layers) is not illustrated in FIGS. 13A and 13B for clarity, but it is understood that the expandable impeller housing in FIGS. 13A and 13B may comprise any of the membranes herein that are coupled to an expandable scaffold. In this example, struts 556 extend between strut hub 561 and scaffold 558. Any of the scaffolds in any particular embodiment herein may have any of the scaffold patterns herein.

The portion of the exemplary pump portion shown in FIGS. 13A and 13B may be a proximal region of an expandable pump portion. In these examples, FIGS. 13A and 13B illustrate a plurality of proximal struts 556 that are non-unitary with a proximal end region 559 of an expandable scaffold. Struts 556 are shown extending axially (proximally in this example) from proximal end region 559. A portion of exemplary impeller 560 is also shown, which includes a plurality of impeller blades as shown. Struts 556 may be at an inflow or an outflow of the expandable impeller housing 552 of the pump portion 550.

The portion of the exemplary pump portion shown in FIGS. 13A and 13B may alternatively be a distal region of an expandable pump portion. In these examples, FIGS. 13A and 13B illustrate a plurality of distal struts 556 that are non-unitary with a distal end region 559 of expandable scaffold (distal is to the left in the figure in this example). Struts 556 are shown extending distally from distal end region 559. A portion of exemplary impeller 560 is also shown, which includes a plurality of impeller blades as shown. Struts 556 may be at an inflow or an outflow of the expandable impeller housing 552. The impeller may be a distal impeller and the pump may optionally also include a proximal impeller, examples of which are described herein. Any other aspect of any catheter blood pump herein or incorporated by reference may be included in these exemplary pump portion, such as any of the motor and/or fluid delivery (e.g., purge, lubricating).

In some examples, both an inflow and an outflow of an expandable impeller housing may include a plurality of struts extending from an end region of a blood conduit and are non-unitary with an expandable scaffold at the end regions. For example, any of the pump portions herein may include an expandable impeller housing that includes a first plurality of struts extending from a proximal end region of a blood conduit that are non-unitary with a scaffold at the proximal end region, and the expandable impeller housing may also include a second plurality of struts extending from a distal end region of a blood conduit that are non-unitary with a scaffold at the distal end region. The scaffolds may be part of the same or common scaffold structure, or they may be separate scaffold sections such as in FIGS. 3A-3D, for example. For example, an expandable impeller housing herein may include a distal portion as illustrated in exemplary FIG. 13A, and it may also include a proximal portion as illustrated in exemplary FIG. 13A.

The scaffolds herein may be manufactured using known techniques for creating stents or stent-like devices. For example, any of the scaffolds herein may be made by laser cutting a tubular member, such as a nitinol tubular member. Any description above related to manufacturing expandable scaffolds or expandable members is incorporated by reference into these embodiments.

FIG. 13B illustrates expandable impeller housing 552 of pump portion 550 from FIG. 13A before struts 556 are coupled to end region 559 of expandable blood conduit 554, and specifically, to scaffold 558. In this exemplary embodiment, pump portion 550 includes a first set of securing members 562, which in this embodiment are part of struts 556, and in this embodiment are each disposed at a first end region of struts 556 as shown. In this exemplary embodiment, pump portion 550 also includes a second set of securing members 563, which are each part of end region 559 of blood conduit 554, and are also part of the end region of scaffold 558. A first securing member 562 and a second securing member 563 are separately and together sized, positioned, and configured to engage one another such that one or more surfaces on each interact and cause a resistance to movement of one or both of the first and securing members in at least one direction. For example, when engaged, the first and/or second member may face resistance to movement in an axial direction (e.g., proximal and/or distal). Additionally, for example, when engaged the first and/or second member may face resistance to movement in a circumferential direction around the blood conduit (e.g., clockwise or counterclockwise in an end view of the impeller housing). Additionally, for example, when engaged the first and/or second member may face resistance to movement in a radial direction (e.g., radially outward or radially inward). Any first securing member and any second securing member herein may be separately and together sized, positioned, and configured to engage one another and thereby resist movement of one or both of the first and securing members in one or more of the aforementioned directions.

In this merely exemplary embodiment, second securing members 563 each comprise a bend formed in the scaffold, and may have valley configurations. In this embodiment, the bends are disposed at ends of scaffold 558, and in this embodiment there are four securing members 563, each of which is adapted and positioned to engage and interface with a first securing member 562 of a strut 556. In this exemplary embodiment, first securing members 562 may have a variety of configurations that are configured to interface with securing members 563 on scaffold 558. For example, securing members 562 may have "T" configurations in which the T shape fits through the space defined by the bend in the scaffold, and the lateral extensions of the "T" shape interface with the scaffold structure on either side of the bend in the scaffold. In another example is that first securing members 562 have comprise a bend or hook configuration that include a bend and then extend proximally towards their furthest end point. In these example, the hooks or bent regions may be passed through the scaffold opening from radially inward to radially outward, and the hook configuration hooks around the bend in the scaffold. In other embodiments the hooks may pass through the bends from radially outward to inward, and hook around the bend in the scaffold. During manufacture a force may optionally be applied to strut bends or hook to further secure the struts to the scaffold. Optionally, the struts may be further secured to the scaffold with a bond such as welding. Welding may optionally be used in combination with any mechanical interaction set forth herein to further secure a strut to a scaffold.

This disclosure also includes methods of manufacturing the pump portions herein, including any of the expandable impeller housings herein, including those that comprise one or more pluralities of struts that are non-unitary with blood conduit and scaffold end regions. The methods of manufacture may include attaching or securing one or more deformable layers of material (e.g., a membrane) to a scaffold which may comprise one or more scaffold sections, and forming a blood conduit. The methods may also include coupling a first plurality of struts to an end region of the blood conduit (such as to a scaffold) and optionally also coupling a second plurality of struts to a second end region of the blood conduit, such as an end region of a scaffold. For example, struts 556 in FIG. 13B may be coupled to scaffold 558, with the resulting coupling shown in FIG. 13A.

The methods of manufacture herein may also include securing an impeller to a drive mechanism, and positioning the impeller within the blood conduit, such as shown in FIGS. 13A and 13B. These methods of manufacturing may also include any other method of manufacturing step(s) described herein. One or more impellers may be positioned within a scaffold before the struts are coupled to the end region of the scaffold, such as is shown in FIG. 13B. FIG. 13B illustrates exemplary pump portion 550 after an impeller 560 and drive mechanism are positioned within scaffold 558 and before plurality of struts 556 have been coupled to the scaffold 558.

As mentioned above, an exemplary advantage of pump portions that include struts that are non-unitary with a blood conduit (including non-unitary with a scaffold thereof) is that struts may be made from different components or parts than the scaffold. This may provide for more design options and allow the struts to comprise a greater variety of materials and/or physical characteristics. For example without limitation, struts and scaffold sections that are not unitary may comprises different materials, they may have different stiffness, they may have different dimensions (e.g., radial thickness or circumferential "width") and/or it may be easier to configure the struts with a particular expanded configuration than if the struts and scaffold were unitary.

In some embodiments individual struts may have a stiffness that is greater than a stiffness of the end region of the scaffold from which they extend. The relative stiffness may be imparted or selected based on the material selection of the different components. In some embodiments, the relative stiffness may be in part due to relative dimensions of the struts and the scaffold. For example without limitation, struts may have a radial thickness (t) as illustrated in FIG. 13A that is greater than a radial thickness (t') of the scaffold in the end region from which the struts extend. Each of the plurality of struts may have a thickness t that is greater than a radial thickness of the scaffold, for example. Other dimensions of the relative components may be also be varied based on the desired properties at any particular location. In some embodiments the struts may comprise a stiffer material than a scaffold material.

The expandable blood conduits herein may not comprise a metallic scaffold (e.g., nitinol scaffold), and the conduit is configured and adapted to define a blood lumen when expanded. In some of these embodiments the blood conduit comprises one or more polymeric materials that define a blood lumen, and radial support is provided by non-metallic structures, such as inflatable components and/or regions of increased polymeric stiffness. For example, the entire disclosure of WO2020028537A1 is incorporated by reference herein for all purposes, such as without limitation inflatable component(s) that are configured and adapted to provide radial support to the blood conduits therein. In these embodiments the struts may still be non-unitary with the expandable blood conduit. The disclosure thus includes struts that are not unitary with the blood conduit, even if the struts are not attached to a metallic scaffold. Additionally, blood conduits herein may include polymeric scaffolds, such as may be formed from polymeric materials. Struts (e.g., metallic, polymeric) may also be non-unitary with a blood conduit, including polymeric scaffolds, in these alternative examples.

The plurality of struts may comprise a material with a different chemical structure than a chemical structure of a scaffold material. That is, the type of material used for the struts may be different than the type of material used for the scaffold. For example, the struts may be made from nitinol, and the scaffold may be made from a different type of metal alloy, or vice versa. In any of the embodiments herein, struts may be made from the same material as the expandable scaffold (e.g., both made from Nitinol).

As shown in FIGS. 13A and 13B, proximal struts 556 may have a non-constant slope from a first end (e.g., proximal end) to a second end (e.g., distal end) of the struts. In this merely exemplary embodiment, a first section (which may be a proximal section or a distal section) of struts 556 has a constant or nearly constant slope as shown, and in an axially adjacent section (e.g, further distally or further distally) the slope increases, as shown, with a bend in between the two regions. The region of the struts closer to the expandable scaffold is, in this exemplary embodiment, more orthogonally oriented when expanded than the region of the struts axially further from the expandable scaffold, as shown. In other embodiments the slope of the struts in expanded configuration may be different than that in FIGS. 13A and 13B, such as constant or substantially constant along the length. The struts may have other configurations as well, such as other complex shapes.

A first region of any strut herein that is adjacent an expandable scaffold may be orthogonal, or substantially orthogonal, relative to a long axis of the expandable blood conduit. A second region axially further away from the expandable scaffold than the first region may have a configuration that is less orthogonally oriented, and optionally closer to parallel to the long axis (but not necessarily parallel), such as is shown in the struts in FIGS. 13A and 13B.

FIGS. 13A and 13B also illustrate a plurality of struts that may be formed unitarily with each other from a common starting structure. For example only, struts 556 may be formed starting with a tubular member 561, such as by laser cutting away material, to thereby create struts 556 with a first strut end extending from hub 561 and a second (free) end disposed away from the hub. The struts may be set in any desired expanded configuration, such as those shown in FIGS. 13A and 13B. The struts are configured to expand to the expanded configurations (e.g., such as shown in FIGS. 13A and 13B) when a radial constraint (such as from a delivery sheath) is removed, examples of which are described herein.

A drive mechanism for rotating one or more impellers may be disposed within and/or pass through strut hub 561. Any of the struts herein may be manufactured in this manner. Hub 561 is cylindrical in this example, but may have other outer profiles, such as rectilinear or curvilinear. Hub 561 includes a bore extending therethrough, allowing for a drive mechanism, and any number of bearings that facilitate the rotation of the one or more impellers. Hub 561 includes outer recesses in this embodiment, which are formed when the struts are formed and deformed radially away relative to the hub body.

FIGS. 13A and 13B may additionally illustrate struts that are coupled to end regions of scaffolds similar to those in FIGS. 3A-3D, 9 and 10, which may comprise scaffold sections that are disposed around an impeller. The non-unitary struts herein may be coupled to only one end region of either or both of the impeller scaffolds in FIGS. 3A-3D, 9 and 10, or non-unitary struts may be coupled to both end regions of either or both of the impeller scaffolds in FIGS. 3A-3D, 9 and 10. For example, in the examples in FIGS. 3A-3D, 9 and 10, there may be only one plurality of non-unitary struts, there may be first and second pluralities of non-unitary struts, there may be first, second and third pluralities of non-unitary struts, or there may be first, second, third and fourth pluralities of non-unitary struts. In some embodiments a proximal impeller scaffold may be coupled to a first plurality of non-unitary struts or to a first and second plurality of non-unitary struts. In some embodiments a distal impeller scaffold may be coupled to a first plurality of non-unitary struts or to a first and second plurality of non-unitary struts. Any of the pluralities of struts herein may thus be coupled, secured or attached to a scaffold or scaffold section in a non-unitary manner, which may provide any of the exemplary benefits provided herein.

It may be advantageous for the pump portion to have different properties or characteristics at different axially locations along the pump portion. In some embodiments it may be advantageous for the pump to have non-unitary struts at certain locations but not at others. For example, it may be advantageous to have struts at an outflow that are non-unitary with an end region of a scaffold near the outflow, but advantageous (or at least not disadvantageous) to have struts at an inflow of the pump that are unitary with a scaffold end region near the inflow of the pump portion. For example only, it may be advantageous to provide outflow struts with physical properties or characteristics, such as greater stiffness, but it may not be as advantageous or desired to have inflow struts with characteristics much different than an inflow end region of a scaffold. Pump portions herein may thus have unitary inflow struts and non-unitary outflow struts, or vice versa. Additionally, in embodiments such as in FIGS. 3A-3D, 9 and 10 with multiple impeller scaffold sections, it may be advantageous to include non-unitary struts at end regions of the blood conduit, and it may not be as advantageous or desired to have non-unitary struts at axially inner strut locations (which are within the blood conduit), or vice versa.

FIGS. 14A and 14B illustrate merely exemplary strut assemblies that includes a plurality of struts that are configured to be non-unitary with an end region of an expandable blood conduit. Many of the other pump components are not shown for clarity. FIG. 14A illustrates an exemplary strut assembly including a plurality of struts 622 (four are shown in this example). In this example each strut 622 has a first end extending from strut hub 621 towards a free end, as shown. Each of struts 622 includes a securing member 630 in a free end region as shown. Securing members 630 may be considered to provide similar functionality as securing members 562 in FIGS. 13A and 13B. Securing members 630 include an opening or space through the struts 622, as shown. Securing members 630 are configured, sized and positioned to interface with an end region of any of the scaffolds herein, wherein a portion of the scaffold regions extends at least partially within the opening or space in the strut 622. The securing members 630 of struts 622 include closed free ends 627, open regions 624 and 626, and interface or securing feature 625, which in this embodiment include first and second protrusions that extend from first and second side arm sections of struts 622. The side arms, protrusions 625 that extend therefrom, and closed end 627 at least partially define the opening or space in the strut 622 which is configured to a receive a scaffold section.

FIG. 14B illustrates an exemplary strut 622 from FIG. 14A coupled or secured to an end portion of an exemplary scaffold and is non-unitary with the end portion. FIG. 14B illustrates a merely exemplary coupling between non unitary struts and an end region of an expandable scaffold. In this example, the scaffold (only a very small portion of which is shown) end region includes an elongate arm 643 that includes first and second protrusions 641 that extend outward from the elongate body of arm 643. In this embodiment first and second protrusions 641 extend laterally from arm body 643. Scaffold arms 643 (only one is shown) includes a first end 642 as well. Arm 643 extends at least partially within the opening or space in strut 622. In this example, protrusions 641 are sized and configured to interface with first and second side arms of strut 622 to help resist motion of at least one of the strut and arm 643 in at least one direction, described elsewhere herein. First end 642 of arm 643 is sized and configured to interface with a region of strut 622 to help secure the two components together as well.

To facilitate the coupling of scaffold arm 643 and strut 622, first and second side arms and securing features 625 (protrusions in this embodiment) of the strut may be moved apart from one another to increase the size of the opening or space in the strut. The end of arm 643 (which may be considered to have a "t" or "cross" configuration) may be advanced into the opening or space in the strut, which may occur along with some rotation of the arm 643 to ease the insertion, until the interface features on the two components interface and couple the strut to the scaffold, thereby resisting movement of at least one of the strut and scaffold in at least one direction. A portion of the securing member 630 is therefore above the scaffold and a part of the securing member 630 is below the scaffold, as shown. A region of the strut axially overlaps with the end region of the scaffold, as shown. In the example in FIG. 14B, an end of the strut is further axially in one axial direction (e.g., proximally or distally) than an end of the scaffold end.

As can most easily seen in the top strut 622 in FIG. 14A, the securing members 630 may have a configuration in which the strut, at or just proximate to the opening in the strut, has a bends and follows a radially inward path towards the region where protrusions 625 extend from the side arms, after which the strut configuration follows a path that extends radially outward, forming a dip or valley in the region of the opening or space in the strut, as shown. The strut hubs herein may include recesses 623 or 603 formed therein (only one is labeled in FIGS. 14A and 15) adjacent the struts. These may be formed by machining away material. Any aspect of any struts herein may be incorporated by reference into the examples shown in FIGS. 14A and 14B unless indicated herein to the contrary.

FIG. 15 illustrates an exemplary alternative strut assembly including a plurality of struts. The strut assembly in FIG. 15 may include any of the features and functionality of the strut assembly in FIGS. 14A and 14B. Parts that are similarly labeled in FIGS. 14A, 14B, and 15 may be the same and/or impart the same functionality as described with respect to FIGS. 14A and 14B. One difference between struts 602 shown in FIG. 15 is that securing members 610 have an open end 607, that may facilitate coupling with an end region of the scaffold, which is not shown but could be any of the scaffolds end regions herein, including scaffold arm 643 shown in FIG. 14B, for example. Upon coupling of struts 602 to an end region of the scaffold, an additional securing step may optionally be performed, such as applying force to the open end fingers 609 (labeled on only one strut) to crimp them together, for example, such that they contact each other in a closed configuration. Optionally, the fingers 609 shown at the strut free end may be welded together, creating a closed end of the strut.

The exemplary strut assemblies shown in FIGS. 14A, 14B and 15B may be disposed at a pump inflow or a pump outflow, and they may be proximal struts at a proximal end of the pump portion, distal struts at a distal end of the pump portion, and may be struts that are within the blood conduit, such as the struts in FIGS. 3A-3D that are within the blood conduit. A pump portion herein may thus have any combination of the strut assemblies herein at one or more locations of the pump portion. For example only, a pump portion may include the strut assembly in FIG. 14A at an outflow of an expandable impeller housing and may have unitary struts at an inflow of the expandable impeller housing.

What is claimed is:

1. A catheter blood pump, comprising:
an expandable pump portion extending distally from an elongate shaft, the pump portion including
an expandable impeller housing that includes
an expandable blood conduit defining a blood lumen, and a plurality of expandable struts coupled to and extending axially from an end region of the expandable blood conduit, the plurality of expandable struts non-unitary with an expandable scaffold at the end region, and
one or more expandable impellers disposed at least partially within the blood lumen.

2. The blood pump of claim 1, wherein the plurality of expandable struts are disposed at an outflow of the pump portion.

3. The blood pump of claim 2, wherein the plurality of expandable struts are proximal relative to a proximal end of the expandable blood conduit.

4. The blood pump of claim 1, wherein the plurality of expandable struts are disposed at an inflow of the pump portion.

5. The blood pump of claim 4, wherein the plurality of expandable struts are disposed distal relative to a distal end of the expandable blood conduit.

6. The blood pump of claim 1, the blood pump further comprising a second plurality of struts extending axially from a second end region of the expandable blood conduit, wherein the second plurality of struts are non-unitary with the scaffold.

7. The blood pump of claim 6, wherein the scaffold extends from the end region to the second end region.

8. The blood pump of claim 6, wherein the scaffold is continuous from the end region to the second end region.

9. The blood pump of claim 7, wherein the scaffold includes one or more discontinuities between the end region and the second end region.

10. The blood pump of claim 5, wherein the scaffold includes first and second scaffold sections axially spaced apart.

11. The blood pump of claim 10, wherein the first and second scaffold sections are disposed at first and second impeller regions.

12. The blood pump of claim 11, wherein the blood conduit includes a central region in between the first and second scaffold sections, wherein the central region is void of a scaffold.

13. The blood pump of claim 1, the blood pump further comprising a second plurality of expandable struts extending axially from a second end region of the expandable blood conduit, wherein the second plurality of struts are unitary with the scaffold.

14. The blood pump of claim 1, wherein the plurality of expandable struts have a radial thickness greater than a radial thickness of the scaffold in the end region.

15. The blood pump of claim 1, wherein the plurality of expandable struts extend from a common hub.

16. The blood pump of claim 1, wherein each of the plurality of struts has a stiffness that is greater than a region of the scaffold to which it is coupled.

17. The blood pump of claim 1, wherein the plurality of struts each have a first securing member secured to a second securing member of the scaffold.

18. The blood pump of claim 17, wherein the first securing members are disposed at an end region of the struts.

19. The blood pump of claim 17, wherein the first securing members comprise a bend in the strut.

20. The blood pump of claim 17, wherein the first securing members including one or more projections that project away from an elongate strut body.

21. The blood pump of claim 17, wherein the first securing members have a T configuration.

22. The blood pump of claim 17, wherein the first securing members have a hook configuration.

23. The blood pump of claim 17, wherein the second securing member comprises a bend in the scaffold.

24. The blood pump of claim 17, wherein the second securing member has a valley configuration in the scaffold.

25. The blood pump of claim 17, wherein the first securing members comprise an opening in the strut.

26. The blood pump of claim 25, wherein the plurality of struts have closed free ends.

27. The blood pump of claim 25, wherein the plurality of struts have open free ends, optionally including a plurality of fingers that define the open end.

28. The blood pump of claim 25, wherein the first securing members comprise one or more projections extending from side arms of the strut, the projections partially defining the opening in the strut.

29. The blood pump of claim 25, wherein the first securing members have a valley configuration comprising a bend.

30. The blood pump of claim 25, wherein the second securing member comprises an elongate body that extends at least partially within the opening.

31. The blood pump of claim 30, wherein the second securing member comprises one or more projections that project away from the elongate body member and interface with the strut.

32. The blood pump of claim 31, wherein the one or more projections interface with first and second side arms of the strut.

33. The blood pump of claim 32, wherein the first securing members are configured to provide for movement between first and second side portions of the strut to facilitate coupling with the scaffold.

34. The blood pump of claim 17, wherein the first securing member and the second securing member are separately and together sized, positioned, and configured to engage one another such that one or more surfaces on each interact and cause a resistance to movement of one or both of the first and securing members in at least one direction.

35. The blood pump of claim 34, wherein the first securing member and the second securing member are separately and together sized, positioned, and configured to engage one another such that one or more surfaces on each interact and cause a resistance to movement of one or both of the first and securing members in an axial direction.

* * * * *